(12) United States Patent
Salvemini

(10) Patent No.: US 8,747,844 B2
(45) Date of Patent: Jun. 10, 2014

(54) METHODS OF TREATING PAIN

(75) Inventor: Daniela Salvemini, Chesterfield, MO (US)

(73) Assignee: Saint Louis University, St. Louis, MO (US)

( * ) Notice: Subject to any disclaimer, the term of this patent is extended or adjusted under 35 U.S.C. 154(b) by 76 days.

(21) Appl. No.: 13/189,954

(22) Filed: Jul. 25, 2011

(65) Prior Publication Data

US 2012/0039866 A1   Feb. 16, 2012

Related U.S. Application Data

(60) Provisional application No. 61/369,504, filed on Jul. 30, 2010.

(51) Int. Cl.
| | |
|---|---|
| A61K 31/00 | (2006.01) |
| A61K 31/133 | (2006.01) |
| A61K 31/137 | (2006.01) |
| A61K 31/40 | (2006.01) |
| A61K 39/00 | (2006.01) |

(52) U.S. Cl.
USPC .................. 424/130.1; 514/1; 514/408

(58) Field of Classification Search
None
See application file for complete search history.

(56) References Cited

U.S. PATENT DOCUMENTS

| | | |
|---|---|---|
| 2006/0270630 A1 | 11/2006 | Smith et al. |
| 2007/0082933 A1 | 4/2007 | Binkert et al. |

FOREIGN PATENT DOCUMENTS

| | | |
|---|---|---|
| EP | 1431284 A1 | 6/2004 |
| EP | 1484057 A1 | 12/2004 |
| EP | 1733724 A1 | 12/2006 |
| WO | 99/37298 A1 | 7/1999 |
| WO | 2004/105773 A2 | 12/2004 |
| WO | 2007/092638 A1 | 8/2007 |
| WO | 2008070344 A2 | 6/2008 |
| WO | 2008/141013 A1 | 11/2008 |
| WO | 2009124294 A2 | 10/2009 |
| WO | 2010/019646 A1 | 2/2010 |

OTHER PUBLICATIONS

Matsuura et al. (2000). Effect of FTY720, a novel immunosuppressant, on adjuvant- and collagen-induced arthritis in rats. International Journal of Immunopharmacology. 22(4):323-331.*

Doyle, Tim et al: "Role for peroxynitrite in sphingosine-1-phosphate-induced", PAIN, 152 (3), 643-648 CODEN: PAINDB; ISSN: 0304-3959, Apr. 2011, XP002667360.

Doyle, Tim et al: "Sphingosine-1-phosphate acting via the S1P1 receptor is a downstream signaling pathway in cerarninde-induced hyperalgesia", Neuroscience Letters, vol. 499, No. 1, Jul. 1, 2011, pp. 4-8, XP55016229, ISSN: 0304-3940, DOI: 10.1016/j.neulet.2011. 05.018 abstract; figure 3.

Bollag, Wendy B.: "Potential role of sphingosine 1-phosphate in the pathogenesis of rheumatoid arthritis", Journal of Lipid Research, vol. 49, No. 11, Nov. 2008, pp. 2281-2282, XP002667398, ISSN: 0022-2275 the whole document.

M.M. Ndengele et al: "Spinal Ceramide Modulates the Development of Morphine Antinociceptive Tolerance via Peroxynitrite-Mediated Nitroxidative Stress and Neuroimmune Activation", Journal of Pharmacology and Experimental Therapeutics, vol. 329, No. 1, Apr. 1, 2009, pp. 64-75, XP55010200, ISSN: 0022-3565, DOI: 10.1124/jpet.108. 146290 the whole document.

European Patent Office (Searching Authority) Notification of the International Search Report and the Written Opinion of the International Searching Authority, Notice dated Jan. 30, 2012; for International Application No. PCT/US2011/045236 filed Jul. 25, 2011.

Muscoli Carolina et al: "Counter-Regulation of Opioid Analgesia by Glial-Derived Bioactive Sphingolipids", Journal of Neuroscience, vol. 30, No. 46, Nov. 2010, pp. 15400-15408, XP002662965, ISSN: 0270-6474 The whole document.

Coste Ovidiu et al: "Antinociceptive activity of the S1P-receptor agonist FTY720" Journal of Cellular and Molecular Medicine, vol. 12, No. 3, Jun. 2008, pp. 995-1004, XP002662966, ISSN: 1582-1838 The whole document.

Lai Wen-Qi et al: "Anti-inflammatory effects of sphingosine kinase modulation in inflammatory arthritis.", Journal of Immunology (Baltimore, MD. :1950) Dec. 1, 2008 LNKD-PUBMD: 19017993, vol. 181, No. 11, Dec. 1, 2008, pp. 8010-8017, XP002662967, ISSN: 1550-6606 The whole document.

Nicol Grant D: "Nerve growth factor, sphingomyelins, and sensitization in sensory neurons.", Sheng Li Xue Bao: [Acta Physiologica Sinica] Oct. 25, 2008, pp. 603-604, XP002662968, ISSN 0371-0874 The whole document.

Coste Ovidiu et al: "Sphingosine 1-Phosphate Modulates Spinal Nociceptive Processing", Journal of Biological Chemistry, vol. 283, No. 47, Nov. 2008, pp. 32442-32451, XP002662969, ISSN: 0021-9258; abstract p. 32444. right hand column, last paragraph-p. 32445, left-hand column, paragraph 1; figure 2.

European Patent Office (Searching Authority) Invitation to Pay Additional Fees and, Where Applicable, Protest Fee; Nov. 17, 2011; for International Application No. PCT/US2011/045236 filed Jul. 25, 2011.

* cited by examiner

*Primary Examiner* — Christine J Saoud
*Assistant Examiner* — Jon M Lockard
(74) *Attorney, Agent, or Firm* — Parker Highlander PLLC

(57) ABSTRACT

The invention relates to methods for treating pain disorders including neuropathic and inflammatory pain and to methods to reduce or eliminate nociceptive tolerance induced by opiate analgesic use by administering an agent that suppresses or blocks S1P biological activity.

7 Claims, 31 Drawing Sheets
(10 of 31 Drawing Sheet(s) Filed in Color)

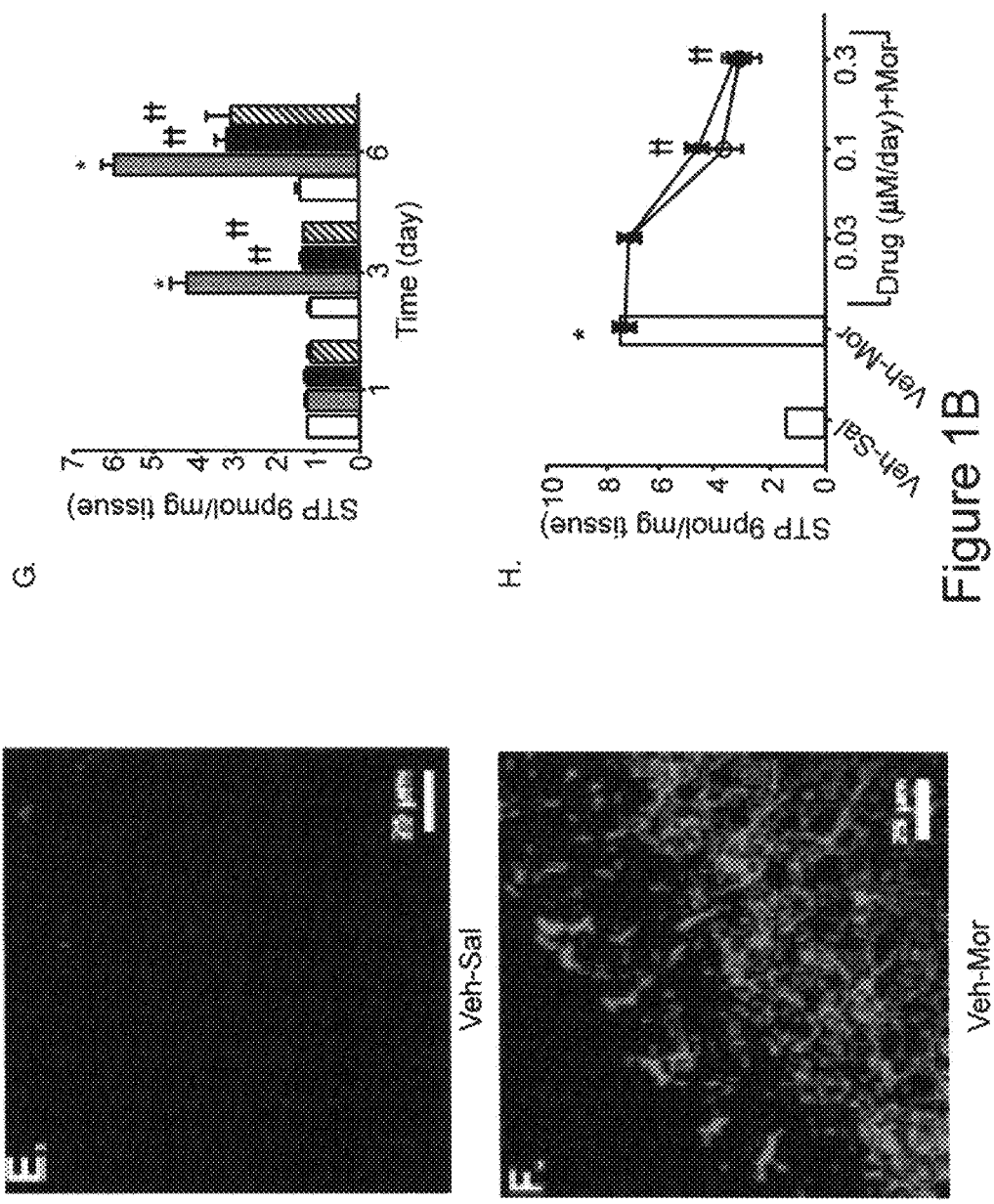

SEQUENCE LISTING

<160> NUMBER OF SEQ ID NOS: 2

<210> SEQ ID NO 1
<211> LENGTH: 220
<212> TYPE: PRT
<213> ORGANISM: Homo sapiens -continued

<400> SEQUENCE: 1

Glu Val Gln Leu Val Gln Ser Gly Ala Glu Val Lys Lys Pro Gly Glu
1               5                   10                  15

Ser Leu Lys Ile Ser Cys Gln Ser Phe Gly Tyr Ile Phe Ile Asp His
            20                  25                  30

Thr Ile His Trp Met Arg Gln Met Pro Gly Gln Gly Leu Glu Trp Met
        35                  40                  45

Gly Ala Ile Ser Pro Arg His Asp Ile Thr Lys Tyr Asn Glu Met Phe
    50                  55                  60

Arg Gly Gln Val Thr Ile Ser Ala Asp Lys Ser Ser Thr Ala Tyr
65                  70                  75                  80

Leu Gln Trp Ser Ser Leu Lys Ala Ser Asp Thr Ala Met Tyr Phe Cys
                85                  90                  95

Ala Arg Gly Gly Phe Tyr Gly Ser Thr Ile Trp Phe Asp Phe Trp Gly
            100                 105                 110

Gln Gly Thr Met Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys
    210                 215                 220

<210> SEQ ID NO 2
<211> LENGTH: 213
<212> TYPE: PRT
<213> ORGANISM: Homo sapiens

<400> SEQUENCE: 2

Glu Thr Thr Val Thr Gln Ser Pro Ser Phe Leu Ser Ala Ser Val Gly
1               5                   10                  15

Asp Arg Val Thr Ile Thr Cys Ile Thr Thr Asp Ile Asp Asp Asp
            20                  25                  30

Met Asn Trp Phe Gln Gln Glu Pro Gly Lys Ala Pro Lys Leu Leu Ile
        35                  40                  45

Ser Glu Gly Asn Ile Leu Arg Pro Gly Val Pro Ser Arg Phe Ser Ser
    50                  55                  60

Ser Gly Tyr Gly Thr Asp Phe Thr Leu Thr Ile Ser Lys Leu Gln Pro
65                  70                  75                  80

Glu Asp Phe Ala Thr Tyr Tyr Cys Leu Gln Ser Asp Asn Leu Pro Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln

-continued

```
145                 150                 155                 160
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu
        210
```

METHODS OF TREATING PAIN

CROSS-REFERENCE TO RELATED APPLICATIONS

The Present Application claims the benefit of U.S. Provisional Patent Application No. 61/369,504, filed Jul. 30, 2010, the entire contents of which are incorporated herein by reference.

STATEMENT REGARDING FEDERALLY SPONSORED RESEARCH OR DEVELOPMENT

This invention was made with Government support under National Institutes of Health Grants R01 DA024074 and R21 DA023056. The Federal Government has certain rights in the invention.

INCORPORATION-BY-REFERENCE OF INFORMATION SUBMITTED ELECTRONICALLY

The Sequence Listing, which is a part of the present disclosure, includes the sequences SEQ comprising nucleotide and amino acid sequences of the present invention. The subject matter of the Sequence Listing is incorporated herein by reference in its entirety.

FIELD

The invention relates to methods of treating pain using at least one of sphingosine kinase antagonist, S1P antagonist, or S1P receptor antagonist. The invention further relates to the use of S1P receptor agonists, such as Fingolimod, BAF312, Ponesimod, ONO-4641, CS-0777, KRP-203, PF-991, and W146, and antagonists, such as antibodies, in the treatment and prevention of neuropathic pain including cancer and chemotherapy-induced pain, acute and chronic inflammatory pain, and the development of opiate-induced hypersensitivity (hyperalgesia and allodynia), and antinociceptive tolerance. Kits comprising sphingosine kinase antagonists, S1P antagonists, S1P receptor agonists, and S1P receptor antagonists are also provided.

INTRODUCTION

A devastating health problem in the United States and abroad is the inadequate treatment of pain. One third of all Americans suffer from some form of chronic pain, and a third of these have pain, which is resistant to current medical therapy. The economic impact of pain is equally large at approximately $100 billion annually (Renfrey et al., 2003). Severe pain syndromes reduce quality of life in patients, partly because reduced analgesic effectiveness with chronic opiate therapy (i.e., hyperalgesia and tolerance) leads to escalating doses and distressing side effects. Accordingly, there is major interest in new approaches to maintain opiate efficacy during repetitive dosing for chronic pain, without engendering tolerance or unacceptable side-effects.

Opiate/narcotic analgesics, typified by morphine, are the most effective treatments for acute and chronic severe pain. However, their clinical utility is often hampered by the development of analgesic tolerance which requires escalating doses to achieve equivalent pain relief (Foley, 1995). This complex pathophysiological cycle represents a critical barrier to the quality of life of these patients due to the resulting oversedation, reduced physical activity, constipation, respiratory depression, high potential for addiction, and other side-effects (Foley, 1995). Adaptive modifications in cellular responsiveness have been proposed as contributing to tolerance (Taylor and Fleming, 2001). An alternative hypothesis with in vivo evidence in animals (Mao et al., 1995) and in humans (Amer et al., 1988) is that chronic stimulation of opioid receptors triggers the activation of anti-opioid systems that reduce sensory thresholds, thereby resulting in hypersensitivity to tactile and noxious thermal stimulation (Simonnet and Rivat, 2003). As a corollary to this hypothesis, such opioid-induced hypersensitivity paradoxically diminishes the net analgesic effect of the opioid agonist (Ossipov et al., 2003; Simonnet and Rivat, 2003).

Ceramide, a potent proinflammatory and proapoptotic sphingolipid (Hannun and Obeid, 2008) is generated by enzymatic hydrolysis of sphingomyelin (SM) by sphingomyelinases (SMases) ("SM pathway") and from de novo synthesis by serine palmitoyltransferase (SPT) and ceramide synthase (CS) ("de novo pathway") (Delgado et al., 2006). The development of morphine-induced tolerance is associated with increased formation of ceramide in the spinal cord and inhibition of its biosynthesis blocked the development of antinociceptive tolerance (Bryant et al., 2009; Ndengele et al., 2009). Once generated, the steady-state availability of ceramide is further regulated by ceramidases that convert ceramide to sphingosine (SP), with SP then converted by sphingosine kinase 1 and 2 (Melendez, 2008; Takabe et al., 2008) to Sphingosine-1-Phosphate (S1P), the GPCR-signaling end product in the ceramide metabolic pathway (Melendez, 2008; Takabe et al., 2008). Once generated, S1P diffuses extracellularly so to act on GPCR-coupled S1P receptors (five identified to date, known respectively as S1P[1-5], also known as S1PR$_{[1-5]}$) found on several cells of the CNS including neurons and glial cells (Taha et al., 2004; Melendez, 2008; Takabe et al., 2008).

Anti-S1P antibodies have been developed as cancer treatments. The crystal structure of an anti-S1P monoclonal antibody bound with its ligand is provided as Protein Databank No. 319G. See also U.S. patent application Ser. No. 20070148168; U.S. Pat. Nos. 6,881,546 and 6,858,383; and U.S. patent application Ser. No. 10/029,372, each of which is incorporated by reference in its entirety. SPHINGOMAB™, a murine monoclonal antibody (mAb) developed by Lpath, Inc. has been shown to be effective in treating cancer. A series of humanized anti-S1P monoclonal antibodies have been developed, and are described in U.S. patent application Ser. Nos. 60/854,971 and 11/924,890, now issued as U.S. Pat. No. 7,829,674, and corresponding PCT application PCT/US2007/082647, each of which applications is incorporated by reference in its entirety. One particularly effective example of such a humanized antibody is referred to as LT1009 (available commercially as Sonepcizumab™, Lpath, Calif.), which antibody has exhibited greater activity than SPHINGOMAB™ in the treatment of cancer.

While progress has been made in terms of modifications of opioid agonists to improve their formulated delivery, pharmacokinetics, and potential for abuse, little progress has been made in preventing the development of neuropathic pain, inflammatory pain and hyperalgesia. Thus, there is a serious need for new agents and methods of treating those conditions.

FIGURES

The patent or application file contains at least one drawing executed in color. Copies of this patent or patent application publication with color drawing(s) will be provided by the Office upon request and payment of the necessary fee.

Those of skill in the art will understand that the figures, described below, are for illustrative purposes only. The figures are not intended to limit the scope of the present teachings in any way.

FIG. 1. Morphine-induced hyperalgesia and tolerance is associated with increased ceramide and S1P derived from activation of sphingosine kinase. When compared to rats that received a chronic s.c. infusion of saline (Veh-Sal, n=5, ● or open bar) over 7 days, infusion of morphine over the same time frame (Veh-Mor, n=5, ■ or gray bar) led to the development of (A, C) thermal hyperalgesia as evidenced by a significant reduction in paw-withdrawal latency (s) on day 3 and 6 when compared to paw-withdrawal latency from before implantation of the osmotic minipump (t=0 h) and (B, D) to the development of antinociceptive tolerance. Results shown in B and D are from behavioral measurements taken on day 6. These events were associated with increased formation of ceramide (red, E, F) and S1P (G, H) in dorsal horn tissues. Co-administration of morphine with DMS (0.3 μM/day/6 days, n=5, ▲ or black bar) or SK-I (0.3 μM/day/6 days, n=5, ◆ or hashed bar) blocked the development of hyperalgesia (A), tolerance (B) and S1P (G, H). Dose response curves for DMS (0.03-0.3 μM/day/6 days, n=5, ● or black bar) or SK-I (0.3-0.3 μM/day/6 days, n=5, ○ or hashed bar) on day 6 are shown in C for hyperalgesia, D for tolerance and H for S1P. Micrographs shown in (E and F) are representative of at least 3 images of the superficial layers of dorsal horn (L4-L6) harvested on day 6 from 3 different animals. Results are expressed as mean±SEM for n=5 animals and analyzed by ANOVA with Dunnett's post hoc test where *$P<0.001$ for Veh-Mor vs Veh-Sal; §$P<0.01$ or §§$P<0.001$ vs t=0 h; and † $P<0.01$ or †† $P<0.001$ for Drugs-Mor vs Veh-Mor.

FIG. 2. Co-localization of ceramide with activated glial cells but not neurons. Fixed frozen spinal cord sections from (A-C) Veh-Sal and (D-F) Veh-Mor rats were stained for ceramide (red) and for (A,D) astrocytes (GFAP+, green), (B,E) microglia (Iba1+, green), or (C,F) neurons (NeuN+, green). In these merged images, ceramide was low or absent in spinal cords from Veh-Sal animals and substantially increased in spinal cords from Veh-Mor animals. Furthermore, ceramide levels co-localized (yellow) with (D) astrocytes and (E) microglia, but not with (F) neurons. Negative controls using normal rabbit serum (for ceramide) or normal mouse IgG (for GFAP, Iba1 and NeuN) at the same concentrations used for the immune serum and immune IgG exhibited only low levels of background fluorescence. Micrographs are representative of at least 3 images of the superficial layers of dorsal horn (L4-L6) from 3 different animals performed on different days.

FIG. 3. Therapeutic manipulation with inhibitors of ceramide biosynthesis blocks hyperalgesia and antinociceptive tolerance. The development of morphine-induced thermal hyperalgesia (B), antinociceptive tolerance (C), and associated increased S1P levels (A) in dorsal horn tissues is attenuated by intrathecal delivery of inhibitors of the de novo (Myr, 0.3 μM/day/6 days; FB1,] μM/day/6 days) and sphingomyelin (D609, 1 μM/day/6 days) pathways. Results are expressed as mean±SEM for n=5 animals and analyzed by ANOVA with Dunnett's post hoc test where *$P<0.001$ for Veh-Mor vs Veh-Sal and † $P<0.001$ for Drugs-Mor vs Veh-Mor.

FIG. 4. DMS blocks glial cell activation and increased spinal production of cytokines. When compared to Veh-Sal, the development of tolerance (Veh-Mor) was associated with significant activation of astrocytes and microglial cells as evidenced, respectively, by increased GFAP (A, A1) and Iba1 (B, B1) protein expression and increased formation of TNF-α (C), IL-1β (D) and IL-6 (E) levels in dorsal horn tissues. Co-administration of morphine with DMS (0.3 μM/day/6 days) prevented glial cell activation (A, A1, B, B1) and increased cytokine formation (C-E). Composite densitometric analyses for gels of 5 rats are expressed as mean±SEM of % β-actin as shown in A1 and B1. Results are expressed as mean±SEM for n=5 animals and analyzed by ANOVA with Dunnett's hoc test where *$P<0.001$ for Veh-Mor vs Veh-Sal and † $P<0.01$ or †† $P<0.001$ for DMS-Mol vs Veh-Mor.

FIG. 5. DMS blocks post-translation protein nitration in spinal cord. When compared to Veh-Sal, the development of tolerance (Veh-Mor) was associated with significant protein nitration as detected by immunohistochemistry (B, see arrows) in particular significant nitration of the glutamate transporter (GLT-1, D, D1) and of GS (E, E1). These events were attenuated by co-administration of morphine with DMS (0.3 μM/day/6 days, D and E). Gels shown in D and E are representative of gels from n=5 rats. Composite densitometric analyses for gels of nitrated proteins of 5 rats are expressed as mean±SEM of % B-actin as shown in D1 and E1 and analyzed by ANOVA with Dunnett's pos hoc test where *$P<0.001$ for Veh-Mor vs Veh-Sal and † $P<0.001$ for DMS-Mor vs Veh-Mor. Micrographs are representative of at least 5 from different animals performed on different days and are taken from the superficial layers of the dorsal horn (L4-L6), the anatomical site which stains for NT during tolerance (Muscoli et al., 2007).

FIG. 6. Proposed working hypothesis. Chronic administration of morphine activates the ceramide metabolic pathway resulting in increased formation of S1P in glial cells upon activation of sphingosine kinase (SphK) 1 and 2. Following its extracellular release, S1P binds S1P receptors (which remain to be identified) on glial cells initiating a series of events culminating in enhanced production of pro-inflammatory cytokines and peroxynitrite (PN)-mediated nitration of glutamate transporters (GTs) and glutamine synthetases (GS). Activation of glial TLR4 may provide a link between chronic administration of morphine and activation of the ceramide metabolic pathway in the development of morphine-induced hyperalgesia and antinociceptive tolerance.

FIG. 7. Targeting ceramide blocks the development of paclitaxel-induced mechano-allodynia.

FIG. 8. Targeting ceramide in the spinal cord blocks the development of paclitaxel induced mechano-allodynia and increased production of proinflammatory cytokines.

FIG. 9. Control, Taxol, Taxol plus drug (top, middle, bottom rows). Ceramide (left column—red), astrocytes (middle column—green), merged image (right column).

FIG. 10. The S1P1 receptor antagonist W146 reverses Paclitaxel-induced neuropathic pain. W146 was given i.p on day 16 and behavioral testing was performed 60 minutes later.

FIG. 11. S1P induces peripheral sensitization and hyperalgesia through the S1P1 receptor. Intraplantar injection of the S1P1 antagonist W146 was given 15 minutes before intraplantar injection of S1P blocked the development of thermal hyperalgesia. * $P<0.05$ vs. Veh, † $P<0.001$ vs. S1P.

FIG. 12. Effect of SK-I (a sphingosine kinase inhibitor) on the development of carrageenan-induced thermal hyperalgesia. An intraplantar injection of carrageenan (1%, ○) led to a time-dependent development of thermal hyperalgesia that was attenuated in a dose-dependent manner by intraplantar SK-I given at 250 ng (●), 500 ng (■), or 1000 ng (▲). Results are expressed as mean±SEM for 5 rats and analyzed by two-way repeated measures ANOVA with Bonferroni post hoc test where ***$P<0.001$ vs. carrageenan.

FIG. 13. The sphingosine kinase inhibitor SK-I blocks carrageenan-induced inflammation. Drug given by intraplantar injection 15 min before carrageenan.

FIG. 14. The S1P1 receptor antagonist W146 blocks carrageenan-induced hyperalgesia.

FIG. 15. Inhibition of morphine-induced antinociceptive tolerance by inhibitors of the ceramide metabolic pathway. When compared to rats that received a chronic s.c infusion of saline (Veh-Sal, n=5, ●) over 7 days, infusion of morphine over the same time frame (Veh-Mor, n=5, ■) led to the development of (A) antinociceptive tolerance as evidenced by the inhibition of increased tail-flick latencies at on day 3 and 6 over corresponding baselines prior to acute morphine (n=5, Veh-Sal, ○; Veh-Mor, □; DMS, Δ; and SK-I, ◇); events that were blocked over time by co-administration of morphine with DMS (0.3 μM/day/6 days, n=5, ▲) or SK-I (0.3 μM/day/6 days, n=5, ◆). Results in B show dose-dependent inhibition of tolerance (Veh-Mor, gray bar vs Veh-Sal, white bar, with respect to corresponding baseline values, stipled bars) at time of peak tolerance (day 6) with DMS (black bar) and SK-I (hashed bar) while results in C show inhibition of tolerance on day 6 with inhibitors of the de novo (Myr, 0.3 μM/day/6 days; FB1, 1 μM/day/6 days, black bars) and sphingomyelin (D609, 1 μM/day/6 days black bar) pathways with respect to corresponding baseline values (stipled bars). Results are expressed as mean±SEM for n=5 animals for Tail Flick Latency (s) and analyzed by ANOYA with Dunnett's post hoc test where *$P<0.001$ for Veh-Mor vs Veh-Sal, §$P<0.001$ vs t=0 h, and † $P<0.001$ for time-matched Drug-Mor vs Veh-Mor.

FIG. 16. Photomontage of the whole spinal cord stained with ceramide. Fixed frozen spinal cord sections from the lumbar portion (L4-L6) of Veh-Sal (A) and Veh-Mor (B) rats were stained for ceramide (red). When compared to Veh-Sal animals (A) significant increase in ceramide immunofluorescence was observed on the superficial layers of the spinal cord of Veh-Mor animals (B). Negative controls using normal rabbit serum were both negative with only low level background fluorescence (not shown). Micrographs are representative of at least 3 images of 3 different animals performed on different days.

FIG. 17. Co-localization of ceramide with activated astrocytes. Fixed frozen spinal cord sections from Veh-Sal (A-C) and Veh-Mor (D-F) rats were stained for ceramide (red, A, D) or astrocytes (GFAP+, green, B, E). When compared to Veh-Sal animals, ceramide and GFAP immunofluorescence increased in Veh-Mor rats (compare D to A and E to B). Furthermore, and as shown in the merged images in C and F, ceramide levels co-localized (yellow) with astrocytes in Veh-Mor animals. Negative controls using normal rabbit serum (for ceramide) or normal mouse IgG (for GFAP) at the same concentrations as for the immune serum and immune IgG exhibited only low levels of background fluorescence. Micrographs are representative of at least 3 images of the superficial layers of dorsal horn (L4-L6) from 3 different animals performed on different days.

FIG. 18. Co-localization of ceramide with activated microglia. Fixed frozen spinal cord sections from Veh-Sal (A-C) and Veh-Mor (D-F) rats were stained for ceramide (red, A, D) or microglia cells (Iba1+, green, μM/day/6 days). When compared to Veh-Sal animals, ceramide and Iba1 immunofluorescence increased in Veh-Mor rats (compare D to A and E to B). Furthermore, and as shown in the merged images in C and F, ceramide levels co-localized (yellow) with microglial cells in Veh-Mor animals. Negative controls using normal rabbit serum (for ceramide) or normal mouse IgG (for Iba1) at the same concentrations as for the immune serum and immune IgG exhibited only low levels of background fluorescence. Micrographs are representative of at least 3 images of the superficial layers of dorsal horn (L4L6) from 3 different animals performed on different days.

FIG. 19. Ceramide does not co-localize with neurons. Fixed frozen spinal cord sections from Veh-Sal (A-C) and Veh-Mor (D-F) rats were stained for ceramide (red, A, D) or neurons (NeuN+, green. B, E). As shown in the merged images in C and F, ceramide levels did not co-localize (lack of yellow) with neurons in Veh-Mor animals. Negative controls using normal rabbit serum (for ceramide) or normal mouse IgG (for NeuN) at the same concentrations as for the immune serum and immune IgG exhibited only low levels of background fluorescence. Micrographs are representative of at least 3 images of the superficial layers of dorsal horn (L4-L6) from 3 different animals performed on different days.

FIG. 20. The role of S1P1 receptor in the development of CIPN. When compared to the vehicle group (Δ), administration of paclitaxel (○) led to a time-dependent development of mechano-allodynia (A) or mechano-hyperalgesia (B). Daily s.c injections (from day 0 to 15) with the S1P1-specific antagonist, W146, (0.3, ▲; 1, ▼; and 3 μM/d, ■), but not its inactive enantiomer, W140 (3 μM/d, ◇ ), blocked the development of mechano-allodynia (A) and mechano-hyperalgesia (B). Wh en given alone, W146 (3 μM/d, □) did not affect withdrawal thresholds in vehicle groups. Results are expressed as mean±SEM, n=6. Behavioral data were analyzed by two-tailed, two-way ANOVA with Bonferroni post hoc comparisons. ***$P<0.001$ for paclitaxel vs vehicle and ††† $P<0.001$ for paclitaxel vs paclitaxel+W146.

FIG. 21. The development of paclitaxel-induced neuropathic pain is associated with increased spinal levels of ceramide, a precursor in the biosynthesis of S1P. When compared to vehicle (Veh,▲), administration of paclitaxel (P,■) enhances serine palmytoyl transferases (SPT, A, n=5) and acid sphingomyelinases (aSMase, B, n=4) activities leading to increased production of ceramide (C,D; red; n=3) and its bioactive derivative, sphingosine 1-phosphate (S1P, E, n=6), in the spinal cord on D16. For immunofluorescence imaging (C,D), negative controls using normal rabbit serum for ceramide exhibited only low levels of background fluorescence. Micrographs are representative of at least 3 images of the superficial layers of dorsal horn (L4-L6) from 3 different animals performed on different days. Results are expressed as mean±SEM for (n) animals and analyzed by Student's t-test. *$P<0.05$; ***$P<0.001$ for paclitaxel vs vehicle.

FIG. 22. The development of paclitaxel-induced neuropathic pain is associated with increased ceramide production in astrocytes. Fixed frozen spinal cord sections from vehicle (Veh; A, C, E) and paclitaxel-treated (P; B, D, F) were stained for ceramide (NT; red; A, B) and GFAP (green; C, D) for astrocytes.

FIG. 23. Fingolimod, a potent S1P receptor agonist that down-regulates S1P receptor surface expression attenuated the development of CIPN. When compared to the vehicle group (Δ), administration of paclitaxel (○) led to a time-dependent development of mechano-allodynia (A) or mechano-hyperalgesia (B). Daily s.c injections (from day 0 to 15) with Fingolimod (0.01 mg/kg/d, ▲) blocked the development of mechano-allodynia (A) and mechano-hyperalgesia (B). When given alone, Fingolimod (3 μM/d, □) did not affect withdrawal thresholds in vehicle groups. Results are expressed as mean±SEM, n=6. Behavioral data were analyzed by two-tailed, two-way ANOVA with Bonferroni post hoc comparisons. ***$P<0.001$ for paclitaxel vs vehicle and ††† $P<0.001$ for paclitaxel vs paclitaxel+Fingolimod.

FIG. 24. Fingolimod, a potent S1P receptor agonist that down-regulates S1P receptor surface expression attenuated the development of CIPN. When compared to the Vehicle group, Oxaliplatin-treatment led to the development of mechano-allodynia (A) and mechano-hyperalgesia (B). Daily subcutaneous injections (day 0-17) of Fingolimod significantly attenuated the development of oxaliplatin-induced mechano-hypersensitivity (A, B). Furthermore, after the cessation of treatment with Fingolimod on day 17, mechano-hypersensitivity failed to develop. *$P<0.001$ vs Vehicle; † $P<0.001$, vs Oxaliplatin; two-way ANOVA with Bonferroni post hoc comparisons. Results are expressed as mean±SEM for 2 rats.

FIG. 25. Morphine-induced hyperalgesia and tolerance is blocked by the selective S1P1 receptor antagonist, W146. When compared to rats that received a chronic s.c infusion of saline (Veh-Sal, A) over 7 days, infusion of morphine over the same time frame (Veh-Mor, ○) led to a time-dependent development of thermal hyperalgesia (B) and antinociceptive tolerance (B), events blocked in a dose-dependent manner by co-administration of morphine with W146 (0.3, ▲; 1, ▼; and 3 μM/day/5 days, ■); but not with the inactive enantiomer, W140 (3 μM/day/5 days, ♦). When given alone to rats that received a chronic s.c infusion of saline, W146 (3 μM/day/5 days, □) and W140 (3 μM/day/5 days, □) did not modify paw withdrawal latencies or tail flick responses in vehicle groups. Results are expressed as mean ±SEM; n=5 rats. Behavioral data were analyzed by two-tailed, two-way ANOVA with Bonferroni post hoc comparisons. ***$P<0.001$ vs. Veh-Sal and † $P<0.05$, †† $P<0.01$, ††† $P<0.001$ vs. Veh-Mor.

FIG. 26. The selective S1P1 receptor antagonist, W146, does not potentiate antinociceptive responses to acute morphine. The antinociceptive effects of morphine (1-6 mg/kg, open bar) are not affected by i.th injection of W146 (1 μM, given 15 min before, black bar). Tail Flick Latency (s) assessed 30 min post-i.p injection of morphine. Results are expressed as mean±SEM; n=3 rats. Data were analyzed by two-tailed, two-way ANOVA with Bonferroni post hoc comparisons.

FIG. 27. Carrageenan induced thermal hyperalgesia is blocked by Fingolimod. When compared to vehicle (Veh, ○), intraplantar injection of carrageenan (1%, ●) induces a time-dependant increase in thermal hyperalgesia by 0.5 h that continues through 2 h. These events are blocked by FTY720 (1 mg/kg, ■) when given orally 90 min before carrageenan (BL). Means±SEM, n=4, two-tailed two-way repeated measures ANOVA with Bonferroni post hoc comparisons to carrageenan. ***$P<0.001$ vs. Veh and ††† $P<0.001$ vs carrageenan.

FIG. 28. Role of the S1P to S1P1 receptor pathway in ceramide-induced hyperalgesia. (A) When compared to rats administered intraplantar LT1002 or LT1017 vehicle and ceramide vehicle (Veh, Δ, n=3), an intraplantar injection of ceramide (10 g, ♦, n=3) led to a time-dependent development of thermal hyperalgesia that was attenuated by the anti-S1P antibody LT1002 (242 μg, ●, n=3), but not by LT1017 (286 μg, ■, n=3). Given alone, LT1002 (○, n=3) and LT1017 (□, n=3) had no effect. (B) When compared to rats administered intraplantar W146 or W140 vehicle and ceramide vehicle (Veh, A, n=4), an intraplantar injection of ceramide (10 μg, ◇, n=4) led to a time-dependent development of thermal hyperalgesia that was inhibited by the S1P1 receptor antagonist, W146, at 0.3 μg (●, n=4), 0.6 μg (■, n=4), or 1.2 μg, n=4), but not by W140 (1.2 μg, □, n=4). Given alone, W146 (○, n=4) had no effect. Results are expressed as mean±SEM for (n) rats and analyzed by ANOVA with Bonferroni post hoc test where *$P<0.001$ vs. Veh and † $P<0.001$ vs. Cer. See also Doyle et al., Neuroscience Letters 499 (2011) 4-8, incorporated herein by reference.

ABBREVIATIONS AND DEFINITIONS

Figure 1A:
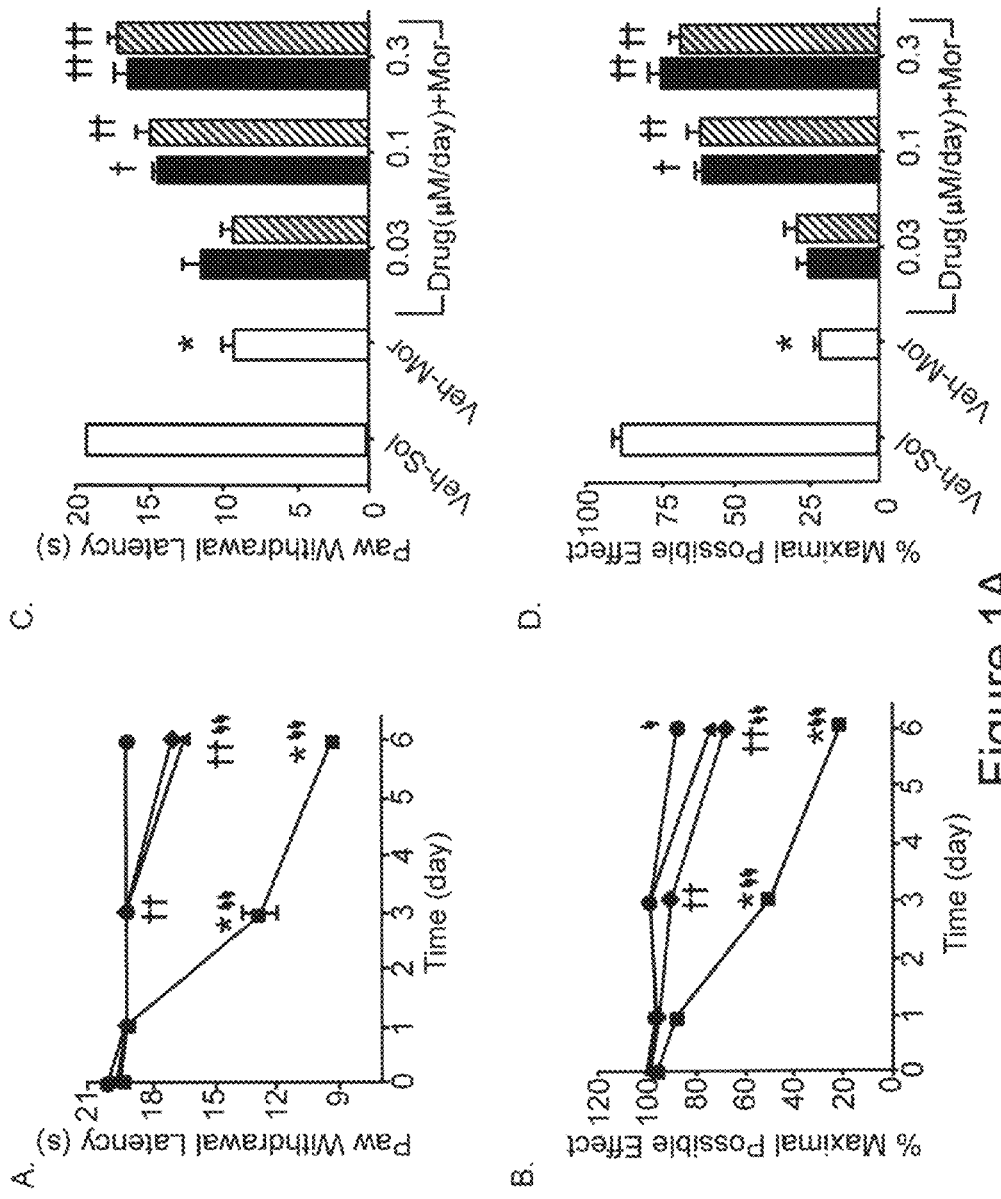

To facilitate understanding of the invention, a number of terms and abbreviations as used herein are defined below as follows:

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')2, Fv), single chain (ScFv), mutants thereof, fusion proteins comprising an antibody portion, and any other modified configuration of the immunoglobulin molecule that comprises an antigen recognition site. An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

"Fv" is an antibody fragment that contains a complete antigen-recognition and binding site. In a two-chain Fv species, this region consists of a dimer of one heavy and one light chain variable domain in tight, non-covalent association. In a single-chain Fv species, one heavy and one light chain variable domain can be covalently linked by a flexible peptide linker such that the light and heavy chains can associate in a dimeric structure analogous to that in a two-chain Fv species. It is in this configuration that the three CDRs of each variable domain interact to define an antigen-binding specificity on the surface of the VH-VL dimer. However, even a single variable domain (or half of an Fv comprising only 3 CDRs specific for an antigen) has the ability to recognize and bind antigen, although generally at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge regions.

A "monoclonal antibody" refers to a homogeneous antibody population wherein the monoclonal antibody is comprised of amino acids (naturally occurring and non-naturally occurring) that are involved in the selective binding of an antigen. A population of monoclonal antibodies is highly specific, being directed against a single antigenic site. The term "monoclonal antibody" encompasses not only intact monoclonal antibodies and full-length monoclonal antibodies, but also fragments thereof (such as Fab, Fab', F(ab')2, Fv), single chain (ScFv), mutants thereof, fusion proteins comprising an antibody portion, and any other modified configuration of the immunoglobulin molecule that comprises an antigen recognition site of the required specificity and the ability to bind to an antigen. It is not intended to be limited with regard to the source of the antibody or the manner in which it is made (e.g., by hybridoma, phage selection, recombinant expression, transgenic animals, etc.).

As used herein, "human antibody" means an antibody having an amino acid sequence corresponding to that of an antibody produced by a human and has been made using any of the techniques for making human antibodies known in the art. This definition of a human antibody includes antibodies comprising at least one human heavy chain polypeptide or at least one human light chain polypeptide. One such example is an antibody comprising murine light chain and human heavy chain polypeptides. Human antibodies can be produced using various techniques known in the art. In one aspect, the human antibody is selected from a phage library, where that phage library expresses human antibodies (Vaughan et al., 1996, Nature Biotechnology, 14:309-314; Sheets et al., 1998, PNAS, (USA) 95:6157-6162; Hoogenboom and Winter, 1991, J. Mol. Biol., 227:381; Marks et al., 1991, J. Mol. Biol., 222:581). Human antibodies can also be made by introducing human immunoglobulin loci into transgenic animals, e.g., mice in which the endogenous immunoglobulin genes have been partially or completely inactivated. This approach is described in U.S. Pat. Nos. 5,545,807; 5,545,806; 5,569,825; 5,625,126; 5,633,425; and 5,661,016. Alternatively, the human antibody may be prepared by immortalizing human B lymphocytes that produce an antibody directed against a target antigen (such B lymphocytes may be recovered from an individual or may have been immunized in vitro). See, e.g., Cole et al., Monoclonal Antibodies and Cancer Therapy, Alan R. Liss, p. 77 (1985); Boerner et al., 1991, J. Immunol., 147 (1):86-95; and U.S. Pat. No. 5,750,373.

"Chimeric antibodies" refers to those antibodies wherein one portion of each of the amino acid sequences of heavy and light chains is homologous to corresponding sequences in antibodies derived from a particular species or belonging to a particular class, while the remaining segment of the chains is homologous to corresponding sequences in another. Typically, in these chimeric antibodies, the variable region of both light and heavy chains mimics the variable regions of antibodies derived from one species of mammals, while the constant portions are homologous to the sequences in antibodies derived from another. One clear advantage to such chimeric forms is that, for example, the variable regions can conveniently be derived from presently known sources using readily available hybridomas or B cells from non human host organisms in combination with constant regions derived from, for example, human cell preparations. While the variable region has the advantage of ease of preparation, and the specificity is not affected by its source, the constant region being human, is less likely to elicit an immune response from a human subject when the antibodies are injected than would the constant region from a non-human source. However, the definition is not limited to this particular example.

A "functional Fc region" possesses at least one effector function of a native sequence Fc region. Exemplary "effector functions" include C1q binding; complement dependent cytotoxicity (CDC); Fc receptor binding; antibody-dependent cell-mediated cytotoxicity (ADCC); phagocytosis; down-regulation of cell surface receptors (e.g. B cell receptor; BCR), etc. Such effector functions generally require the Fc region to be combined with a binding domain (e.g. an antibody variable domain) and can be assessed using various assays known in the art for evaluating such antibody effector functions.

A "native sequence Fc region" comprises an amino acid sequence identical to the amino acid sequence of an Fc region found in nature. A "variant Fc region" comprises an amino acid sequence which differs from that of a native sequence Fc region by virtue of at least one amino acid modification, yet retains at least one effector function of the native sequence Fc region. Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% sequence identity with a native sequence Fc region and with an Fc region of a parent polypeptide, and most preferably at least about 90% sequence identity therewith, more preferably at least about 95% sequence identity therewith.

As used herein "antibody-dependent cell-mediated cytotoxicity" and "ADCC" refer to a cell-mediated reaction in which nonspecific cytotoxic cells that express Fc receptors (FcRs) (e.g. natural killer (NK) cells, neutrophils, and macrophages) recognize bound antibody on a target cell and subsequently cause lysis of the target cell. ADCC activity of a molecule of interest can be assessed using an in vitro ADCC assay, such as that described in U.S. Pat. No. 5,500,362 or 5,821,337. Useful effector cells for such assays include peripheral blood mononuclear cells (PBMC) and NK cells. Alternatively, or additionally, ADCC activity of the molecule of interest may be assessed in vivo, e.g., in an animal model such as that disclosed in Clynes et al., 1998, PNAS (USA), 95:652-656.

As used herein, "Fc receptor" and "FcR" describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, 1991, Ann. Rev. Immunol., 9:457-92; Capel et al., 1994, Immunomethods, 4:25-34; and de Haas et al., 1995, J. Lab. Clin. Med., 126:330-41. "FcR" also includes the neonatal receptor, FcRn, which is responsible for the transfer of maternal IgGs to the fetus (Guyer et al., 1976, J. Immunol., 117:587; and Kim et al., 1994, J. Immunol., 24:249).

"Complement dependent cytotoxicity" and "CDC" refer to the lysing of a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., J. Immunol. Methods, 202: 163 (1996), may be performed.

Figure 29:
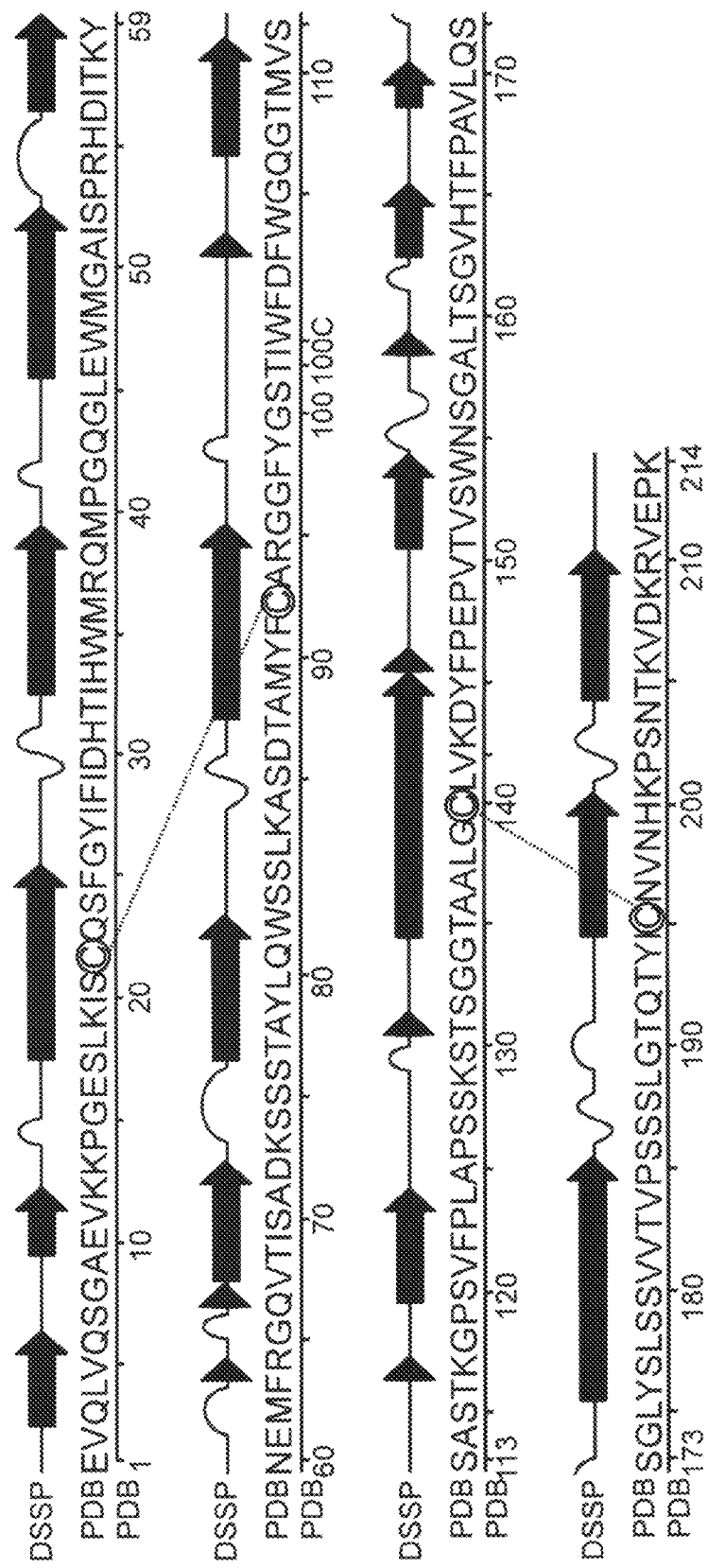
FIG. 29 illustrates the heavy chain variable region of antibody LT1009 (SEQ ID NO: 1).
Figure 30:
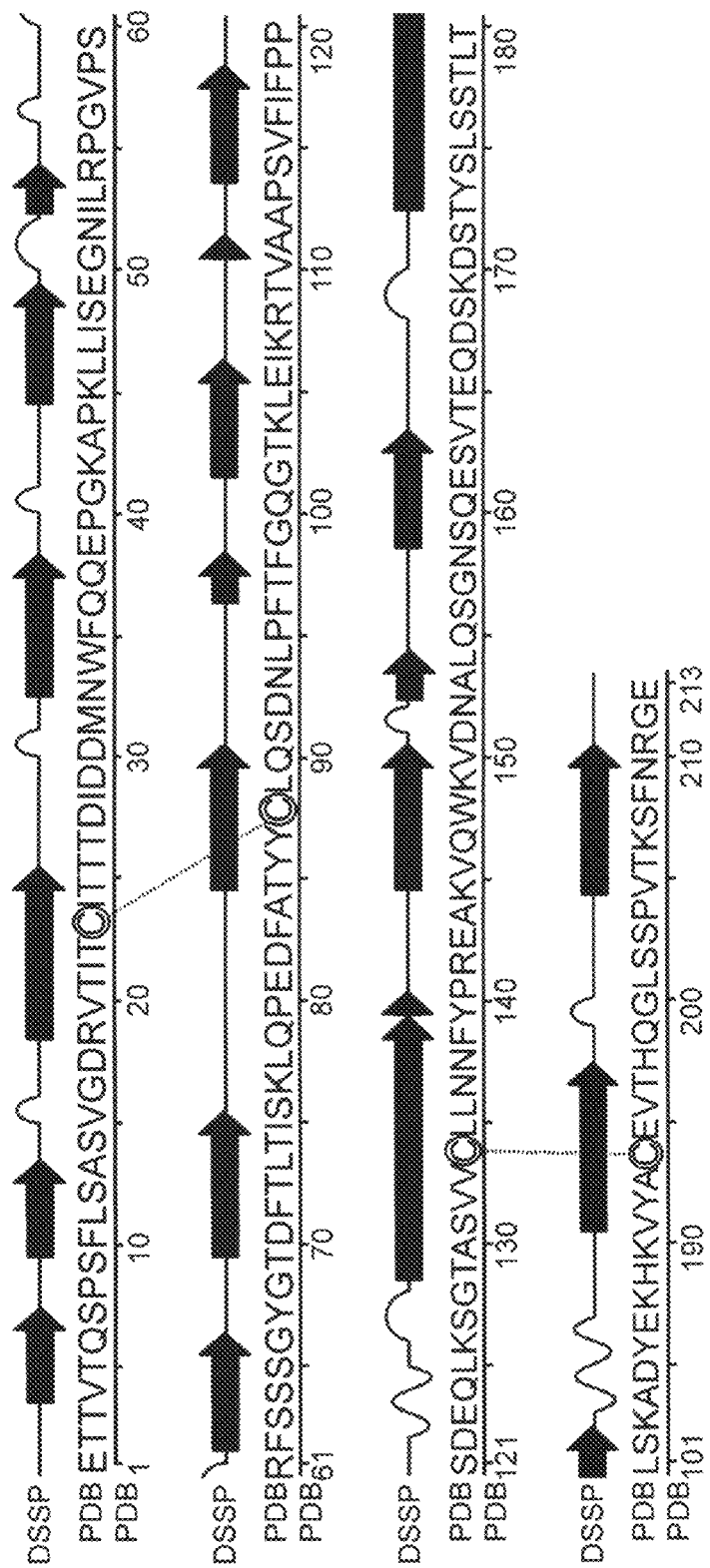
FIG. 30 illustrates the light chain variable region of antibody LT1009 (SEQ ID NO: 2).

As used herein, the term "LT1009" refers to an antibody comprising the amino acid sequence of the heavy chain (SEQ ID NO:1) and light chain (SEQ ID NO:2) variable regions shown in FIGS. 29 and 30, respectively. The CDR portions of LT1009 are also diagrammatically depicted in FIGS. 29 and 30. The generation and characterization of LT1009 is described in U.S. Pat. No. 7,829,674 and corresponding PCT application PCT/US2007/082647.

As used herein, "immunospecific" binding of antibodies refers to the antigen specific binding interaction that occurs between the antigen-combining site of an antibody and the specific antigen recognized by that antibody (i.e., the antibody reacts with the protein in an ELISA or other immunoassay, and does not react detectably with unrelated proteins).

An epitope that "specifically binds", or "preferentially binds" (used interchangeably herein) to an antibody or a polypeptide is a term well understood in the art, and methods to determine such specific or preferential binding are also well known in the art. A molecule is said to exhibit "specific binding" or "preferential binding" if it reacts or associates more frequently, more rapidly, with greater duration and with greater affinity with a particular cell or substance than it does with alternative cells or substances. An antibody "specifically binds" or "preferentially binds" to a target if it binds with greater affinity, avidity, more readily, and with greater duration than it binds to other substances. For example, an antibody that specifically or preferentially binds to S1P is an antibody that binds this molecule with greater affinity, avidity, more readily, and with greater duration than it binds to other molecules. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

The terms "polypeptide", "oligopeptide", "peptide" and "protein" are used interchangeably herein to refer to polymers of amino acids of any length. The polymer may be linear or branched, it may comprise modified amino acids, and it may be interrupted by nonamino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, non-naturally occurring amino acids, etc.), as well as other modifications known in the art. It is understood that, because the polypeptides of this invention are based upon an antibody, the polypeptides can occur as single chains or associated chains.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and their analogs, or any substrate that can be incorporated into a polymer by a polymerase, including any suitable DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-0-methyl-, 2'-0-allyl, 2'-fluoro- or T-azido-ribose, carbocyclic sugar analogs, anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, aspects wherein phosphate is replaced by P(O)S ("thioate"), P(S)S ("dithioate"), "(O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Chothia et al. (1989) Nature 342:877; Al-lazikani et al (1997) J. Molec. Biol. 273:927-948)). As used herein, a CDR may refer to CDRs defined by either approach or by a combination of both approaches.

A "constant region" of an antibody refers to the constant region of the antibody light chain or the constant region of the antibody heavy chain, either alone or in combination.

As used herein, the term "S1P" refers to Sphingosine-1-Phosphate.

An "S1P receptor," also referred to as "S1PR" refers to a polypeptide that is bound by or activated by S1P. S1P receptors include those of any mammalian species, including, but not limited to, human, canine, feline, equine, primate, or bovine. This definition includes S1P receptor subtypes S1P1, S1P2, S1P3, S1P4 and S1P5, also known as S1PR$_1$, S1PR$_2$, S1PR$_3$, S1PR$_4$, and S1PR$_5$, respectively.

As used herein, an "anti-S1P antibody" refers to an antibody which is able to bind to S1P and inhibit S1P biological activity and downstream pathway(s) mediated by S1P signaling or secondary messenger activity. Anti-S1P antibodies encompass antibodies that block, antagonize, suppress or reduce (including significantly) S1P biological activity, including downstream pathways mediated by S1P signaling, such as receptor binding and elicitation of a cellular response to S1P. For purpose of the present invention, it will be explicitly understood that the term "anti-S1P antibody" encompasses all the previously identified terms, titles, and functional states and characteristics whereby the S1P itself, an S1P biological activity (including but not limited to its ability to mediate any aspect of neuropathic pain), or the consequences of the biological activity, are substantially nullified, decreased, or neutralized in any degree. In some aspects, an anti-S1P antibody binds S1P and prevent S1P dimerization and binding to an S1P receptor, such as S1P1 receptor. In other aspects, an anti-S1P antibody binds S1P and prevents S1P receptor dimerization and S1P phosphorylation. Examples of anti-S1P antibodies include LT1009.

As used herein, an "anti-S1P receptor antibody" refers to an antibody which is able to bind to an S1P receptor and inhibit S1P receptor biological activity. Anti-S1P receptor antibodies encompass antibodies that block, antagonize, suppress or reduce (including significantly) S1P receptor biological activity such as binding and elicitation of a cellular response in conjunction with S1P. For purpose of the present invention, it will be explicitly understood that the term "anti-S1P receptor antibody" encompasses all the previously identified terms, titles, and functional states and characteristics whereby the S1P receptor itself, an S1P receptor biological activity (including but not limited to its ability to ability to mediate any aspect of neuropathic pain), or the consequences of the biological activity, are substantially nullified, decreased, or neutralized in any degree. In some aspects, an anti-S1P receptor antibody binds S1P receptor and prevents S1P dimerization and binding to S1P. In other aspects, an anti-S1P receptor antibody binds an S1P receptor and prevents S1P phosphorylation.

As used herein, "S1P receptor antagonists" include, but are not limited to, anti-S1P antibodies and anti-S1P1 receptor antibodies.

Reference to "sphingosine kinase" should be understood as a reference to the molecule which is, inter alia, involved in the generation of sphingosine-1-phosphate during the activation of the sphingosine kinase signaling pathway. Methods of detecting sphingosine kinase antagonist activity include those disclosed in U.S. Pat. No. 7,172,879 and in PCT Patent Application No. PCT/AU98/00730 (WO 99/12533), which are incorporated herein by reference in their entirety.

"Biological activity" of S1P generally refers to the ability to bind S1P receptors and activate S1P receptor signaling pathways, including but not limited to S1P1 receptor signaling pathways. Without limitation, a biological activity includes any one or more of the following: the ability to bind an S1P receptor; the ability to promote S1P receptor dimerization and phosphorylation; the ability to activate an S1P receptor signaling pathway; and the ability to mediate neuropathic pain and hyperalgesia, including cancer and chemotherapy-induced pain.

As used herein, "substantiality pure" refers to material which is at least 50% pure (i.e., free from contaminants), more preferably at least 90% pure, more preferably at least 95% pure, more preferably at least 98% pure, more preferably at least 99% pure.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As used herein, "treatment" is an approach for obtaining beneficial or desired clinical results. For purposes of this invention, beneficial or desired clinical results include, but are not limited to, one or more of the following: improvement or alleviation of any aspect of pain, including neuropathic, hyperalgesia, allodynia, inflammatory pain, cancer pain, or chemotherapy-induced pain. For purposes of this invention, beneficial or desired clinical results include, but are not limited to, one or more of the following: including lessening severity, alleviation of one or more symptoms associated with neuropathic pain including any aspect of neuropathic pain (such as shortening duration of neuropathic pain, reduction of neuropathic pain sensitivity or sensation); lessening severity, alleviation of one or more symptoms associated with inflammatory pain including any aspect of inflammatory pain (such as shortening duration of inflammatory pain, reduction of inflammatory pain sensitivity or sensation), and lessening severity, alleviation of one or more symptoms associated with hyperalgesia and allodynia including any aspect of hypersensitivity, including hyperalgesia and allodynia.

An "effective amount" of drug, compound, or pharmaceutical composition is an amount sufficient to effect beneficial or desired results including clinical results such as alleviation or reduction in neuropathic pain sensation. An effective amount can be administered in one or more administrations. For purposes of this invention, an effective amount of drug, compound, or pharmaceutical composition is an amount sufficient to treat, ameliorate, reduce the intensity of and prevent neuropathic pain, including cancer pain and chemotherapy-induced pain, inflammatory pain, and hypersensitivity. As is understood in the clinical context, an effective amount of a drug, compound, or pharmaceutical composition may or may not be achieved when administered in conjunction with another drug, compound, or pharmaceutical composition including other currently used compounds such as antidepressants, anticonvulsive, NSAIDs, COX-2 inhibitors, NOS inhibitors and so forth. Thus, an "effective amount" may be considered in the context of administering one or more therapeutic agents, and a single agent may be considered to be given in an effective amount if, in conjunction with one or more other agents, a desirable result may be or is achieved.

"Reducing incidence" of pain means any of reducing severity (which can include reducing need for and amount of (e.g., exposure to) other drugs and therapies generally used for these conditions, including, for example, opiates), duration, and frequency (including, for example, delaying or increasing time to neuropathic pain in an individual). As is understood by those skilled in the art, individuals may vary in terms of their response to treatment, and, as such, for example, a "method of reducing incidence of neuropathic pain in an individual" reflects administering the sphingosine kinase antagonist, S1P antagonist, or S1P receptor antagonist, including but not limited to an anti-S1P antibody or anti-S1P1 receptor antibody, based on a reasonable expectation that such administration may likely cause such a reduction in incidence in that particular individual.

"Ameliorating" a neuropathic pain or one or more symptoms of a neuropathic pain (such as cancer pain or chemotherapy-induced pain) means a lessening or improvement of one or more symptoms of a neuropathic pain as compared to not administering a sphingosine kinase antagonist, S1P antagonist, S1P receptor agonist, or S1P receptor antagonist, including but not limited to an antiS1P antibody or anti-S1P1 receptor antibody. "Ameliorating" also includes shortening or reduction in duration of a symptom.

"Palliating" a neuropathic pain or one or more symptoms of a neuropathic pain (such as cancer pain or chemotherapy-induced pain) means lessening the extent of one or more undesirable clinical manifestations of neuropathic pain in an individual or population of individuals treated with a sphingosine kinase antagonist, S1P antagonist, S1P receptor agonist, or S1P receptor antagonist, including but not limited to an anti-S1P antibody or anti-S1P1 receptor antibody, in accordance with the invention.

As used therein, "delaying" the development of pain means to defer, hinder, slow, retard, stabilize, and postpone progression of pain, for example neuropathic pain such as cancer pain or chemotherapy-induced pain. This delay can be of varying lengths of time, depending on the history of the disease and individuals being treated. As is evident to one skilled in me art, a sufficient or significant delay can, in effect, encompass prevention, in that the individual does not develop neuropathic pain. A method that "delays" development of the symptom is a method that reduces probability of developing the symptom in a given time frame and reduces extent of the symptoms in a given time frame, when compared to not using the method. Such comparisons are typically based on clinical studies, using a statistically significant number of subjects.

"Neuropathic pain" as used herein refers to pain of any etiology, and any pain associated with damage to or dysfunction of the peripheral nervous system and the central nervous system. Examples of neuropathic pain include the direct result of cancer on peripheral nerves (e.g., compression by a tumor), or as a side effect of chemotherapy (i.e. with Paclitaxel, platinum drugs), radiation injury, cancer surgery, pain associated with cancer associated with the nervous system (including "break-through pain" and pain associated with terminal cancer), peripheral neuropathy post-herpetic neuralgia, and diabetes.

"Inflammatory pain" as used herein refers to acute or chronic pain associated with, for example, edema swelling and inflammation of a tissue or a joint.

"Hypersensitivity" or "pain-hypersensitivity" as used herein includes hyperalgesia and allodynia (thermal/tactile/mechanical) typically associated with pain states of various etiologies.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides, or embedding in a semi-solid or solid matrix for sectioning purposes. The term "biological sample" encompasses a clinical sample, and also includes cells in culture, cell supernatants, cell lysates, serum, plasma, biological fluid, and tissue samples.

An "individual" is a vertebrate, preferably a mammal, more preferably a human. Mammals include, but are not limited to, farm animals (such as cows), sport animals, pets (such as cats, dogs and horses), primates, mice and rats.

As used herein, "vector" means a construct, which is capable of delivering, and preferably expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, "pharmaceutically acceptable carrier" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline. Compositions comprising such carriers are formulated by well known conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000).

The term "$K_{off}$", as used herein, is intended to refer to the off rate constant for dissociation of an antibody from the antibody/antigen complex.

The term "$K_d$", as used herein, is intended to refer to the dissociation constant of an antibody-antigen interaction.

SUMMARY OF THE INVENTION

In a first aspect, the invention disclosed herein provides methods for treating neuropathic pain in an individual by administration of a therapeutically effective amount of at least one of a sphingosine kinase antagonist, S1P antagonist, S1P receptor agonist, or S1P receptor antagonist.

In a second aspect, the invention disclosed herein provides methods for treating inflammatory pain in an individual by administration of a therapeutically effective amount of at least one of a sphingosine kinase antagonist, S1P antagonist, S1P receptor agonist, or S1P receptor antagonist.

In a third aspect, the invention disclosed herein also provides methods for treating hypersensitivity, including, as defined above, hyperalgesia and allodynia, in an individual by administration of a therapeutically effective amount of at least one of a sphingosine kinase antagonist, S1P antagonist, S1P receptor agonist, or S1P receptor antagonist.

In a fourth aspect, the invention disclosed herein also provides methods for treating antinociceptive tolerance, in an individual by administration of a therapeutically effective amount of at least one of a sphingosine kinase antagonist, S1P antagonist, S1P receptor agonist, or S1P receptor antagonist.

In a fifth aspect, the invention disclosed herein further provides a kit comprising an effective amount of at least one of a sphingosine kinase antagonist, S1P antagonist, S1P receptor agonist, or S1P receptor antagonist and instructions for administering an effective amount of the at least one of sphingosine kinase antagonist, S1P antagonist, S1P receptor agonist, or S1P receptor antagonist.

DETAILED DESCRIPTION OF THE INVENTION

The present invention stems from studies that were conducted to determine whether the involvement of spinal ceramide in opioid analgesic tolerance and hyperalgesia occurs via signaling through S1P. Through the pharmacological targeting of specific steps in the de novo and SMase pathways, it has been demonstrated, for the first time, that spinally-formed S1P is a key secondary messenger contributing to neuropathic pain, inflammatory pain, hypersensitivity, and antinociceptive tolerance, at least in part, through modulation of glial cell function. A varied platform approach of pharmacological manipulation is provided that can intercept the ceramide metabolic pathway at many levels to preempt and treat neuropathic pain, inflammatory pain, hypersensitivity, and antinociceptive tolerance.

Figure 6:
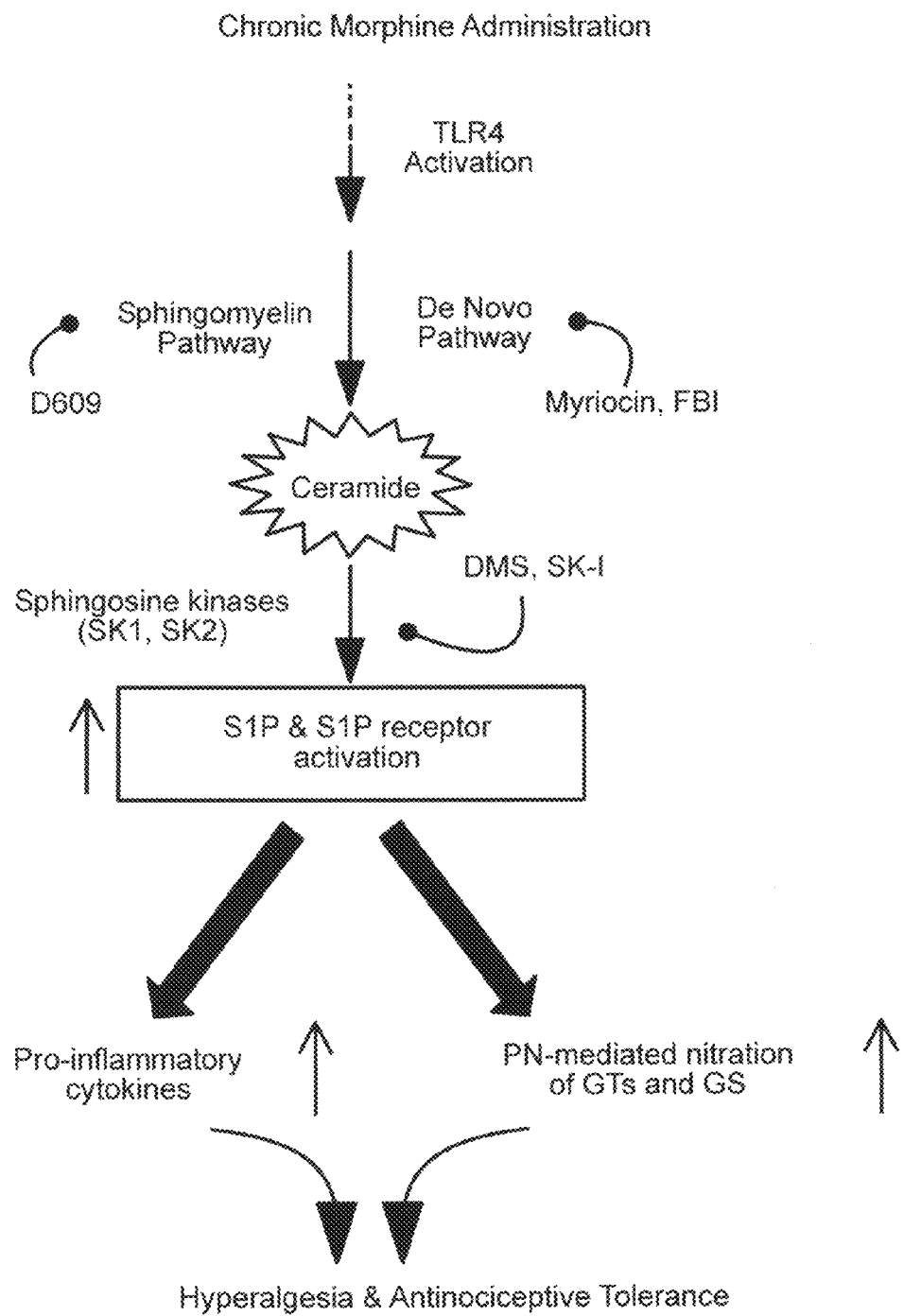
Figure 7:
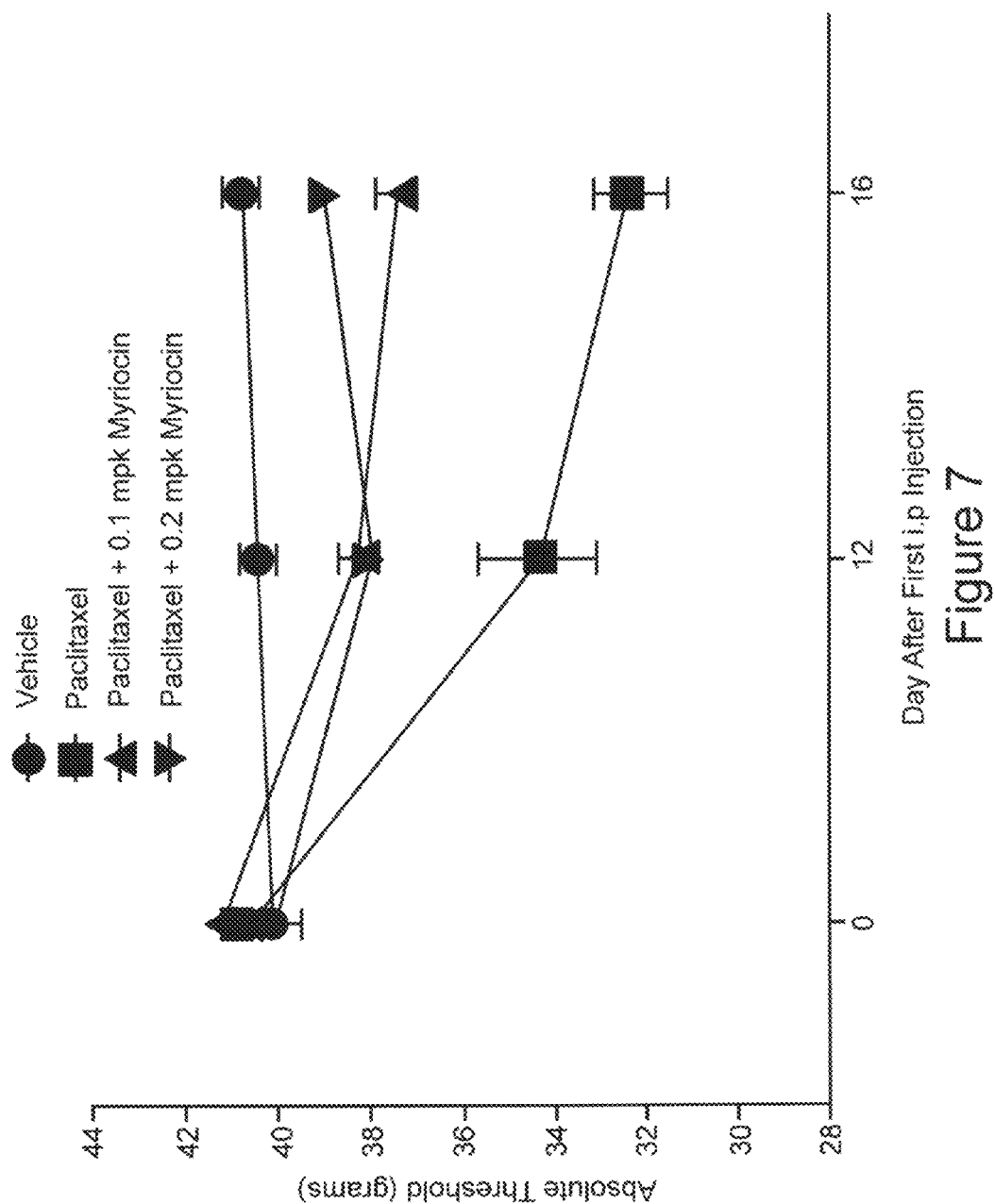
Figure 8:
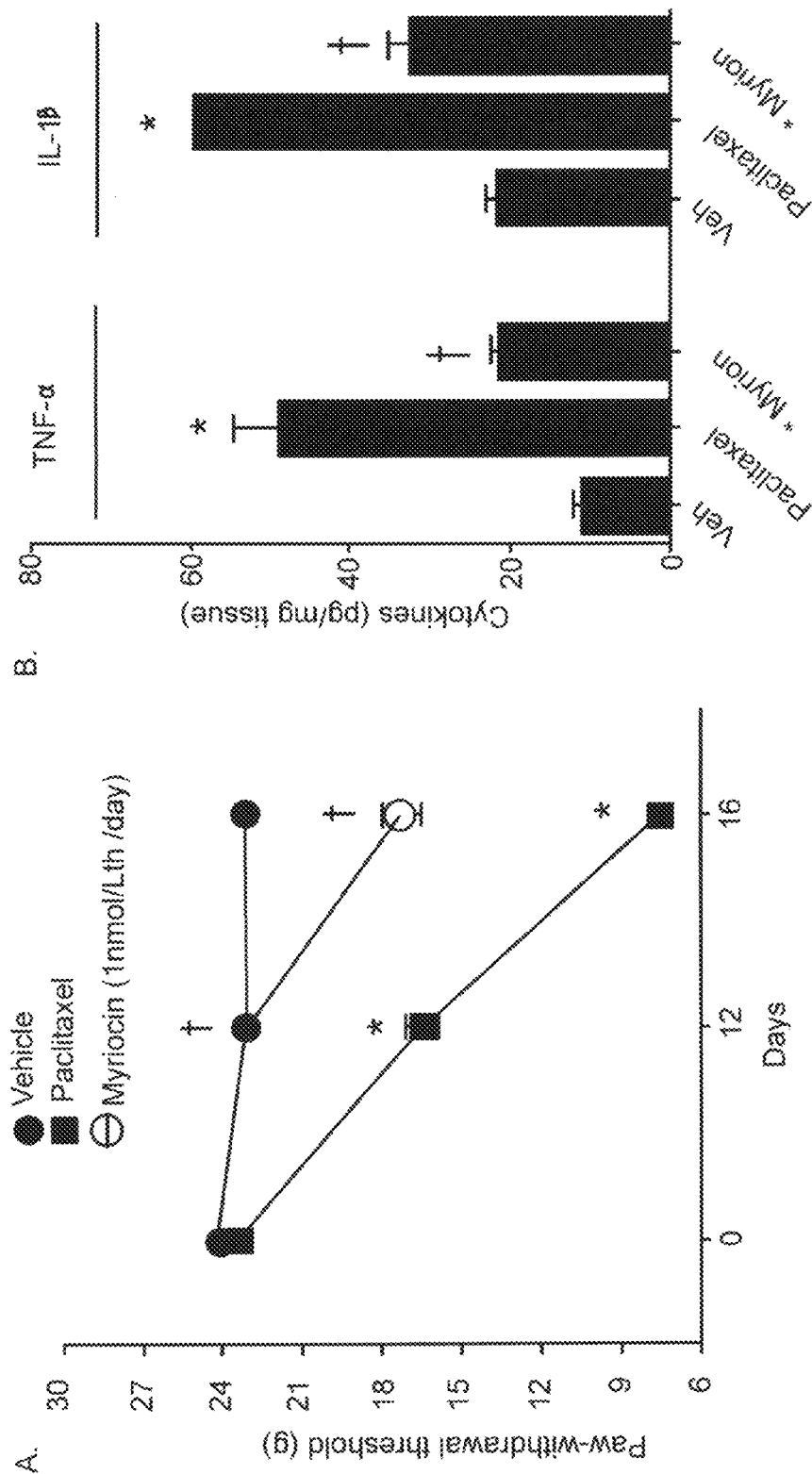

In particular, it has been discovered that ceramide-derived S1P plays a key role in the development of morphine-induced hyperalgesia and antinociceptive tolerance, providing a novel mechanistic rationale for development of inhibitors of ceramide and S1P as adjunct to opiates in pain management. In addition to the role of S1P on glia, S1P was shown to contribute to the development of morphine-induced hyperalgesia and antinociceptive tolerance by affecting neurons. A model of this process is shown in FIG. 6 providing that chronic administration of morphine activates the ceramide metabolic pathway in spinal glial cells (astrocytes and microglial cells) resulting in increased production in S1P by sphingosine kinases. Following its extracellular release, S1P then binds to its receptors on glial cells initiating a series of signaling pathways culminating in enhanced production of the well known proinflammatory and neuroexcitatory cytokines, IL-1β TNF-α, and IL-6 Inhibition of S1P blocks the formation of these cytokines suggesting that the attenuation of morphine-induced hyperalgesia and tolerance by inhibitors of S1P formation (such as sphingosine kinase inhibitors) is secondary to suppression of morphine-induced spinal cytokine formation.

Without being bound by a particular theory, it is believed that the mechanism for S1P involvement can be shown by activation of redox-sensitive transcription factors (e.g. NFKB) and several MAPKs including P38 and ERK1/2 known to regulate the production of proinflammatory mediators from glial cells (Watkins et al., 2001; Tanga et al., 2006). Furthermore, NF-KB, P38 kinase and ERK have been implicated in the development of morphine-induced hyperalgesia and antinociceptive tolerance (Cui et al., 2006; Ndengele et al., 2009; Wang et al., 2009). Thus, S1P may contribute to the development of morphine-induced hyperalgesia and antinociceptive tolerance by activating glial cells to release proinflammatory cytokines in an NF-kB and MAPKs (P38 kinase, ERK) dependent manner.

In addition, and without being bound by a particular theory, another signaling pathway engaged by S1P appears to occur through the formation and rapid reactions of peroxynitrite ("PN"). S1P can increase the formation of superoxide and nitric oxide by activating, respectively, the NADPH oxidase and nitric oxide synthase (Keller et al., 2006; Nayak et al., 2010). Both superoxide and nitric oxide are precursors in the biosynthesis of PN (Beckman et al., 1990), a potent proinflammatory (Salvemini et al., 1998) and pronociceptive nitroxidative species (Salvemini and Neumann, 2010) also implicated in the development of opiate-induced hyperalgesia and antinociceptive tolerance (Salvemini and Neumann, 2009).

S1P therefore contributes to the development of morphine-induced hyperalgesia and antinociceptive tolerance by favoring the production of PN, which in turn, nitrates key glial cell proteins known to be involved in maintaining optimal spinal glutamatergic signaling. Indeed, inhibition of S1P with DMS blocked the formation of 3-nitrotyrosine ("NT"), a marker for PN (Muscoli et al., 2007). It is well established that glutamate neurotransmission, in particular as mediated via NMDA receptors, is key in the development of opioid tolerance (Trujillo and Akil, 1991). The homeostasis of extracellular glutamate is tightly regulated by sodium-dependent high-affinity glutamate transporters (GTs) in the plasma membranes of both neurons and glia, although the bulk (over 90%) of functional glutamate uptake is mediated by the glial transporters: glutamate/aspartate transporter (GLAST) and GLT-1 (Danbolt, 2001). If GLAST/GLT-1 function is impacted upon (i.e. reduced or eliminated), glutamate can increase in the CSF contributing to rapid alterations in synaptic transmission (Nakagawa et al., 2001).

In contradistinction to the central role of GTs in regulating the homeostasis of extracellular glutamate, the glial cell enzyme GS plays a pivotal role in its intracellular metabolic fate (Suarez et al., 2002). In the CNS, GS is located mainly in astrocytes and one of the primary roles of these cells is to protect neurons against excitotoxicity by taking up excess ammonia and glutamate, and converting them into glutamine (Suarez et al., 2002). Glutamine is then transported into neurons, where it serves as a precursor for the formation of glutamate and GABA (Waniewski and Martin, 1986). Enzymatic inactivation of GS facilitates neuronal excitation (Suarez et al., 2002; Muscoli et al., 2005). Furthermore, through feedback regulation, a decrease in the activity of glutamine synthetase can reduce the activity of glutamate transporter (Suarez et al., 2002) underscoring the reciprocal interaction between these two pathways. Inhibition of GS activity blocks central sensitization associated with inflammatory hyperalgesia (Chiang et al., 2007).

It has also been discovered that nitration of GLT-1 and GS was blocked by DMS. Thus, inhibition of hyperalgesia and antinociceptive tolerance by inhibitors of S1P is secondary, at least in part, to inhibition of PN generation and subsequent post-translational nitration and inactivation of GLT-1 and GS. Without being bound to any particular theory, it is believed that, by preventing nitration of these glial cell proteins, DMS reduces glutamate to basal levels thus restoring optimal glutamatergic neurotransmission.

The mechanistic connections between chronic administration of morphine, activation of the ceramide metabolic pathway, and the development of hyperalgesia and antinociceptive tolerance remains unknown. Again, without being bound by a particular theory, a growing body of data has recently emerged that implicates activation of Toll-like receptor 4 (TLR4) on glial cells in the development of opiate induced hyperalgesia and antinociceptive tolerance as well as neuropathic pain (Tanga et al., 2005; Watkins et al., 2009). Activation of TLR4 by LPS (a well known exogenous ligand for TLR4) on monocytes and macrophages activates enzymes in the de novo and SM pathways leading to increased production of ceramide which in turn activate NF-kB and MAPKs to increase the production of nitric oxide and superoxide, as well as, TNF-α and IL-β events that have been linked to the development of sepsis and septic shock (Delogu et al., 1999; Claus et al., 2005; Cuzzocrea et al., 2009). Therefore, when analyzed collectively, activation of the TLR4-derived signaling pathway by morphine, a recently documented TLR4 agonist (Watkins et al., 2009), may link chronic morphine administration to activation of the ceramide metabolic pathway and hence the development of hyperalgesia and antinociceptive tolerance.

Considering the appreciable molecular, biochemical, and pharmacological similarities between opiate-mediated hypersensitivity, and hypersensitivity associated with chronic neuropathic pain from diabetes mellitus and other sensory neuropathies (Mao et al., 1995; Watkins et al., 2005), the hypothesis that ceramide and S1P may be viable therapeutic targets in both conditions was also investigated. Such studies identified the 51P1 receptor as particularly important in models of chemotherapy-induced neuropathic pain.

Figure 10:
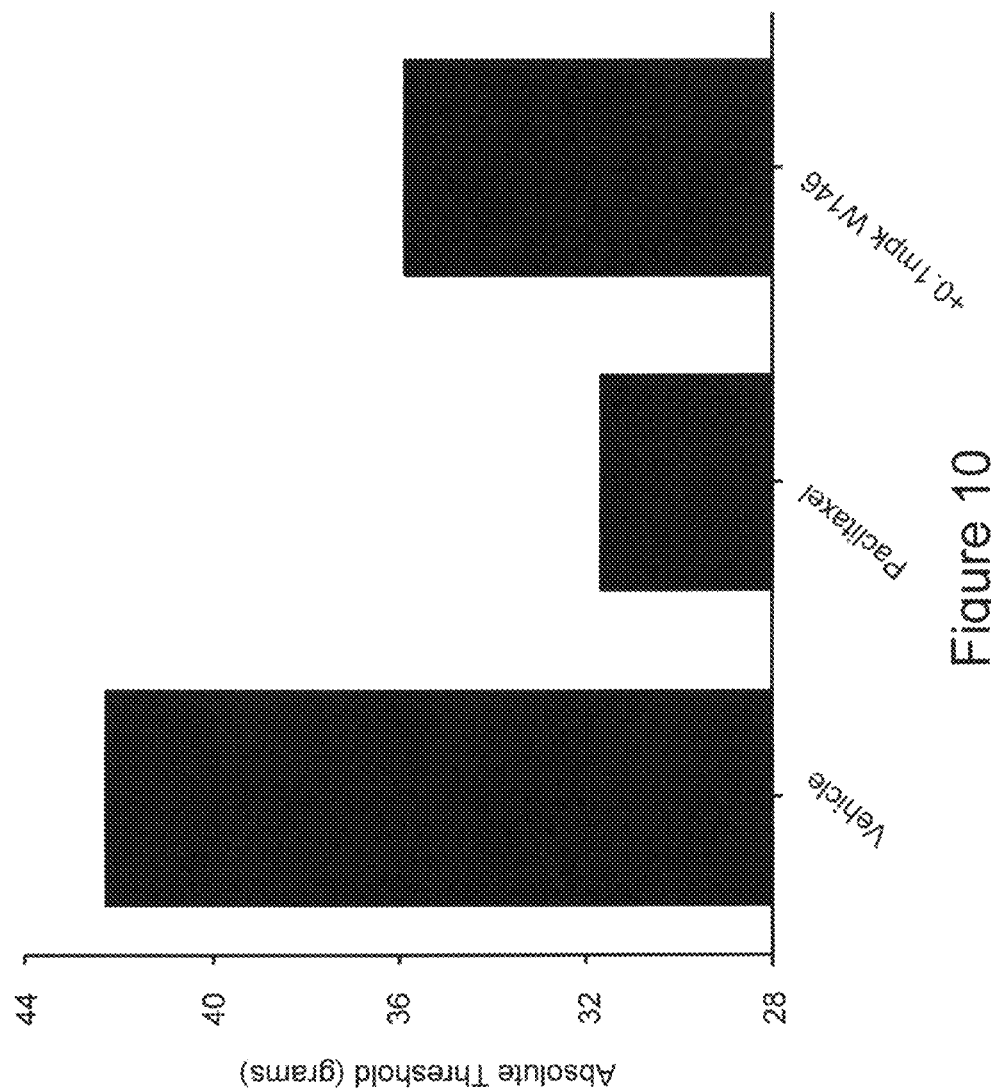
Figure 11:
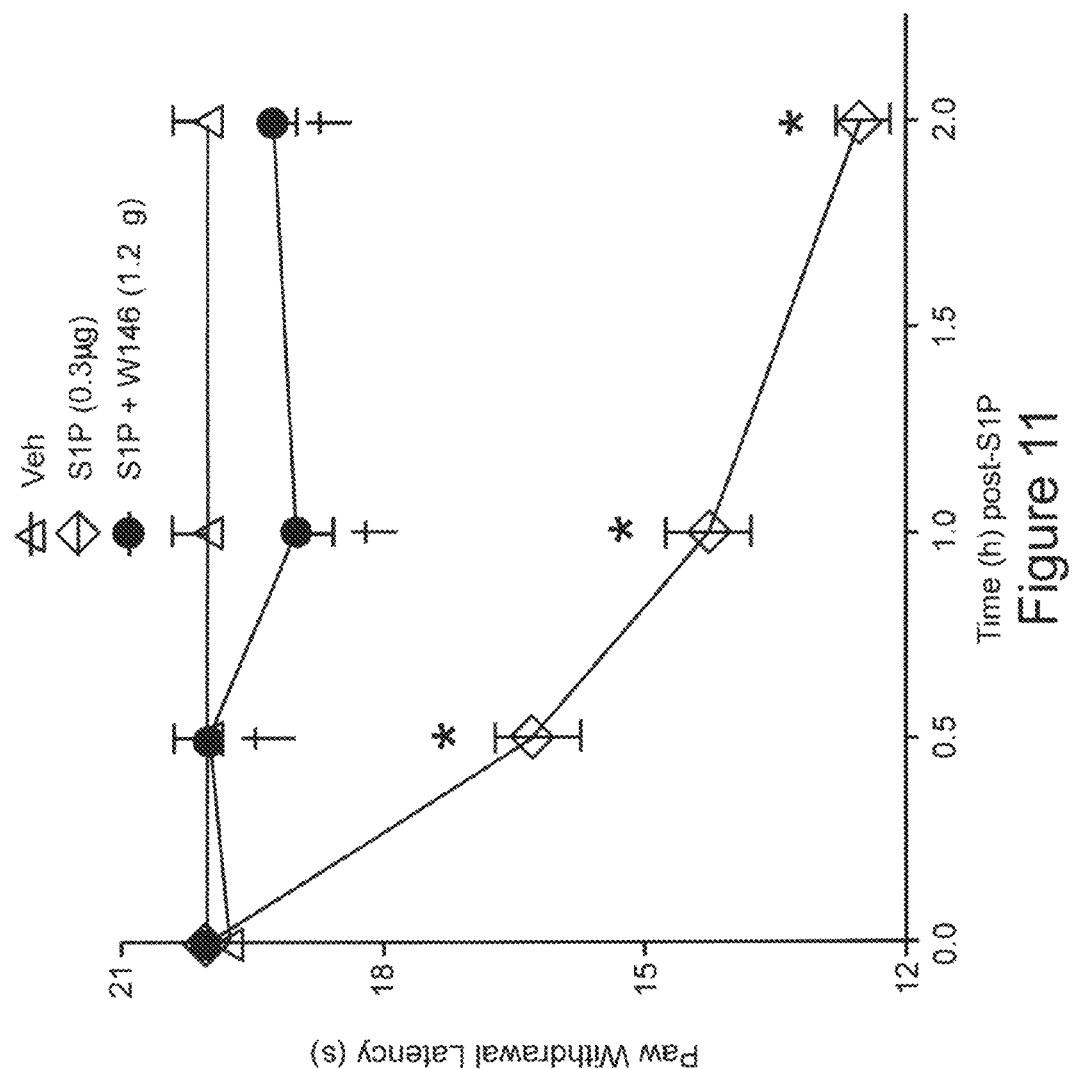
Figure 12:
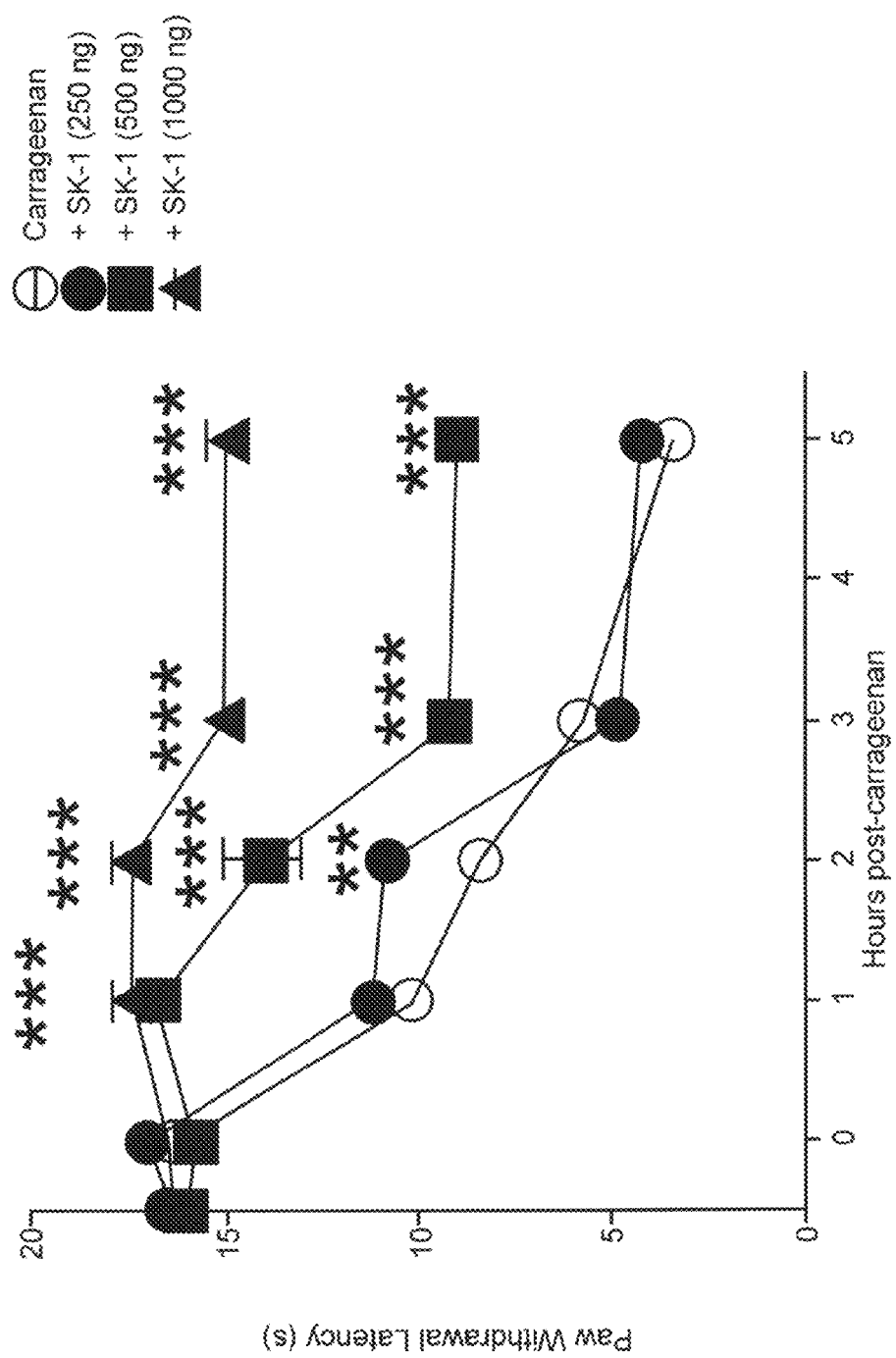
Figure 13:
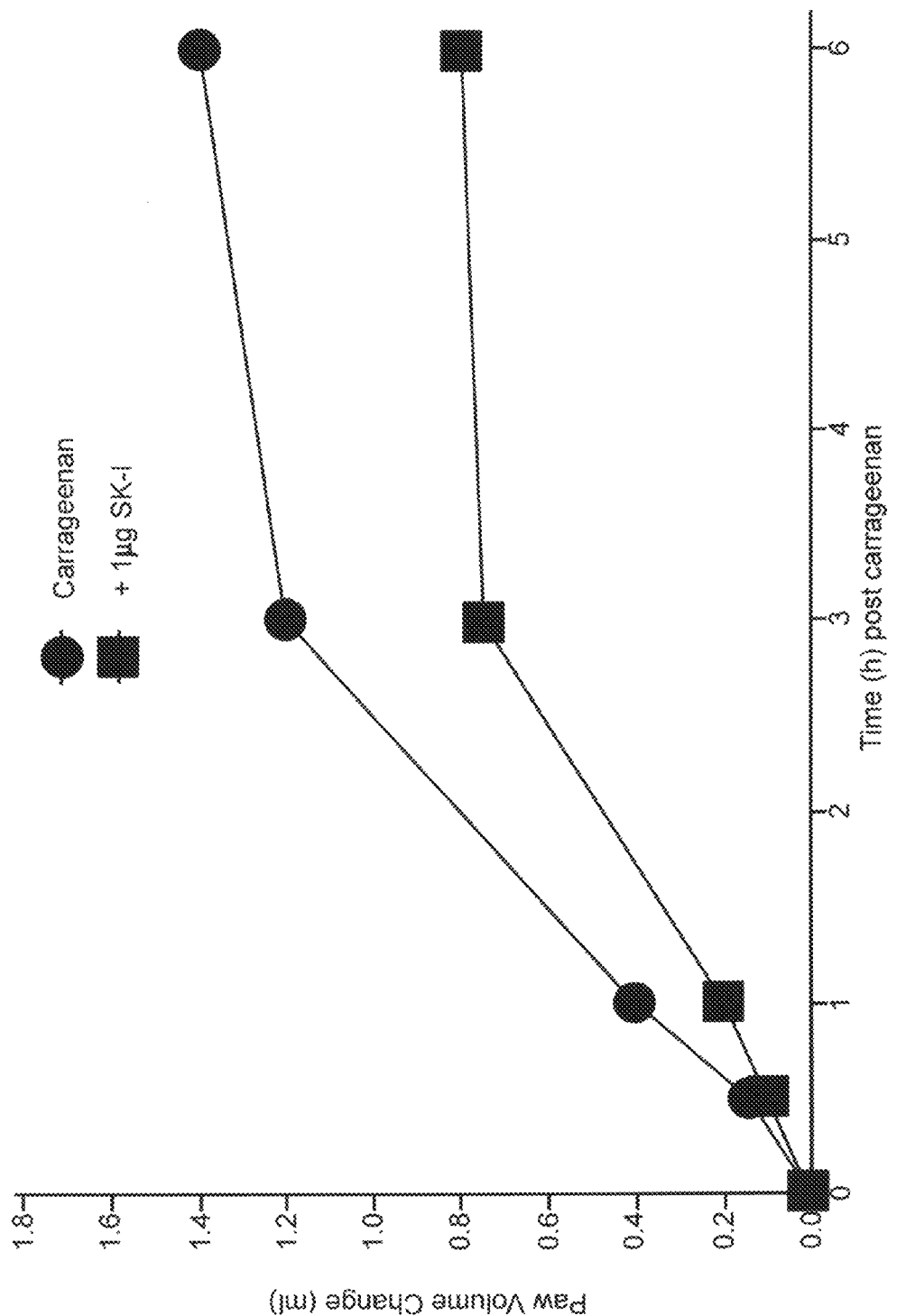
Figure 14:
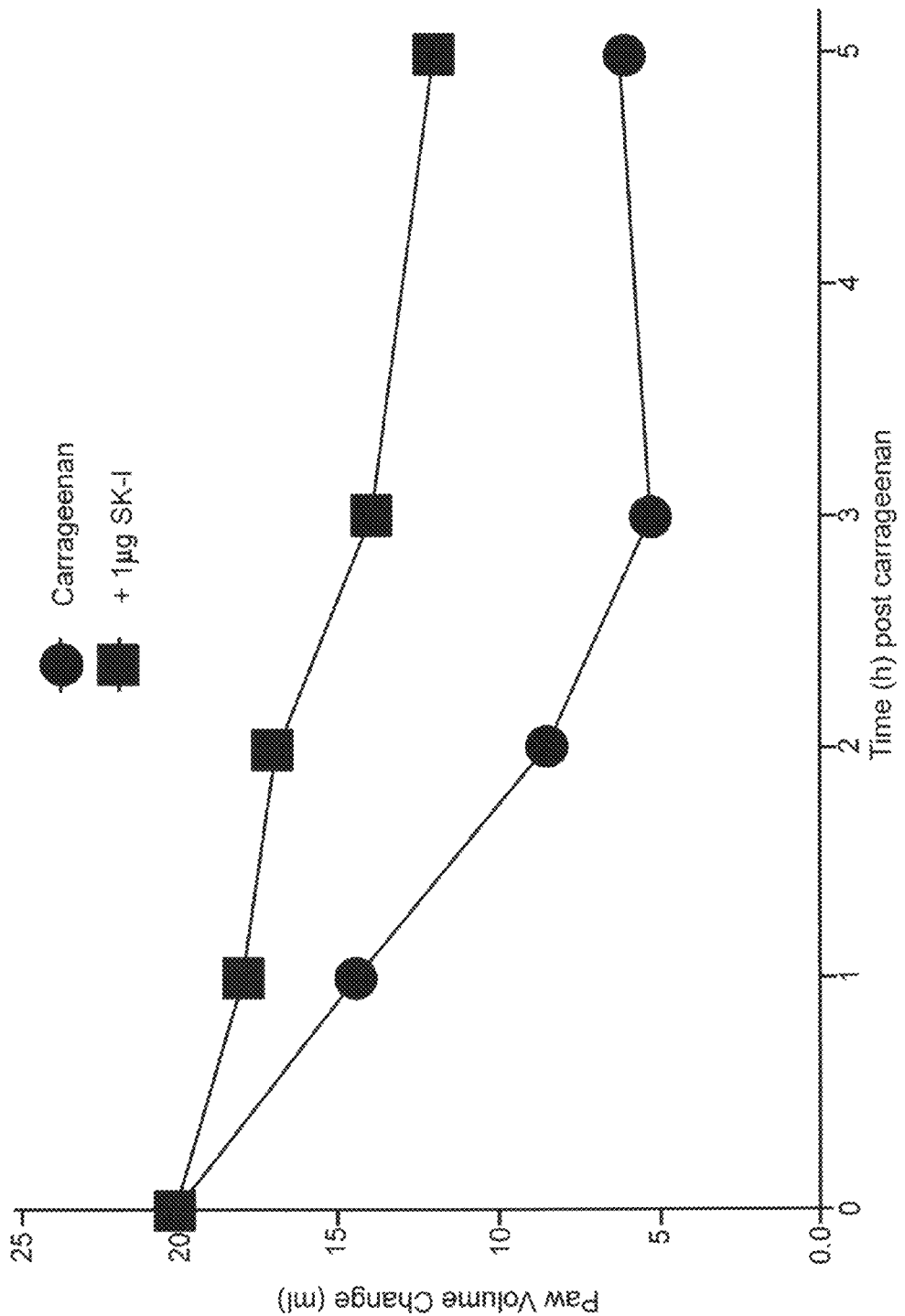

In particular, it was demonstrated that S1P receptor antagonists reverse ceramide-induced hyperalgesia (FIG. 28) and chemotherapy-induced neuropathic pain (FIGS. 10 and 11). It was further demonstrated that S1P receptor agonists, in particular agonists to the S1P1, S1P3, and S1P5 receptor subtypes, block the development of chemotherapy-induced neuropathic pain. (FIGS. 20-24). Without being bound to any particular theory, it is believed that S1P receptor agonists cause internalization of S1P receptors and degrade them so that they cannot recycle. Additional experimental data (FIG. 27) show that S1P receptor agonists block development of inflammatory pain induced by carrageenan, thereby providing another avenue for the treatment of all types of inflammatory pain, such as chronic inflammatory pain in rheumatoid arthritis.

General Techniques

The practice of certain aspects of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (MJ. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and Cc. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995); and Cancer: Principles and Practice of Oncology (V. T. DeVita et al., eds., J. B. Lippincott Company, 1993).

Methods of Using Anti-S1P Antibodies and Anti-S1P Receptor Antibodies for Therapeutic Purposes In one aspect of the invention, anti-S1P antibodies and anti-S1P receptor antibodies are administered for reducing and blocking the biological activity of S1P. This antagonistic activity is believed to be useful in the treatment of pathological conditions associated with endogenous S1P production in the spinal cord, such as neuropathic pain, inflammatory pain, hypersensitivity, and antinociceptive tolerance. Preferably, in these aspects an effective amount of antibody is administered to an individual. Accordingly, in one aspect, the invention provides a method of antagonizing human S1P biological activity using any of the antagonists (including polypeptides and antibodies such as LT1009) disclosed herein. In one aspect, the method comprises contacting S1P with any of the polypeptides (including LT1009) described herein, whereby neuropathic pain, inflammatory pain, hypersensitivity, and antinociceptive tolerance mediated by S1P activity is antagonized, reduced, blocked, or suppressed. In yet another aspect, an individual with neuropathic pain (such as cancer pain or chemotherapy-induced pain) is treated with an anti-S1P antibody (including LT1009) or anti-S1P receptor antibody or combination thereof.

For simplicity, reference will be made generally to anti-S1P antibody (including LT1009) or anti-S1P receptor antibody with the understanding that these methods apply to any of the variant antibodies and polypeptides described herein.

Various formulations of anti-S1P antibody or anti-S1P receptor antibody or fragments (e.g., Fab, Fab', F(ab')2, Fv, Fe, etc.), such as single chain (ScFv), mutants thereof, fusion proteins comprising an antibody portion, and any other modified configuration of anti-S1P antibody or anti-S1P receptor antibody that comprises an S1P/S1P receptor (including S1P1 receptor) recognition site of the required specificity, may be used for administration to an individual in need thereof. In some aspects, anti-S1P antibody and/or anti-S1P receptor antibody or various formulations thereof may be administered neat. In other aspects, anti-S1P antibody or anti-S1P receptor antibody or various formulations (including any composition aspect described herein) thereof and a pharmaceutically acceptable excipient can be administered, and may be in various formulations. Pharmaceutically acceptable excipients are known in the art. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in Remington, The Science and Practice of Pharmacy 20th Ed. Mack Publishing (2000).

In some aspects, these agents are formulated for administration by injection (e.g., intraperitoneally, intravenously, subcutaneously, intramuscularly, etc.), although other forms of administration (e.g., oral, mucosal, via inhalation, sublingually, etc.) can be also used. Accordingly, anti-S1P antibody and/or anti-S1P receptor antibody and equivalents thereof are preferably combined with pharmaceutically acceptable vehicles such as saline, Ringer's solution, dextrose solution, and the like. The particular dosage regimen, i.e., dose, timing and repetition, will depend on the particular individual and that individual's medical history. Generally, any of the following doses may be used: a dose of at least about 50 mg/kg body weight; at least about 10 mg/kg body weight; at least about 3 mg/kg body weight; at least about 1 mg/kg body weight; at least about 750 µg/kg body weight; at least about 500 µg/kg body weight; at least about 250 µg/kg body weight; at least about 100 µg/kg body weight; at least about 50 µg/kg body weight; at least about 10 µg/kg body weight; at least about 1 µg/kg body weight, or less, is administered. For repeated administrations over several days or longer, depending on the condition, the treatment is sustained until a desired suppression of disease symptoms occurs. An exemplary dosing regimen comprises administering an initial dose of about 2 mg/kg, followed by a weekly maintenance dose of about 1 mg/kg of the anti-S1P antibody and/or anti-S1P receptor antibody, or followed by a maintenance dose of about 1 mg/kg every other week. However, other dosage regimens may be useful, depending on the pattern of pharmacokinetic decay that the practitioner wishes to achieve. Empirical considerations, such as the half-life, generally will contribute to determination of the dosage. The progress of this therapy is easily monitored by conventional techniques and assays.

In some individuals, more than one dose may be required. Frequency of administration may be determined and adjusted over the course of therapy. For example, frequency of administration may be determined or adjusted based on the type and severity of the neuropathic pain to be treated, whether the agent is administered for preventive or therapeutic purposes, previous therapy, the patient's clinical history and response to the agent, and the discretion of the attending physician. Typically the clinician will administer an anti-S1P antibody and/or anti-S1P receptor antibody, until a dosage is reached that achieves the desired result. In some cases, sustained continuous release formulations of anti-S1P antibody and/or anti-S1P receptor antibody may be appropriate. Various formulations and devices for achieving sustained release are known in the art.

In one aspect, dosages for anti-S1P antibody and/or anti-S1P receptor antibody (or polypeptides) may be determined empirically in individuals who have been given one or more administration(s). Individuals are given incremental dosages of anti-S1P antibody and/or anti-S1P receptor antibody. To assess efficacy of anti-S1P antibody and anti-S1P receptor antibody or other equivalent antibody, markers of the disease symptoms (such as neuropathic pain) can be monitored.

Administration of an anti-S1P antibody and/or anti-S1P receptor antibody or polypeptide in accordance with the methods of the present invention can be continuous or intermittent, depending, for example, upon the recipient's physiological condition, whether the purpose of the administration is therapeutic or prophylactic, and other factors known to skilled practitioners. The administration of an antibody may be essentially continuous over a preselected period of time or may be in a series of spaced doseages, e.g., either before, during, or after developing neuropathic pain, inflammatory pain or hyperalgesia.

Other formulations include suitable delivery forms known in the art including, but not limited to, carriers such as liposomes. See, for example, Mahato et al. (1997) Pharm. Res. 14:853-859. Liposomal preparations include, but are not limited to, cytofectins, multilamellar vesicles and unilamellar vesicles.

In some aspects, more than one antibody or polypeptide may be administered. The antibodies can be monoclonal or polyclonal. Such compositions may contain at least one, at least two, at least three, at least four, at least five different antibodies. A mixture of antibodies, as they are often denoted in the art, may be particularly useful in treating a broader range of population of individuals.

A polynucleotide encoding any of the antibodies or polypeptides of the invention (such as anti-S1P antibody and anti-S1P receptor antibody) may also be used for delivery and expression of any of the antibodies or polypeptides of the invention in a desired cell. It is apparent that an expression vector can be used to direct expression of an anti-S1P antibody and anti-S1P receptor antibody or polypeptide. The expression vector can be administered by any means known in the art, such as intraperitoneally, intravenously, intramuscularly, subcutaneously, intrathecally, intraventricularly, orally, enterally, parenterally, intranasally, dermally, sublingually, or by inhalation. For example, administration of expression vectors includes local or systemic administration, including injection, oral administration, p3lticle gun or catheterized administration, and topical administration. One skilled in the art is familiar with administration of expression vectors to obtain expression of an exogenous protein in vivo. See, e.g., U.S. Pat. Nos. 6,436,908; 6,413,942; and 6,376,471.

Targeted delivery of therapeutic compositions comprising a polynucleotide encoding any of the antibodies or polypeptides of the invention (such as anti-S1P antibody and anti-S1P receptor antibody) can also be used. Receptor-mediated DNA delivery techniques are described in, for example, Findeis et al., Trends Biotechnol. (1993) 11:202; Chiou et al., Gene Therapeutics: Methods And Applications Of Direct Gene Transfer (1. A. Wolff, ed.) (1994); Wu et al., J. Biol. Chem. (1988) 263:621; Wu et al., J. Biol. Chem. (1994) 269:542; Zenke et al., Proc. Natl. Acad. Sci. (USA) (1990) 87:3655; Wu et al., J. Biol. Chem. (1991) 266:338. Therapeutic compositions containing a polynucleotide are administered in a range of about 100 ng to about 200 mg of DNA for local administration in a gene therapy protocol. Concentration ranges of about 500 ng to about 50 mg, about 1 mg to about 2 mg, about 5 mg to about 500 mg, and about 20 mg to about 100 mg of DNA can also be used during a gene therapy protocol. The therapeutic polynucleotides and polypeptides of the present invention can be delivered using gene delivery vehicles. The gene delivery vehicle can be of viral or non-viral origin (see generally, Jolly, Cancer Gene Therapy (1994) 1:51; Kimura, Human Gene Therapy (1994) 5:845; Connelly, Human Gene Therapy (1995) 1:185; and Kaplin, Nature Genetics (1994) 6: 148). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91102805; U.S. Pat. Nos. 5,219,740; 4,777,127; GB Patent No. 2,200,651; and EP Patent No. 0345242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532≥≥, and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther. (1992) 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther. (1992) 3:147); ligand-linked DNA (see, e.g., Wu J. Biol. Chem. (1989) 264:16985); eukaryotic cell-delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP Patent NO. 0524968. Additional approaches are described in Philip, Mol. Cell. Biol. (1994) 14:2411 and in Woffendin, Proc. Natl. Acad. Sci. (1994) 91:1581.

With respect to all methods described herein, reference to sphingosine kinase antagonist, S1P antagonist, S1P receptor agonist, and S1P receptor antagonist, also includes compositions comprising one or more of these agents. These compositions may further comprise suitable excipients, such as pharmaceutically acceptable excipients including buffers, which are well known in the art. The present invention can be used alone or in combination with other conventional methods of treatment.

Sphingosine Kinase Antagonists, S1P Antagonists, S1P Receptor Agonists, and S1P Receptor Antagonists for the Treatment of Neuropathic Pain, Inflammatory Pain, Hypersensitivity, and Antinociceptive Tolerance In some aspects, the invention provides methods for treating neuropathic pain (such as cancer pain and chemotherapy-induced pain), inflammatory pain, hypersensitivity, and antinociceptive tolerance in individuals including mammals, both human and non-human.

Accordingly, in one aspect, the invention provides methods for treatment of neuropathic pain, inflammatory pain, hypersensitivity, and antinociceptive tolerance in an individual comprising administering an effective amount of a sphingosine kinase antagonist, S1P antagonist, S1P receptor agonist, or S1P receptor antagonist. As intended herein, the term "treatment" includes, but is not limited to, removing, reducing the incidence of, ameliorating, suppressing, palliating, and delaying the onset, the development or the progression of neuropathic pain, induced pain, inflammatory pain, hypersensitivity, and antinociceptive tolerance in an individual. Thus, in some aspects, the sphingosine kinase antagonist, S1P antagonist, S1P receptor agonist, or S1P receptor antagonist is administered prior to development of pain or a pain episode in an individual, for example an individual having cancer or the subject of chemotherapy.

Neuropathic pain relief and inflammatory pain relief may be characterized by time course of relief. Accordingly, in some aspects, pain relief is observed within about 24 hours after administration of a sphingosine kinase antagonist, S1P antagonist, S1P receptor agonist, or S1P receptor antagonist. In other aspects, pain relief can be observed within about 36, 48, 60, 72 hours or 4 days after administration of a sphingosine kinase antagonist, S1P antagonist, S1P receptor agonist, or S1P receptor antagonist. In still other aspects, pain relief is observed before observing an indication of improvement of neuropathic pain or inflammatory pain. In some aspects, frequency and intensity of pain can be diminished, and quality of life of those suffering from neuropathic pain can be increased. For hyperalgesia and allodynia, a decreased sensitivity to pain may be observed within similar time frames and similarly improved conditions.

When treating chemotherapy-induced pain, the methods of the invention may be used in conjunction with any chemotherapeutic drug. Example drugs include, but are not limited to, taxanes, platinum compounds, vinca alkaloids, and proteasome inhibitors. Preferred chemotherapeutic drugs include paclitaxel, oxaliplatin, bortezomib, and vincristine.

Sphingosine Kinase Antagonists, S1P Antagonists and S1P Receptor Antagonists

In one aspect, the invention provides methods that use a sphingosine kinase antagonist, S1P antagonist or S1P receptor antagonist, terms which refer to any molecule that blocks, suppresses or reduces (including significantly) S1P biological activity, including downstream pathways mediated by S1P signaling, such as receptor binding and elicitation of a cellular response to S1P. The term "antagonist" implies no specific mechanism of biological action, and is deemed to expressly include and encompass all possible pharmacological, physiological, and biochemical interactions with S1P and its consequences which can be achieved by a variety of different, and chemically divergent, compositions.

Some known sphingosine kinase antagonists are agents which molecularly mimic the natural substrates of sphingosine kinase. Such antagonists bind to sphingosine kinase, in some instances irreversibly, and thereby prevent the binding of natural substrates of sphingosine kinase, ultimately preventing the phosphorylation of these substrates. Examples of sphingosine kinase antagonists include methylsphingosine, N,N-dimethyl sphingosine, trimethylsphingosine, D,L-threo-dihydrosphingosine and high density lipoprotein. Other sphingosine derivatives that can be used as sphingosine kinase inhibitors are described in U.S. Pat. Nos. 5,583,160; 5,627,171; 5,466,716; 5,391,800; 5,137,919; 5,151,360; 5,248,824; 5,260,288; and 5,331,014. De Jonghe et al. disclose the use of short-chain sphingoid bases, including short chain sphinganine analogs and 3-fluoro-sphingosine analogs as inhibitors of sphingosine kinase. (De Jonghe et al., Bioorg Med Chem Lett 1999 9 (21):3175-3180).

Other sphingosine kinase antagonists may bind sphingosine kinase at sites other than the substrate binding site, provided they ultimately interfere with the catalytic activity of the kinase. A suitable sphingosine kinase antagonist may interfere with the catalytic activity of sphingosine kinase by interfering with or preventing the interaction with substrates or catalysts, or interfering or preventing the release of products, or by preventing the modification of the substrates by the enzyme. The cloning of murine sphingosine kinase (GenBank Accession Nos. AF068748, AF068749) has been reported by Kohama et al., as have expression studies and activity studies aimed at measuring specific sphingosine kinase activity. (Kohama et al., J Biol Chem 1998273 (37): 23722-8) GenBank Accession Nos. NM021972 and XM012589 correspond to sequences of cloned human sphingosine kinase. Assays for any of the above agent classes have been described in the literature, and especially in PCT patent application Ser. No. PCT/AU98/00730 (WO 99/12533), which are incorporated herein by reference in their entirety, which documents methods for measuring sphingosine kinase activity as well as methods for identifying sphingosine kinase agonists and antagonists.

Exemplary S1P antagonists or S1P receptor antagonists include, but are not limited to: an anti-S1P antibody (such as LT1002), an anti-S1P1 receptor antibody (such as LT1009), an anti-sense molecule directed to S1P (including an anti-sense molecule directed to a nucleic acid encoding S1P), an anti-sense molecule directed to an S1P receptor (such as S1P1), an S1P inhibitory compound, and an S1P structural analog.

For purpose of the present invention, it will be explicitly understood that the term "antagonist" encompasses all the previously identified terms, titles, and functional states and characteristics whereby the S1P itself, an S1P biological activity (including but not limited to its ability to mediate any aspect of neuropathic pain), or the consequences of the biological activity, are substantially nullified, decreased, or neutralized in any degree. In some aspects, an S1P antagonist or S1P receptor antagonist (e.g., an antibody) binds S1P, binds to an S1P receptor (such as S1P1 receptor), and reduces (impedes and blocks) downstream S1P receptor signaling or S1P secondary messenger activity. In other aspects, a sphingosine kinase antagonist can inhibit the formation of S1P. Accordingly, in some aspects, an S1P antagonist binds (physically interacts with) sphingosine kinase, S1P, or an S1P receptor. In some aspects, the S1P antagonist is a polypeptide which binds to sphingosine kinase, S1P, or an S1P receptor.

In some aspects, the sphingosine kinase antagonist, S1P antagonist or S1P receptor antagonist is a peptide including an antibody or antibody fragment, or a modified peptide (such as S1P binding peptide fused to an Fc domain). In other aspects, an S1P antagonist or S1P receptor antagonist reduces (impedes and blocks) downstream S1P receptor signaling (e.g., inhibitors of kinase or phosphorylation signaling). In still other aspects, an antagonist is an anti-S1P antibody that is humanized (such as LT1009). In other aspects, the anti-S1P antibody comprises one or more CDR(s) of LT1009 (such as one, two, three, four, five, or, in some aspects, all six CDRs from LT1009). In other aspects, the anti-S1P antibody is fully human. In still other aspects, the anti-S1P antibody comprises the amino acid sequence of the heavy chain variable region and the amino acid sequence of the light chain variable region shown in FIGS. 29 (SEQ ID NO:1) and 30 (SEQ ID NO:2). In still other aspects, the antibody comprises a modified constant region, such as a constant region that is immunologically inert, e.g., does not trigger complement mediated lysis, or does not stimulate antibody-dependent cell mediated cytotoxicity (ADCC).

The antibodies useful in the present invention can encompass monoclonal antibodies, polyclonal antibodies, antibody fragments (e.g., Fab, Fab', F(ab')2, Fv, Fc, etc.), chimeric antibodies, bispecific antibodies, heteroconjugate antibodies, single chain (ScFv), mutants thereof, fusion proteins comprising an antibody portion, humanized antibodies, and any other modified configuration of the immunoglobulin molecule that comprises an antigen recognition site of the required specificity, including glycosylation variants of antibodies, amino acid sequence variants of antibodies, and covalently modified antibodies. The antibodies may be murine, rat, human, or any other origin (including chimeric or humanized antibodies).

The binding affinity of, for example, an anti-S1P antibody or anti-S1P receptor antibody for binding to S1P or S1P receptor, respectively, can be about 0.10 to about 0.80 nM, about 0.15 to about 0.75 nM and about 0.18 to about 0.72 nM. In one aspect, the binding affinity is between about 2 pM and 22 pM. In one aspect, the binding affinity is between about 23 pM and about 100 pM. In some aspects, the binding affinity is about 10 nM. In other aspects, the binding affinity is less than about 10 nM. In other aspects, the binding affinity is about 0.1 nM or about 0.07 nM. In other aspects, the binding affinity is less than about 0.1 nM or less than about 0.07 nM. In other aspects, the binding affinity is any of about 100 nM, about 50 nM, about 10 nM, about 1 nM, about 500 µM, about 100 pM, or about 50 pM to any of about 2 pM, about 5 pM, about 10 pM, about 15 pM, about 20 pM, or about 40 pM. In some aspects, the binding affinity is any of about 100 nM, about 50 nM, about 10 nM, about 1 nM, about 500 pM, about 100 pM, or about 50 pM, or less than about 50 pM. In some aspects, the binding affinity is less than any of about 100 nM, about 50 nM, about 10 nM, about 1 nM, about 500 pM, about 100 pM, or about 50 pM. In still other aspects, the binding affinity is about 2 pM, about 5 pM, about 10 pM, about 15 pM, about 20 pM, about 40 pM, or greater than about 40 pM.

Methods for determining binding affinity of antibodies are known. One way of determining binding affinity of antibodies to S1P or S1P receptor, according to the present invention, is by measuring binding affinity of monofunctional Fab' fragments of the antibody. To obtain monofunctional Fab fragments, an antibody (for example, IgG) can be cleaved with papain or expressed recombinantly. The affinity of, for example, an anti-S1P Fab fragment of an antibody can be determined by surface plasmon resonance (BIAcore3000™ surface plasmon resonance (SPR) system, BIAcore, INC, Piscataway N.J.). CM5 chips can be activated with N-ethyl-N'-(3dimethylaminopropyl)-carbodiimide hydrochloride (EDC) and N-hydroxysuccinimide (NHS) according to the supplier's instructions. Human S1P (or any other S1P) can be diluted into 10 mM sodium acetate pH 4.0 and injected over the activated chip at a concentration of 0.005 mg/mL. Using variable flow time across the individual chip channels, two ranges of antigen density can be achieved: 100-200 response units (RU) for detailed kinetic studies and 500-600 RU for screening assays. The chip can be blocked with ethanolamine. HBS-EP buffer (0.01 M HEPES, pH 7.4, 0.15 NaCl, 3 mM EDTA, 0.005% Surfactant P29) can be used as running buffer for the BIAcore assays. Serial dilutions (0.1-10×estimated KD) of purified Fab samples can be injected for 1 min at 100 µL/min and dissociation times of up to 2h can be allowed. The concentrations of the Fab proteins can be determined by ELISA and SDS-PAGE electrophoresis using a Fab of known concentration (as determined by amino acid analysis) as a standard. Kinetic association rates ($K_{on}$) and dissociation rates ($K_{off}$) can be obtained simultaneously by fitting the data to a 1:1 Langmuir binding model (Karlsson, R. Roos, H. Fagerslam, L. Petersson, B. (1994). Methods Enzymology 6.99-110) using the BIAevaluation program. Equilibrium dissociation constant (KD) values can be calculated as $K_{off}/K_{on}$. This protocol is suitable for use in determining binding affinity of an antibody to any S1P, including human S1P, S1P of another vertebrate (in some aspects, mammalian) (such as mouse S1P, rat S1P, primate S1P).

In some aspects of the present invention, the anti-S1P antibody binds human S1P, and does not significantly bind an S1P from another vertebrate species (in some aspect, mammalian). In some aspects, the antibody binds human S1P as well as one or more S1P from other vertebrate species (in some aspects, mammalian). In some aspects, the antibody binds to a mammalian species of S1P, such as horse or dog, but does not significantly bind to S1P from anther mammalian species. The same criteria of this paragraph can apply to other antibodies such as anti-S1P receptor antibodies.

The epitope(s) can be continuous or discontinuous. In one aspect, the antibody binds essentially the same S1P epitopes as described in U.S. patent application Ser. No. 20070148168; U.S. Pat. Nos 6,881,546 and 6,858,383; and U.S. patent application Ser. No. 10/029,372; U.S. patent application Ser. Nos. 60/854,971 and 11/924,890 and corresponding PCT application PCT/US2007/082647. It is understood that although the epitopes described above relate to mouse and human S1P, one of ordinary skill can align the structures of mouse and human S1P with the S1P of other species and identify likely counterparts to these epitopes.

The anti-S1P antagonist or S1P receptor antagonist antibodies may be made by any method known in the art. The route and schedule of immunization of the host animal are generally in keeping with established and conventional techniques for antibody stimulation and production, as further described herein. General techniques for production of human and mouse antibodies are known in the art and are described herein.

It is contemplated that any mammalian subject, including humans, or antibody producing cells therefrom, can be manipulated to serve as the basis for production of mammalian, including human, hybridoma cell lines. Typically, the host animal is inoculated intraperitoneally, intramuscularly, orally, subcutaneously, intraplantar, and intradermally with an amount of immunogen, including as described herein.

Hybridomas can be prepared from the lymphocytes and immortalized myeloma cells using the general somatic cell hybridization technique of Kohler, B. and Milstein, C. (1975) Nature 256:495-497 or as modified by Buck, D. W., et al., In Vitro, 18:377-381 (1982). Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells can be separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the anti-S1P or anti-S1P receptor monoclonal antibodies of the subject invention. The hybridomas can be expanded and subcloned, if desired, and supernatants can be assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce monoclonal antibodies specific for S1P, S1P receptor, or portions thereof.

Hybridomas that produce such antibodies may be grown in vitro or in vivo using known procedures. The monoclonal antibodies produced therefrom may be isolated from the culture media or body fluids, by conventional immunoglobulin purification procedures such as ammonium sulfate precipitation, gel electrophoresis, dialysis, chromatography, and ultrafiltration, if desired. Undesired activity, if present, can be removed, for example, by running the preparation over adsorbents made of the immunogen attached to a solid phase and eluting or releasing the desired antibodies from the immunogen. Immunization of a host animal with S1P conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glutaraldehyde, succinic anhydride, SOCh, or R'N=C=NR, where R and R' are different alkyl groups, can yield a population of antibodies (e.g., monoclonal antibodies).

If desired, the anti-S1P antibody or anti-S1P receptor antibody (monoclonal or polyclonal) of interest may be sequenced and the polynucleotide sequence may be cloned into a vector for expression or propagation. The sequence encoding the antibody of interest may be maintained in vector in a host cell and the host cell can then be expanded and frozen for future use. In an alternative, the polynucleotide sequence may be used for genetic manipulation to "humanize" the antibody or to improve the affinity, or other characteristics of the antibody. For example, if appropriate, the constant region may be engineered to mimic human constant regions to avoid immune response if the antibody is used in clinical trials and treatments in humans. It may be desirable to genetically manipulate the antibody sequence to obtain greater affinity to S1P and greater efficacy in inhibiting S1P. It will be apparent to one of skill in the art that one or more polynucleotide changes can be made to the anti-S1P antibody or anti-S1P receptor antibody and still maintain its binding affinity for S1P and S1P receptor, respectively.

Humanization of a monoclonal antibody can be achieved as follows: (1) determine the nucleotide and predicted amino acid sequence of the starting antibody light and heavy variable domains (2) design the humanized antibody, i.e., decide which antibody framework region to use during the humanizing process (3) apply humanizing methodologies/techniques and (4) transfection and expression of the humanized antibody. See, for example, U.S. Pat. Nos. 4,816,567; 5,807,715; 5,866,692; 6,331,415; 5,530,101; 5,693,761; 5,693,762; 5,585,089; and 6,180,370.

A number of "humanized" antibody molecules comprising an antigen-binding site derived from a non-human immunoglobulin have been described, including chimeric antibodies having rodent or modified rodent V regions and their associated complementarity determining regions (CDRs) fused to human constant domains. See, for example, Winter et al. Nature 349:293-299 (1991), Lobuglio et al. Proc. Nat. Acad. Sci. USA 86:4220-4224 (1989), Shaw et al. J. Immunol. 138:4534-4538 (1987), and Brown et al. Cancer Res. 47:3577-3583 (1987). Other references describe rodent CDRs grafted into a human supporting framework region (FR) prior to fusion with an appropriate human antibody constant domain. See, for example, Riechmann et al. Nature 332:323-327 (1988), Verhoeyen et al. Science 239: 1534-1536 (1988), and Jones et al. Nature 321:522-525 (1986). Another reference describes rodent CDRs supported by recombinantly veneered rodent framework regions. See, for example, European Patent Publication No. 0519596. These "humanized" molecules are designed to minimize unwanted immunological response toward rodent anti-human antibody molecules which limits the duration and effectiveness of therapeutic applications of those moieties in human recipients. For example, the antibody constant region can be engineered such that it is immunologically inert (e.g., does not trigger complement lysis). See, e.g. PCT Publication No. PCT/GB99/01441; UK Patent Application No. 9809951.8. Other methods of humanizing antibodies that may also be utilized are disclosed by Daugherty et al., Nucl. Acids Res. 19:2471-2476 (1991) and in U.S. Pat. Nos. 6,180,377; 6,054,297; 5,997,867; 5,866,692; 6,210,671; and 6,350,861; and in PCT Publication No. WO 01/27160. LT1009 is an example of a humanized antibody.

In yet another alternative, fully human antibodies may be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse™ from Abgenix, Inc. (Fremont, Calif.) and HuMAb-Mouse® and TC Mouse™ from Medarex, Inc. (Princeton, N.J.).

In an alternative, antibodies may be made recombinantly and expressed using any method known in the art. For example, antibodies may be made recombinantly by phage display technology. See, for example, U.S. Pat. Nos. 5,565,332; 5,580,717; 5,733,743; and 6,265,150; and Winter et al., Annu Rev. Immunol. 12:433-455 (1994). Alternatively, the phage display technology (McCafferty et al., Nature 348: 552-553 (1990>> can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M 13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for review see, e.g., Johnson, Kevin S, and Chiswell, David J., Current Opinion in Structural Biology 3:564-571 (1993). Several sources of V-gene segments can be used for phage display. Clackson et al., Nature 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Mark et al., J. Mol. Biol. 222:581-597 (1991), or Griffith et al., EMBO J. 12:725-734 (1993). In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling." Marks, et al., Bio/Techno!. 10:779-783 (1992)). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the pM-nM range. A strategy for making very large phage antibody repertoires (also known as "the mother-of-all libraries") has been described by Waterhouse et al., Nucl Acids Res. 21:2265-2266 (1993). Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable regions capable of restoring a functional antigen-binding site, i.e., the epitope governs (imprints) the choice of partner. When the process is repeated in order to replace the remaining rodent V domain, a human antibody humanization of rodent antibodies by CDR grafting, this technique provides completely human antibodies, which have no framework or CDR residues of rodent origin.

It is apparent that although the above discussion pertains to humanized antibodies, the general principles discussed are applicable to customizing antibodies for use, for example, in dogs, cats, primate, equines and bovines. It is further apparent that one or more aspects of humanizing an antibody described herein may be combined, e.g., CDR grafting, framework mutation and CDR mutation.

Antibodies may be made recombinantly by first isolating the antibodies and antibody producing cells from host animals, obtaining the gene sequence, and using the gene sequence to express the antibody recombinantly in host cells (e.g., CHO cells). Another method which may be employed is to express the antibody sequence in plants (e.g., tobacco) or transgenic milk. Methods for expressing antibodies recombinantly in plants or milk have been disclosed. See, for example, Peeters, et al. Vaccine 19:2756 (2001); Lonberg, N. and D. Huszar Int. Rev. Immunol. 13:65 (1995); and Pollock, et al., J Immunol Methods 231:147 (1999).
Methods for Making Derivatives of Antibodies, E.G., Humanized, Single Chain, Etc. are Known in the Art.

Immunoassays and flow cytometry sorting techniques such as fluorescence activated cell sorting (FACS) can also be employed to isolate antibodies that are specific for S1P or S1P receptor.

The antibodies according to the present invention can be bound to different carriers if desired. Carriers can be active and inert. Examples of well-known carriers include polypropylene, polystyrene, polyethylene, dextran, nylon, amylases, glass, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation. In some aspects, the carrier comprises a moiety that targets the myocardium. DNA encoding the monoclonal antibodies can be readily isolated and sequenced using conventional procedures. Hybridoma cells serve as a preferred source of such DNA. Once isolated, the DNA may be cloned into expression vectors which are then transfected into host cells such as E. coli cells, simian COS cells, Chinese hamster ovary (CHO) cells, or myeloma cells that do not otherwise produce immunoglobulin protein, for purposes of synthesizing monoclonal antibodies. See, e.g., PCT Publication No. WO 87/04462. The DNA also may be modified, for example, by substituting human heavy and light chain constant domains in place of the homologous murine sequences, Morrison et al., Proc. Nat. Acad. Sci. 81:685 J (1984), or by covalently joining to the immunoglobulin coding sequence all or part of the coding sequence for a non-immunoglobulin polypeptide. In that manner, "chimeric" or "hybrid" antibodies are prepared that have the binding specificity of an anti-S1P monoclonal antibody herein.

Anti-S1P antibodies or anti-S1P receptor antibodies may be characterized using methods well known in the art. For example, one method is to identify the epitope to which it binds, or "epitope mapping." There are many methods known in the art for mapping and characterizing the location of epitopes on proteins, including solving the crystal structure of an antibody-antigen complex (e.g., Protein Data Bank ID No. 319G), competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which an anti-S1P antibody or anti-S1P receptor antibody binds. Epitope mapping is commercially available from various sources, for example, Pepscan Systems (Edelhertweg 15, 8219 PH Lelystad, The Netherlands). The epitope can be a linear epitope, i.e., contained in a single stretch of amino acids, or a conformational epitope formed by a three-dimensional interaction of amino acids that may not necessarily be contained in a single stretch. Peptides of varying lengths (e.g., at least 4-6 amino acids long) can be isolated or synthesized (e.g., recombinantly) and used for binding assays with an anti-S1P antibody or anti-S1P receptor antibody.

Yet another method which can be used to characterize an anti-S1P antibody or anti-S1P receptor antibody is to use competition assays with other antibodies known to bind to the same antigen (e.g. LT1009 in the case of an anti-S1P antibody) to determine if the anti-S1P antibody or anti-S1P receptor antibody binds to the same epitope as other antibodies. Competition assays can be carried out using well known methods to those of skill in the art.

In one embodiment, an expression vector can be used to direct the expression of an anti-S1P antibody or anti-S1P receptor antibody in vivo, including for therapeutic purposes in a patient in need thereof. One skilled in the art is familiar with administration of expression vectors to obtain expression of an exogenous protein in vivo. See, e.g., U.S. Pat. Nos. 6,436,908; 6,413,942; and 6,376,471. Administration of expression vectors includes local or systemic administration, including injection, oral administration, particle gun or catheterized administration, and topical administration. In another aspect, the expression vector is administered directly to the sympathetic trunk or ganglion, or into a coronary artery, atrium, ventricle, or pericardium.

Targeted delivery of therapeutic compositions containing an expression vector, or subgenomic polynucleotides can also be used. Receptor-mediated DNA delivery techniques are described in, for example, Findeis et al., Trends Biotechnol. (1993) 11:202; Chiou et al., Gene Therapeutics: Methods And Applications Of Direct Gene Transfer (1. A. Wolff, ed.) (1994); Wu et al., J. Biol. Chem. (1988) 263:621; Wu et al., J. Biol. Chem. (1994) 269:542; Zenke et al., Proc. Natl. Acad. Sci. USA (1990) 87:3655; Wu et al., J. Biol. Chem. (1991) 266:338. Therapeutic compositions containing a polynucleotide are administered in a range of about 100 ng to about 200 mg of DNA for local administration in a gene therapy protocol. Concentration ranges of about 500 ng to about 50 mg, about 1 μg to about 2 mg, about 5 μg to about 500 μg, and about 20 μg to about 100 μg of DNA can also be used during a gene therapy protocol. The therapeutic polynucleotides and polypeptides can be delivered using gene delivery vehicles. The gene delivery vehicle can be of viral or non-viral origin (see generally, Jolly, Cancer Gene Therapy (1994) 1:51; Kimura, Human Gene Therapy (1994) 5:845; Connelly, Human Gene Therapy (1995) 1:185; and Kaplitt, Nature Genetics (1994) 6:148). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther. (1992) 3: 147 can also be employed.

Non-viral delivery vehicles and methods can also be employed, including, but not limited to, polycationic condensed DNA linked or unlinked to killed adenovirus alone (see, e.g., Curiel, Hum. Gene Ther. (1992) 3:147); ligand-linked DNA (see, e.g., Wu, J. Biol. Chem. (1989) 264:16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP 0524968. Additional approaches are described in Philip, Mol. Cell. Biol. (1994) 14:2411, and in Woffendin, Proc. Natl. Acad. Set (1994) 91:1581.

Non-Antibody Sphingosine Kinase Antagonists, S1P Antagonists and S1P Receptor Antagonists In another aspect of the present invention, sphingosine kinase antagonists, S1P antagonists or S1P receptor antagonists other than anti-S1P antibodies or anti-S1P receptor antibodies may be used. In some aspects of the invention, the sphingosine kinase antagonist, S1P antagonist or S1P receptor antagonist comprises at least one antisense molecule capable of blocking or decreasing the expression of at least one S1P activity. Nucleotide sequences of the sphingosine kinase and S1P receptors, including S1 P1, are known and are readily available from publicly available databases. It is routine to prepare antisense oligonucleotide molecules that will specifically bind sphingosine kinase or S1P receptor mRNA without cross-reacting with other polynucleotides. Exemplary sites of targeting include, but are not limited to, the initiation codon, the 5' regulatory regions, the coding sequence and the 3' untranslated region. In some aspects, the oligonucleotides are about 10 to 100 nucleotides in length, about 15 to 50 nucleotides in length, about 8 to 25 nucleotides in length, or more. The oligonucleotides can comprise backbone modifications such as, for example, phosphorothioate linkages, and 2'-0 sugar modifications well know in the art.

Alternatively, S1P expression and release and S1P receptor expression can be decreased using gene knockdown, morpholino oligonucleotides, RNAi, or ribozymes, methods that are well-known in the art.

In other aspects, the sphingosine kinase antagonist, S1P antagonist or S1P receptor antagonist comprises at least one sphingosine kinase, S1P and S1P receptor inhibitory compound. As used herein, "inhibitory compound" refers to a compound other than an antibody that directly or indirectly reduces, inhibits, neutralizes, or abolishes biological activity of specific targets, sphingosine kinase, S1P or S1P receptor. A sphingosine kinase, S1P or S1P receptor inhibitory compound should exhibit any one or more of the following characteristics: (a) bind to at least one of said targets, sphingosine kinase, S1P, or S1P receptor and inhibit target biological activity and downstream pathways mediated by a S1P function; (b) prevent, ameliorate, or treat any aspect of neuropathic pain (such as cancer pain), inflammatory pain or hyperalgesia; (c) block or decrease S1P receptor activation (including S1P1 receptor dimerization and phosphorylation); and (d) increase clearance of S1P.

In some aspects, an S1P inhibitory compound binds S1P. Exemplary sites of targeting (binding) include, but are not limited to, the portion of the S1P that binds to a S1P receptor, and those portions of the S1P that are adjacent to the receptor-binding region and which are responsible, in part, for the connect three-dimensional shape of the receptor-binding portion. In another aspect, an S1P inhibitory compound binds an S1P receptor (such as S1P1 receptor) and inhibits an S1P biological activity. In other aspects, an S1P inhibitory compound binds sphingosine kinase to inhibit S1P biological activity.

In some aspects, an S1P inhibitory compound is a small molecule. A small molecule can have a molecular weight of about any of 100 to 20,000 daltons, 500 to 15,000 daltons, or 1000 to 10,000 daltons. Libraries of small molecules are commercially available. Small molecule inhibitors can be administered using any means known in the art, including inhalation, intraperitoneally, intravenously, intramuscularly, subcutaneously, intrathecally, intraventricularly, orally, enterally, parenterally, intranasally, or dermally. In general, when a sphingosine kinase antagonist, S1P antagonist, or S1P receptor antagonist according to the invention is a small molecule, it will be administered at a dose of 0.1 to 300 mg/kg of the weight of the patient divided into one to three or more doses. For an adult patient, doses ranging from 1 mg to 5 g per dose can be administered.

In other aspects, the sphingosine kinase antagonist, S1P antagonist, or S1P1 receptor antagonist comprises at least one S1P structural analog. "S1P structural analogs" in the present invention refer to compounds that have a 3-dimensional structure that is similar to at least a part of that of S1P and which bind to a sphingosine kinase or S1P receptor under physiological conditions in vitro or in vivo, wherein the binding of the analog at least partially inhibits an S1P biological activity, or S1P secondary messenger activity. In one aspect, the S1P structural analog binds to an S1P1 receptor. Suitable S1P structural analogs can be designed and synthesized through molecular modeling of S1P-receptor binding, for example by the method described in PCT Publication No. WO 98/06048.

Targeted delivery of therapeutic compositions containing an antisense polynucleotide, expression vector, or subgenomic polynucleotides can also be used according to the present invention. Receptor-mediated DNA delivery techniques are described in, for example, Findeis et al., Trends Biotechnol. (1993) 11:202; Chiou et al., Gene Therapeutics: Methods And Applications Of Direct Gene Transfer (1. A. Wolff, ed.) (1994); Wu et al., J. Biol. Chem. (1988) 263:621; Wu et al., J. Biol. Chem. (1994) 269:542; Zenke et al., Proc. Natl. Acad. Sci. USA (1990) 87:3655; Wu et al., J. Biol. Chem. (1991) 266:338. Therapeutic compositions containing a polynucleotide are administered in a range of about 100 ng to about 200 mg of DNA for local administration in a gene therapy protocol. In some aspects, concentration ranges of about 500 ng to about 50 mg, about 1 µg to about 2 mg, about 5 µg to about 500 µg, and about 20 µg to about 100 µg of DNA or more can also be used during a gene therapy protocol.

Therapeutic polynucleotides and polypeptides of the present invention can be delivered using gene delivery vehicles. The gene delivery vehicle can be of viral or non-viral origin {see generally, Jolly, Cancer Gene Therapy (1994) 1:51; Kimura, Human Gene Therapy (1994) 5:845; Connelly, Human Gene Therapy (1995) 1: 185; and Kaplitt, Nature Genetics (1994) 6: 148). Expression of such coding sequences can be controlled using endogenous mammalian or heterologous promoters and enhancers to achieve constitutive or regulated expression.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO'93/11230; WO 93/10218; WO 91/02805; U.S. Pat. Nos. 5,219,740 and 4,777,127; GB Patent No. 2,200,651; and EP Patent No. 0345242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95111984 and WO 95/00655). Administration of DNA linked to killed adenovirus as described in Curiel, Hum. Gene Ther. (1992) 3:147 can also be employed.

Non-viral delivery vehicles and methods can also be employed, including, but not limited to, polycationic condensed DNA linked or unlinked to killed adenovirus alone {see, e.g., Curiel, Hum, Gene Ther. (1992) 3:147); ligand-linked DNA {see, e.g., Wu, J. Biol. Chem. (1989) 264:16985); eukaryotic cell delivery vehicles cells {see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP Patent No. 0524968. Additional approaches are described in Philip, Mol. Cell. Biol. (1994) 14:2411, and in Woffendin, Proc. Natl. Acad. Sci. (1994) 91:1581.

It is also apparent that an expression vector can be used to direct expression of any of the protein-based sphingosine kinase antagonists, S1P antagonists or S1P receptor antagonists described herein (e.g., anti-S1P antibody).

S1P Receptor Agonists

In a further aspect, the invention provides therapeutic methods that use an S1P receptor agonist, which refers to any molecule that induces S1P receptor biological activity, including downstream pathways mediated by S1P signaling, such as receptor binding and elicitation of a cellular response to S1P. Without being bound to any particular theory, it appears that S1P receptor agonists cause internalization and degradation of S1P receptors so that they cannot recycle, resulting in an effective treatment for neuropathic pain (including cancer pain or chemotherapy-induced pain), inflammatory pain, hypersensitivity, and antinociceptive tolerance. Accordingly, in this aspect, the invention provides methods of treating neuropathic pain, inflammatory pain, hypersensitivity, and antinociceptive tolerance in an individual comprising administering an effective amount of an S1P receptor agonist.

The term "agonist" implies no specific mechanism of biological action, and is deemed to expressly include and encompass all possible pharmacological, physiological, and biochemical interactions with the S1P receptor and its consequences which can be achieved by a variety of different, and chemically divergent, compositions. In one aspect, the S1P receptor agonists are sphingosine and S1P structural analogs which bind to an S1P receptor under physiological conditions in vitro or in vivo, wherein the binding exerts an agonistic effect on the S1P receptor. Agonists of all types of S1P receptors, such as S1P [1-5] are acceptable, but those of S1P1 are preferred. S1P structural analogs are believed to bind to the S1P binding site of S1P receptors. However, agonists may bind at sites other than the S1P binding site, provided such binding results in an agonistic effect.

Example agonists include, but are not limited to, Fingolimod (codenamed FTY720, trade name Gilenya™, Novartis Pharma AG, New York), BAF312 (Novartis Pharma AG, New York), Ponesimod (ACT-128800, Actelion Ltd., Switzerland), ONO-4641 (Ono Pharma, Japan), CS-0777 (Daiichi Sankyo, Japan), KRP-203 (Kyorin, Japan), PF-991 (Pfizer, New York), and W146 (Cayman Chemical, Michigan) (Brinkmann et al. (2010) Nat. Rev. 9: November 2010: 883-897; Hla T. et al. (2011) Neurology 2011; 76; 53; Cusack et al. (2010) Curr. Op. in Dr. Disc. and Dev. 13 (4): 481-488; Strader et al. (2011) J. Nat. Prod. 2011, 74, 900-907). Fingolimod is particularly preferred.

In aspects where the S1P receptor agonist is a small molecule, a small molecule can have a molecular weight of about any of 100 to 20,000 daltons, 500 to 15,000 daltons, or 1000 to 10,000 daltons. Libraries of small molecules are commercially available. The small molecules can be administered using any means known in the art, including inhalation, intraperitoneally, intravenously, intramuscularly, subcutaneously, intrathecally, intraventricularly, orally, enterally, parenterally, intranasally, or dermally. Usually, when the S1P receptor agonist according to the invention is a small molecule, it will be administered at the rate of 0.1 to 300 mg/kg of the weight of the patient divided into one to three or more doses. For an adult patient of normal weight, doses ranging from 1 mg to 5 g per dose can be administered.

Compositions for Use in the Methods of the Invention

The compositions used in the methods of the invention comprise an effective amount of a sphingosine kinase antagonist, S1P antagonist, S1P receptor agonist, or S1P receptor antagonist (such as an anti-S1P antibody), and, in some aspects, further comprise a pharmaceutically acceptable excipient. In some aspects, the composition is for use in any of the methods described herein. Examples of such compositions, as well as how to formulate, are also described in an earlier section and below. In one aspect, the composition comprises a sphingosine kinase antagonist, S1P antagonist, S1P receptor agonist, or S1P receptor antagonist. In another aspect, the composition comprises one or more sphingosine kinase antagonists, S1P antagonists, S1P agonists, or S1P receptor antagonists. In some aspects, the S1P antagonist, S1P agonist, or S1P receptor antagonist is not associated with an adverse immune response. In some aspects, the S1P antagonist, S1P agonist, or S1P1 receptor antagonist is selected from the group consisting of an anti-S1P antibody, anti-S1P1 receptor antibody, an anti-sense molecule directed to an S1P1 receptor (including an anti-sense molecule directed to a nucleic acid encoding S1P1 receptor), an anti-sense molecule directed to an S1P receptor (such as S1P1), and an S1P inhibitory compound, an S1P structural analog. In another aspect, the S1P antagonist or S1P1 receptor antagonist is an anti-S1P antibody. In other aspects, the anti-S1P antibody recognizes human S1P. In some aspects, the anti-S1P antibody is human. In still other aspects, the anti-S1P antibody is humanized (such as LT1009 described herein). In still other aspect, the anti-S1P antibody comprises a constant region that does not trigger an unwanted or undesirable immune response, such as antibody-mediated lysis or ADCC. In other aspects, the anti-S1P antibody comprises one or more CDR(s) of antibody LT1009 (such as one, two, three, four, five, or, in some aspects, all six CDRs from LT1009).

Compositions according to the invention can comprise more than one sphingosine kinase antagonist, S1P antagonist, S1P receptor agonist or S1P receptor antagonist. For example, a composition can comprise more than one member of a class of S1P antagonist, S1P agonist, or S1P receptor antagonist (e.g., a mixture of anti-S1P antibodies that recognize different sites of S1P or epitopes of S1P1 receptor), as well as members of different classes of S1P antagonist, S1P agonist, or S1P receptor antagonists (e.g., an anti-S1P antibody and an S1P inhibitory compound). Other exemplary compositions comprise more than one anti-S1P antibodies that recognize the same epitope(s), different species of anti-S1P antibodies that bind to different epitopes of S1P receptor or different S1P inhibitory compounds.

A composition according to the present invention can further comprise pharmaceutically acceptable carriers, excipients, or stabilizers (Remington: The Science and Practice of Pharmacy 20th Ed. (2000) Lippincott Williams and Wilkins, Ed. K. E. Hoover), in the form of lyophilized formulations or aqueous solutions. Pharmaceutically acceptable excipients are further described herein.

The sphingosine kinase antagonist, S1P antagonist, S1P agonist, or S1P receptor antagonist and compositions thereof can also be used in conjunction with other agents that serve to enhance and complement the effectiveness of said antagonists and/or agonists. For example, for the treatment of neuropathic pain, inflammatory pain, hyperalgesia, and allodynia, sphingosine kinase antagonists, S1P antagonists, S1P agonists, or S1P receptor antagonists may be administered in conjunction with one or more other analgesics, NSAIDS, or steroids. Analgesics include, but are not limited to, acetaminophen, tramadol, capsaicin (topical). Examples of NSAIDS are acetylated salicylates including aspirin; nonacetylated salicylates including salsalate, diflunisal; acetic acids including etodolac, diclofenac, indomethacin, ketorolac, nabumetone; propionic acids including fenoprofen, flurbiprofen, ibuprofen, ketoprofen, naproxen, naproxen sodium, oxaprozin; fenamates including meclofenamate, mefenamic acid; phenylbutazone, piroxicam; COX-2 inhibitors including celecoxib, etoricoxib, valdecoxib, rofecoxib, lumiracoxib. Exemplary steroids include intraarticular corticosteroids (IACs).

Kits Comprising Agonists and Antagonists of the Invention

The invention also provides kits comprising sphingosine kinase antagonists, S1P antagonists, S1P receptor agonists, S1P receptor agonists and S1P receptor antagonists for use in detection and therapy. The kits may be used for any of the methods described herein, including, for example, to treat an individual with neuropathic pain (including cancer pain and chemotherapy-induced pain), inflammatory pain, hyperalgesia, and allodynia. The kits may optionally provide additional components such as, buffers and instructions for use of an S1P receptor agonist and an antagonist, such as an antibody in any of the methods described herein. In some aspects, the kits include instructions for treating pain. In some aspects, the kit comprises an S1P agonist and an antibody described herein and instructions for treating pain, such as cancer pain, inflammatory pain and hyperalgesia, in an individual. In other aspects, the kit comprises one or more of a sphingosine kinase antagonist, S1P antagonist, S1P agonist (such as Fingolimod, BAF312, Ponesimod, ONO-4641, CS-0777, KRP-203, PF-991, and W146), or S1P receptor antagonist (such as an anti-S1P antibody or S1P1 receptor antibody) described herein and instructions for treating hyperalgesia in an individual.

EXPERIMENTS

Ceramide, a precursor in the biosynthesis of S1P, co-localizes with glia and not neurons When compared to rats that received a chronic subcutaneous (s.c) infusion of saline (Veh-Sal, n=5) over 7 days, infusion of morphine over the same time frame (Veh-Mor, n=5) led to 1) the development of thermal hyperalgesia (Hargreaves et al., 1988) as evidenced by a significant (P<0.001) reduction in paw-withdrawal latency (s) on day 3 and 6 when compared to paw-withdrawal latency from before implantation of the osmotic minipump (baseline, 1=0 h) (FIGS. 1A, C and 2) the development of antinociceptive tolerance over the same time frame (FIGS. 1B, D and 15A, B). The latter was indicated by a significant (P<0.001) reduction in tail flick latency 30 min after challenge with an acute dose of morphine (6 mg/kg) given intraperitoneally (i.p) on day 3 and 6 in rats that received chronic morphine infusion over 7 days when compared to rats that received an infusion of saline over the same time frame (FIGS. 1B, D and 15A, B).

Figure 2:
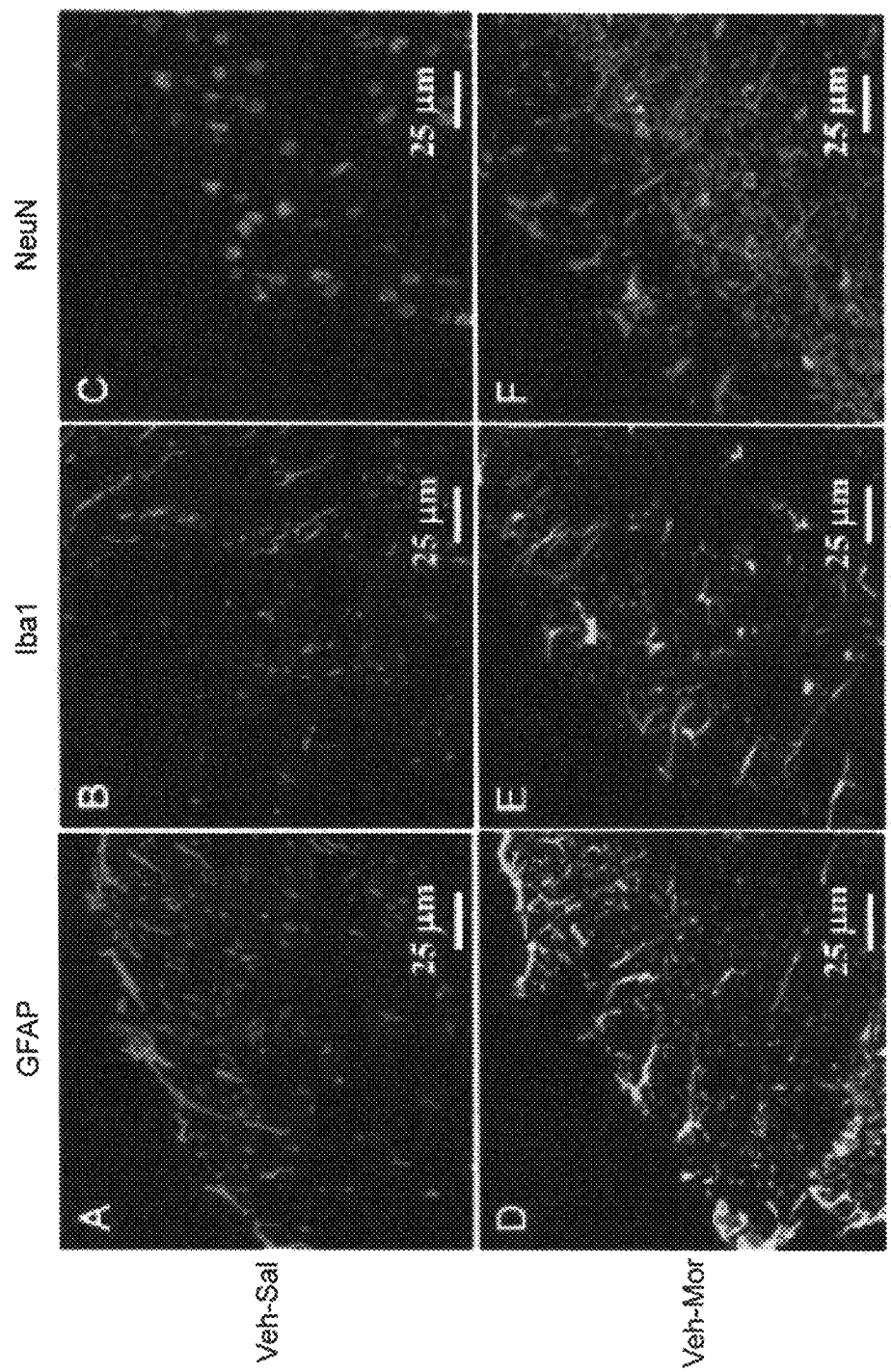
Figure 16:
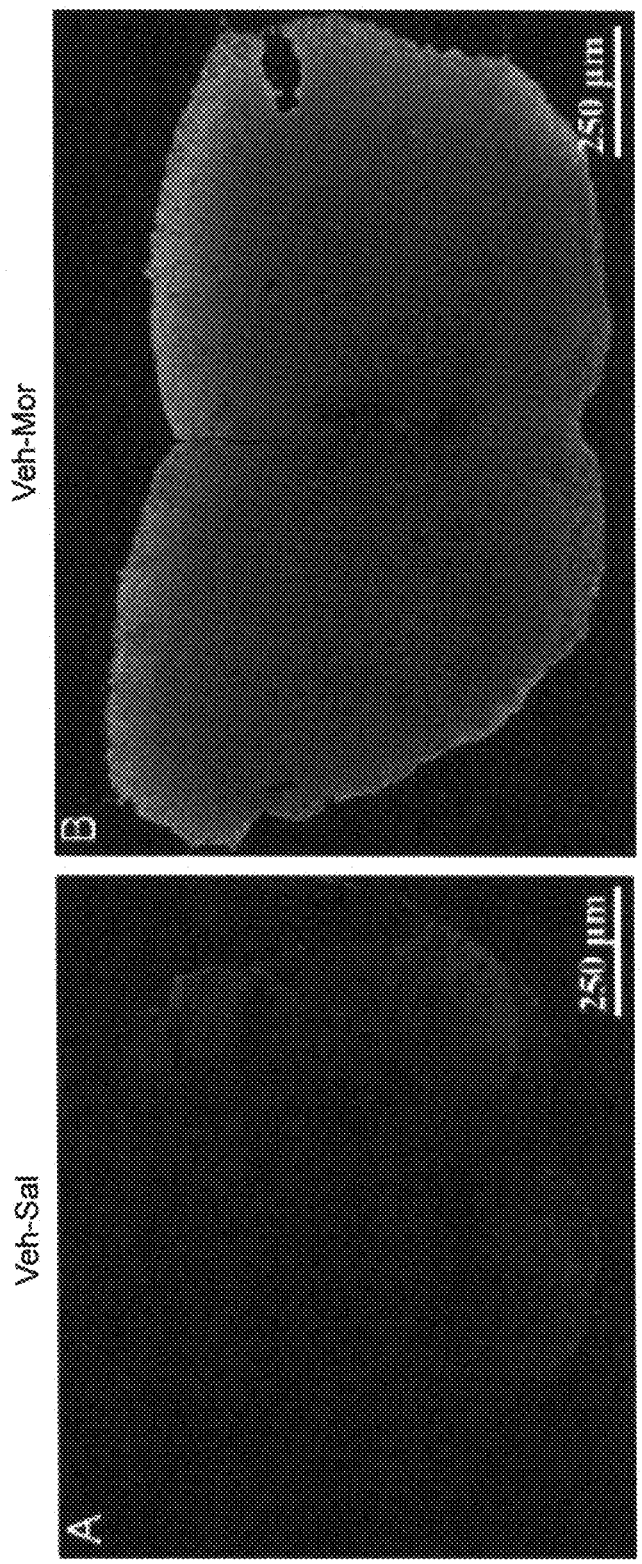
Figure 17:
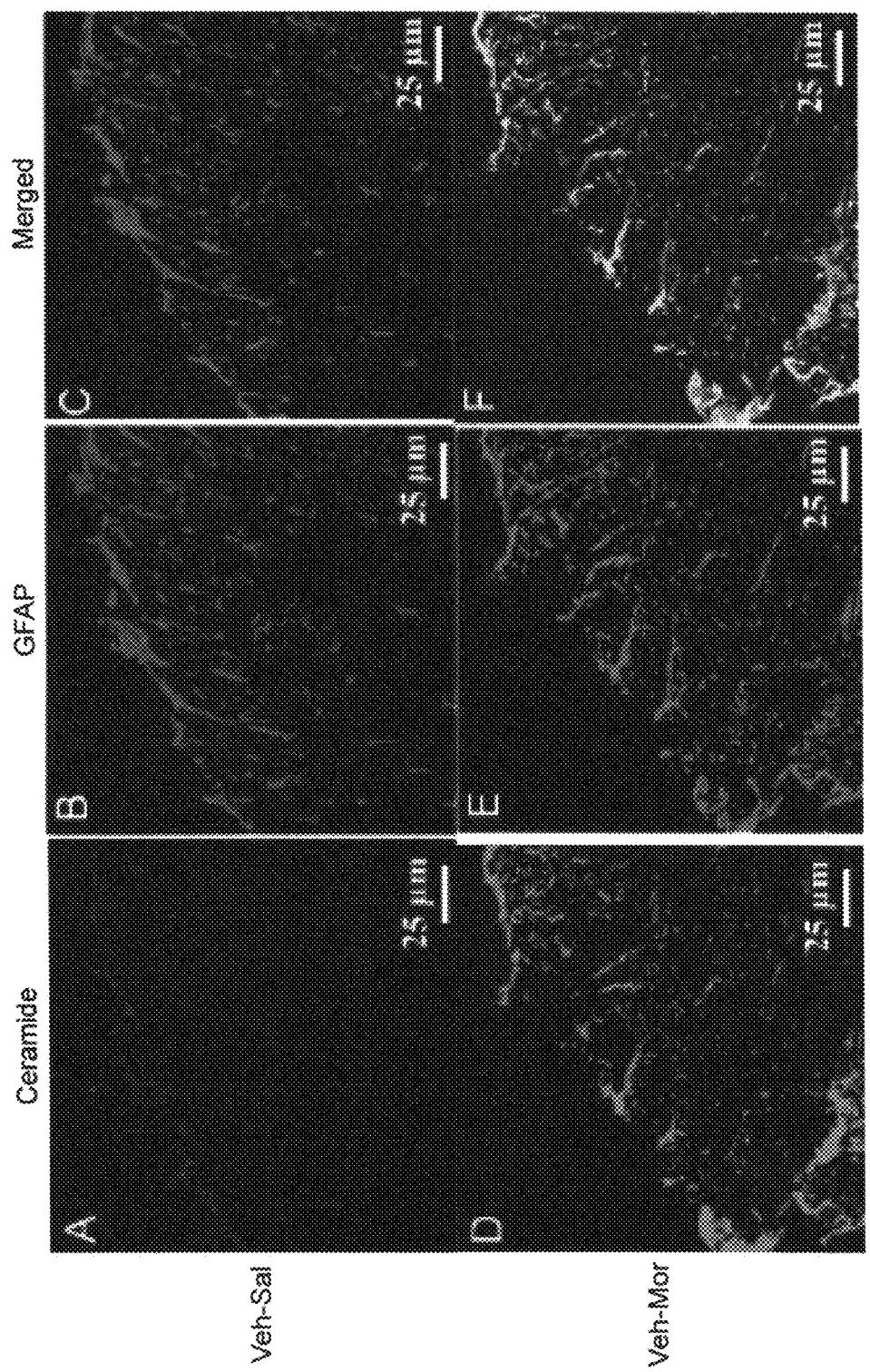
Figure 18:
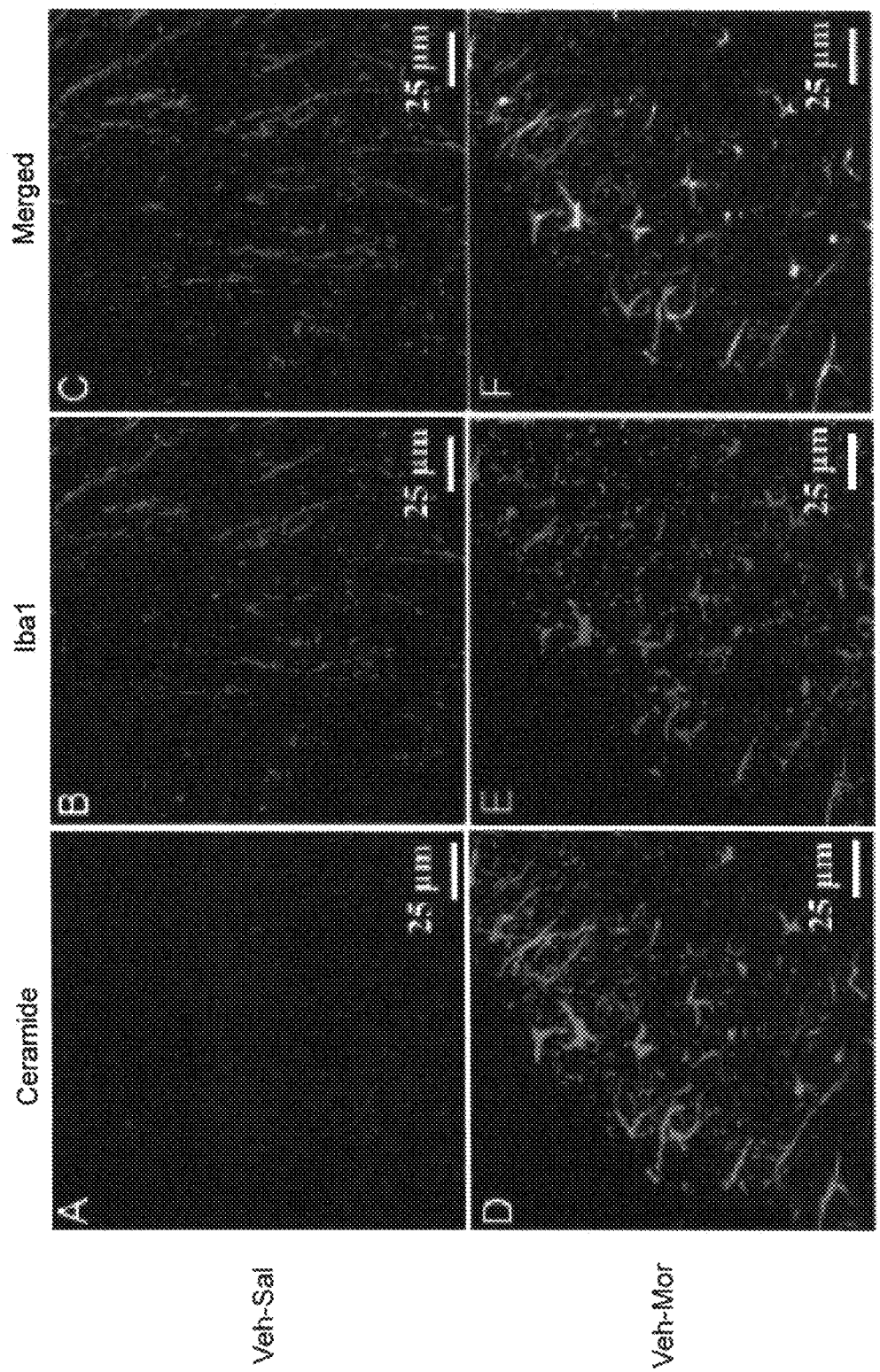
Figure 19:
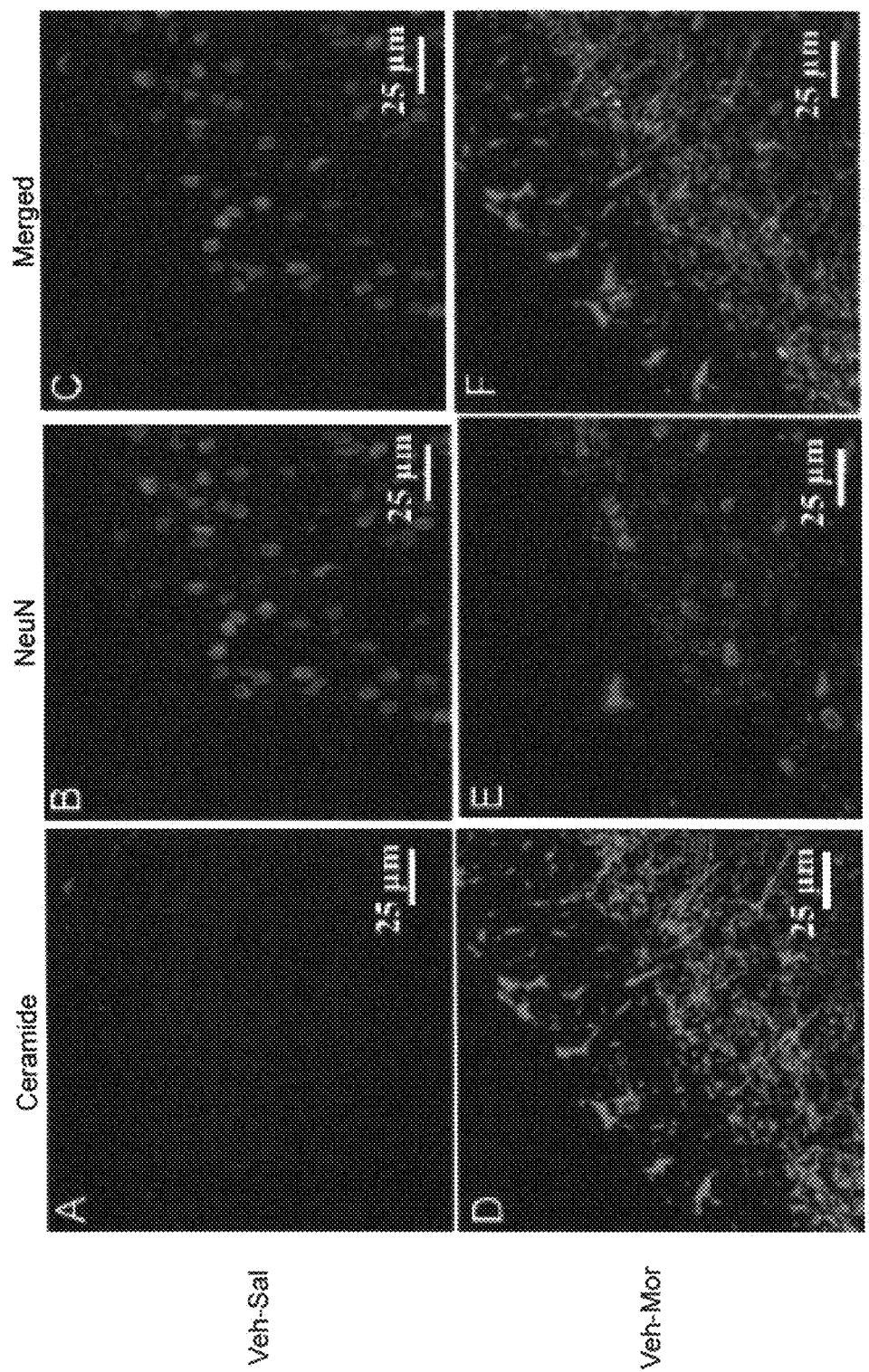
Figure 20:
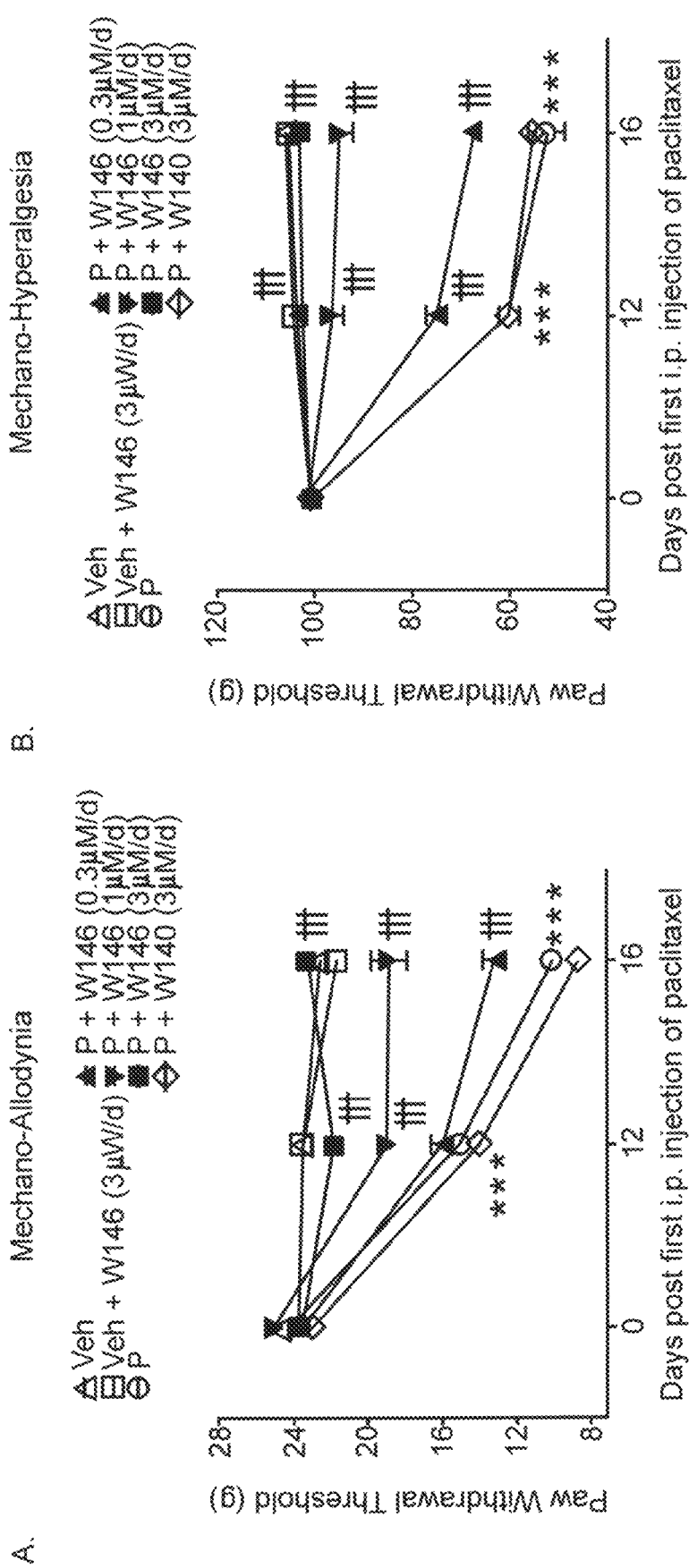
Figure 21:
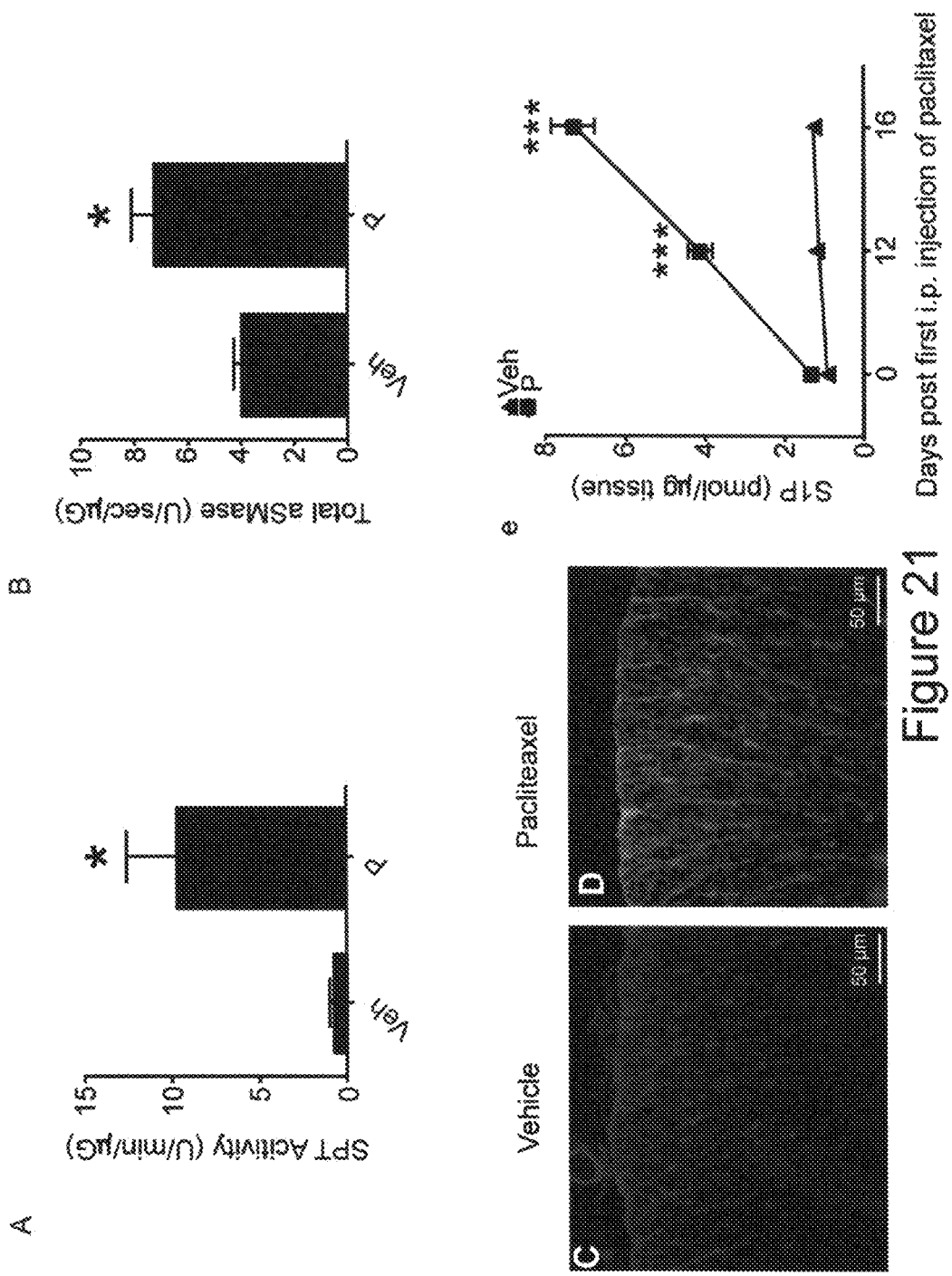
Figure 22:
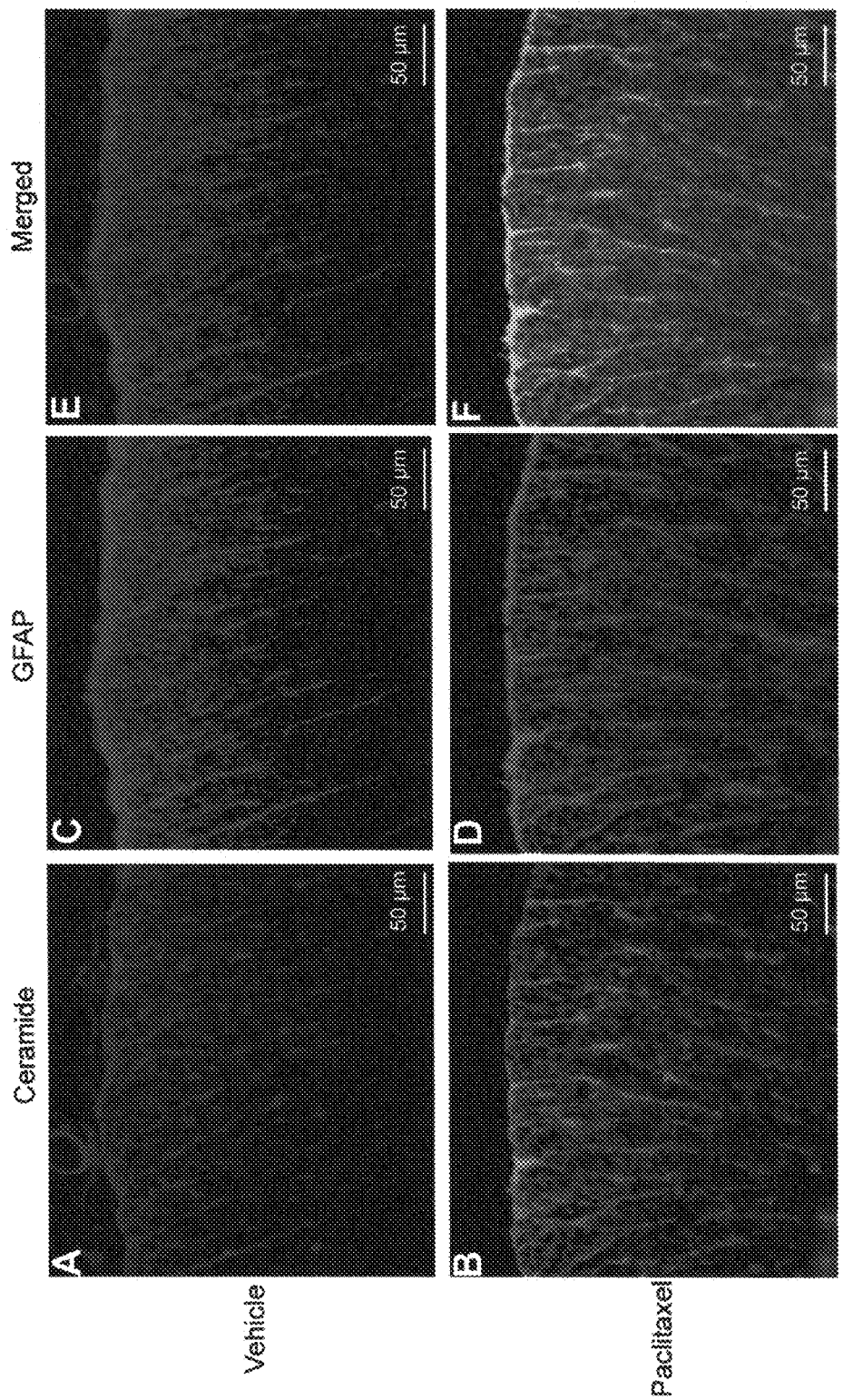
Figure 23:
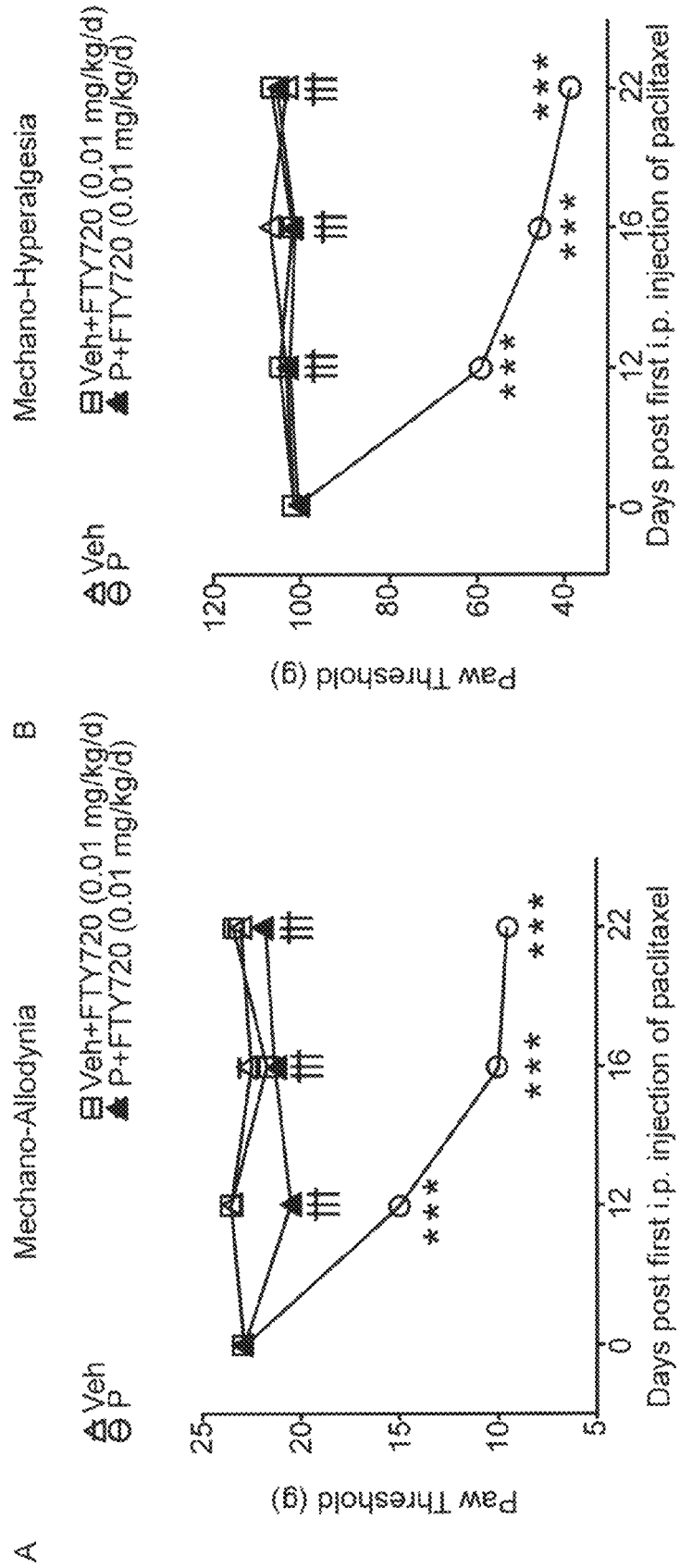
Figure 1A:
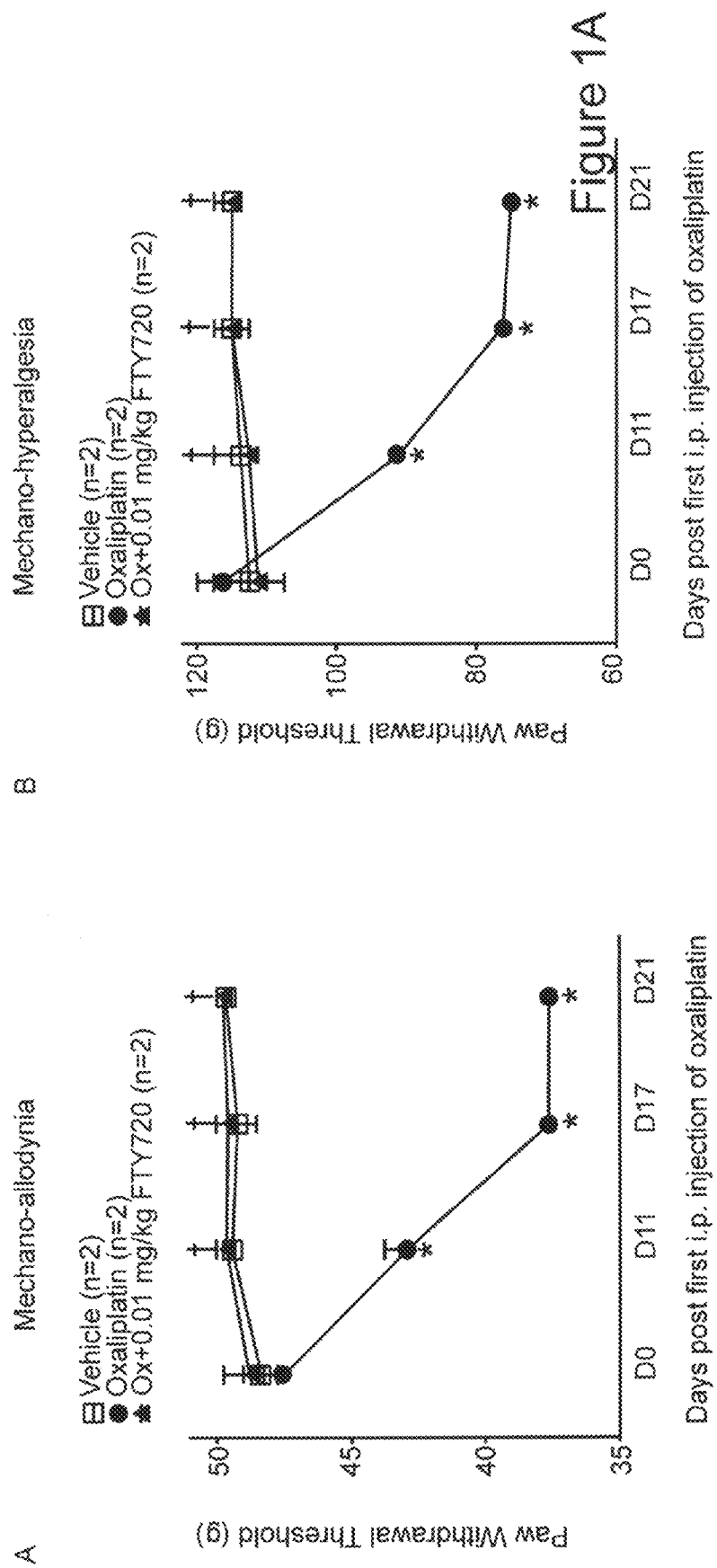

The development of morphine-induced hyperalgesia and antinociceptive tolerance observed on day 6 was associated with a significant increased formation of ceramide as detected by immunofluorescence, including in superficial layers of the spinal cord from the lumbar enlargement (L4-L6) (FIGS. 1F and 16B for a photomontage including the whole spinal dorsal horn) confirming previous studies (Ndengele et al., 2009). Interestingly, ceramide was preferentially upregulated and co-localized in astrocytes (FIG. 2D) [using GFAP, glial fibrillary acidic protein, a cellular marker for astrocytes (Romero-Sandoval et al., 2008a)] and microglial cells (FIG. 2E) [using Iba1, ionized calcium-binding adaptor molecule 1, a cellular marker for microglia (Narita et al., 2006)], but not in neurons (FIG. 2F; using NeuN, neuronal marker). Individual photos displaying single labeling are shown in FIGS. 17-19.

Figure 3:
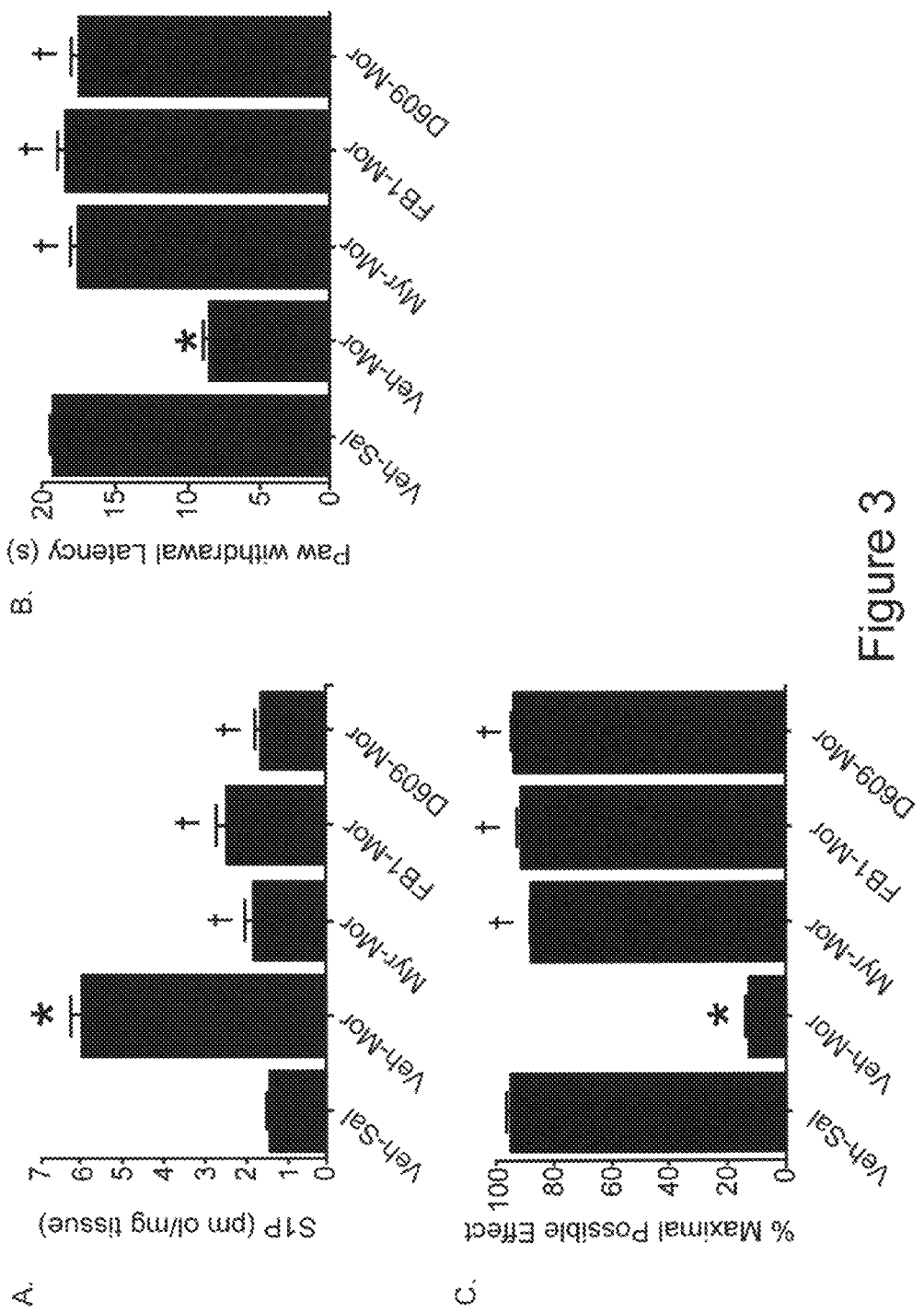
Figure 15:
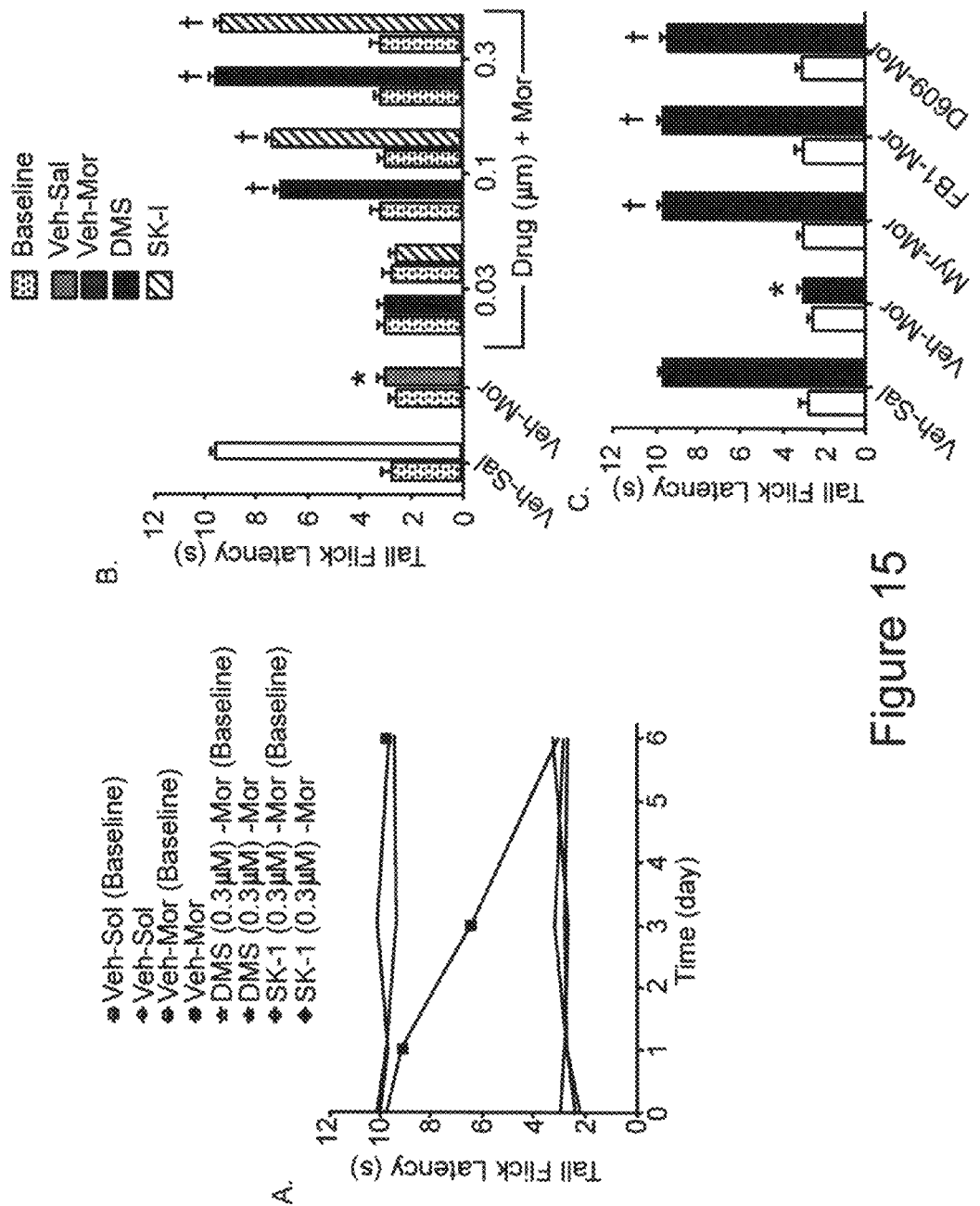

The development of morphine-induced hyperalgesia and antinociceptive tolerance observed on day 3 and 6 was associated with a significant ($P<0.001$) increased formation in S1P levels in dorsal horn tissue as measured by ELISA (Echelon Biosciences, Salt Lake City, Utah) following extraction of the sphingolipids (FIGS. 1G, H). Co-administration of morphine with daily (6 days) i.th injections of myriocin (Myr-Mor; 0.3 µM/day/6 days, n=4), an inhibitor of serine palmitoyltransferase (Delgado et al., 2006); FB1 (FB1-Mor; µM/day/6 days, n=4), a competitive and reversible inhibitor of ceramide synthase (Delgado et al., 2006), or D609 (D609-Mor; µM/day/6 days, n=4), an inhibitor of sphingomyelinase (Delgado et al., 2006) blocked the increased production of S1P (FIG. 3A) and the development of hyperalgesia (FIG. 3B) and antinociceptive tolerance (FIGS. 3C and 15C). It has been previously shown that at these doses these inhibitors effectively block the formation of ceramide in the spinal cord (Ndengele et al., 2009).

Inhibitors of S1P biosynthesis block the development of morphine-induced hyperalgesia and antinociceptive tolerance That spinally formed S1P is the key second messenger (downstream of ceramide) contributing to morphine-induced hyperalgesia and antinociceptive tolerance was established in the following studies using inhibitors of the enzymatic bioconversion of ceramide to S1P catalyzed by sphingosine kinase. As observed on day 3 and 6, co-administration of morphine with daily i.th injections of two structurally unrelated and commonly used inhibitors of sphingosine kinase, namely DMS (DMS-Mor; 0.3 µM/day, n=5) or SK-I (SK-1-Mor; 0.3 µM/day/6 days, n=5) (French et al., 2003; Lee et al., 2004; Delgado et al., 2006), blocked increased production of S1P (FIG. 1G, $P<0.001$) in dorsal horn tissues and the development of hyperalgesia (FIG. 1A, $P<0.001$) and antinociceptive tolerance (FIGS. 1B and 15A, $P<0.001$). Full dose response curves for DMS (DMS-Mor; 0.03-0.3 µM/day/6 days, n=5) or SK-I (SK-1-Mor; 0.03-0.3 µM/day/6 days, n=5) are shown at time of maximal effects (day 6) in FIG. 1E (for hyperalgesia), FIGS. 1D and 15B (for tolerance) and FIG. 1H (for S1P). These results establish the role of the sphingosine kinase to S1P signaling pathway.

When given alone daily and over 6 days to rats that received saline infusion (Veh-Sal), these drugs had no effect on any parameter tested (Table 1). When compared to rats that received a chronic s.c infusion of saline (Veh-Sal, n=5) over 7 days, infusion of Mry, FB1, D609, DMS or SK-I over the same time frame did not affect paw-withdrawal latencies, did not affect antinociceptive responses to acute morphine and did not affect S1P levels in spinal cord tissues as measured on day 6.

TABLE 1

In vivo effect of various compounds on experimental parameters.

| | Paw-Withdrawal Latency(s) | % MPE (Tail-flick) | S1P (pg/mg tissue) |
|---|---|---|---|
| Veh-Sal | 19 ± 0.5 | 93 ± 2.3 | 1.4 ± 0.10 |
| Myr-Sal | 19 ± 0.5 | 91 ± 3.0 | 1.2 ± 0.05 |
| FB1-Sal | 19 ± 0.8 | 92 ± 3.2 | 1.4 ± 0.06 |
| D609-Sal | 19 ± 0.7 | 92 ± 3.0 | 1.5 ± 0.06 |
| DMS-Veh | 19 ± 0.5 | 97 ± 3.0 | 1.7 ± 0.07 |
| SK-1-Veh | 19 ± 0.7 | 99 ± 0.9 | 1.3 ± 0.06 |

Mean ± SEM for n = 4 animals
Results are expressed as mean ± SEM for n = 5 animals.

Baseline values for tail flick latency from all groups on day 6 before injection of acute morphine, were statistically insignificant and ranged between 2-3 sec Inhibition of S1P with acute i.th injection of DMS or SK-I did not reverse tolerance once established (n=4, not shown) indicating that ceramide-derived S1P contributes to events leading to the development, but not expression of tolerance. Furthermore, since inhibition of ceramide or S1P did not inhibit acute nociception (Table 1) these mediators appear not to be involved in normal pain signaling.

Although pilot studies clearly demonstrated that catheterized animals show similar baseline nociceptive thresholds as naive animals, the possibility that chronic i.th catheters may have an effect on the spinal environment, which leads to changes in pain processing cannot be excluded. To the best of our knowledge, however, concerns of this type have not been validated. Similarly, one cannot exclude the possibility that temporary or repeated direct lumbar injections has effects on the spinal environment, which may also lead to changes in pain processing.

Figure 4:
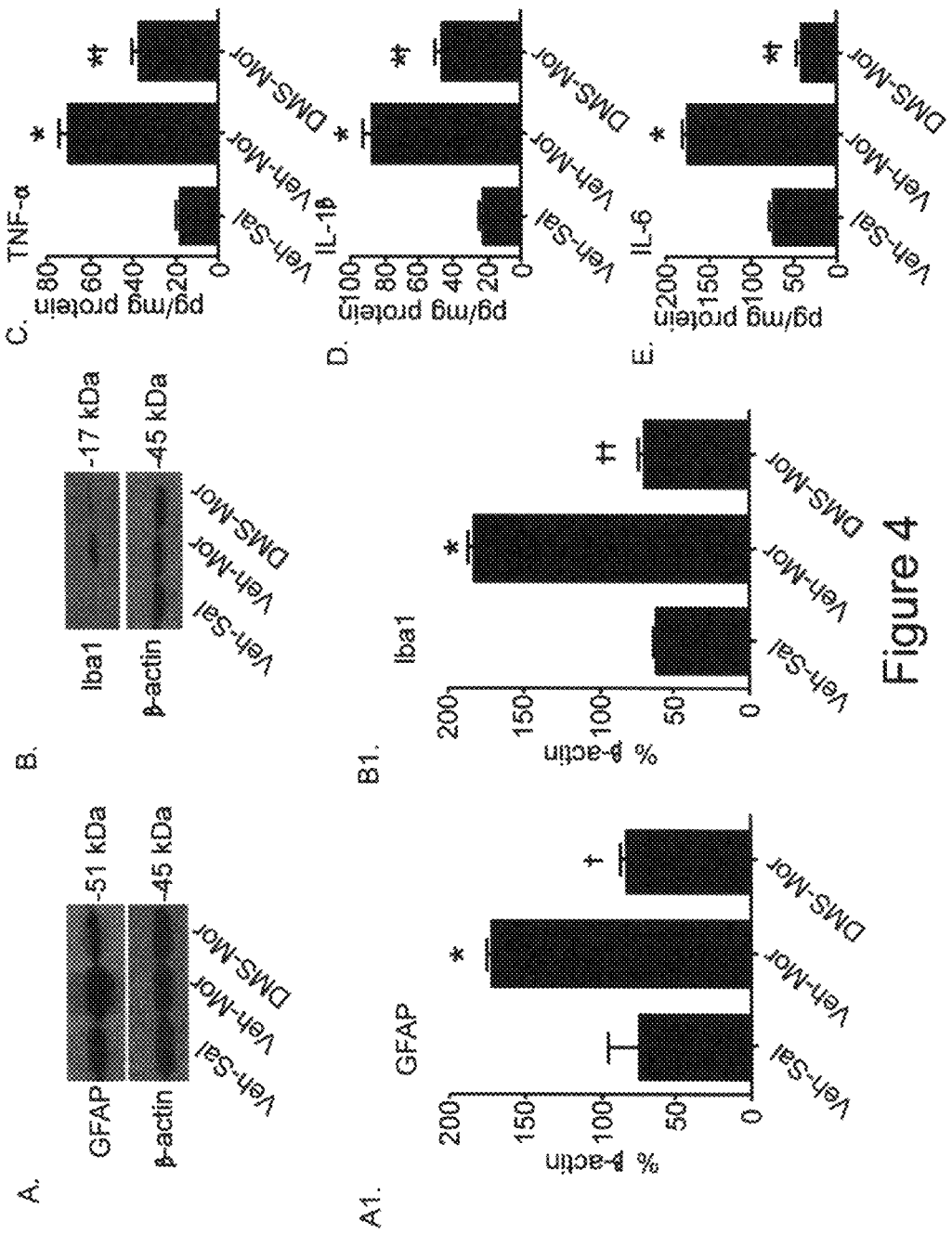

S1P Contributes to the Development of Morphine-Induced Hyperalgesia and Antinociceptive Tolerance by Increasing Formation of Glia-Related Cytokines When compared to non-tolerant animals (FIGS. 17B and 18B), the development of morphine-induced hyperalgesia and antinociceptive tolerance was associated with an inducement of expression of GFAP and Iba1 immunofluorescence, respectively, in astrocytes and microglial cells (FIGS. 17E and 18E); and in protein expression by Western blot (FIGS. 4A, A1 for GFAP and 4B, B1 for Tha1, $P<0.001$) and a significant ($P<0.001$) increase in TNF-α(X (FIG. 4C), IL-1β (FIG. 4D) and IL-6 (FIG. 4E) in dorsal horn tissues. Co-administration of morphine with i.th delivery of DMS (0.3 µM/day/6 days, n=5) significantly attenuated the DMS-induced increased glial cell expression of these markers (evidenced by decreased GFAP, $P<0.01$, and Iba1, $P<0.001$, protein expression by Western blot; FIGS. 4A, A1 for GFAP and 4B, B1 for Iba1) and increased production of TNF-α, IL-1β and IL-6 (FIG. 4C-E).

S1P Contributes to the Development of Morphine-Induced Hyperalgesia and Antinociceptive Tolerance Via Nitration of Glia-Related GLT-I and GS Peroxynitrite (PN, ONOO⁻) is an important component in the development of morphine-induced hyperalgesia and antinociceptive tolerance. Data has shown that formation of 3-nitrotyrosine (NT) in the superficial layers of the dorsal horn originates from spinal production of PN (Muscoli et al., 2007). Detection of NT in this setting can therefore be reliably used as marker of PN (Muscoli et al., 2007). It is now shown that when compared to non-tolerant rats, the appearance of NT staining in tolerant rats was blocked by co-administration of morphine with DMS (0.3 µM/day/6 days, n=5; FIGS. 5A, 5B, and 5C).

Figure 5:
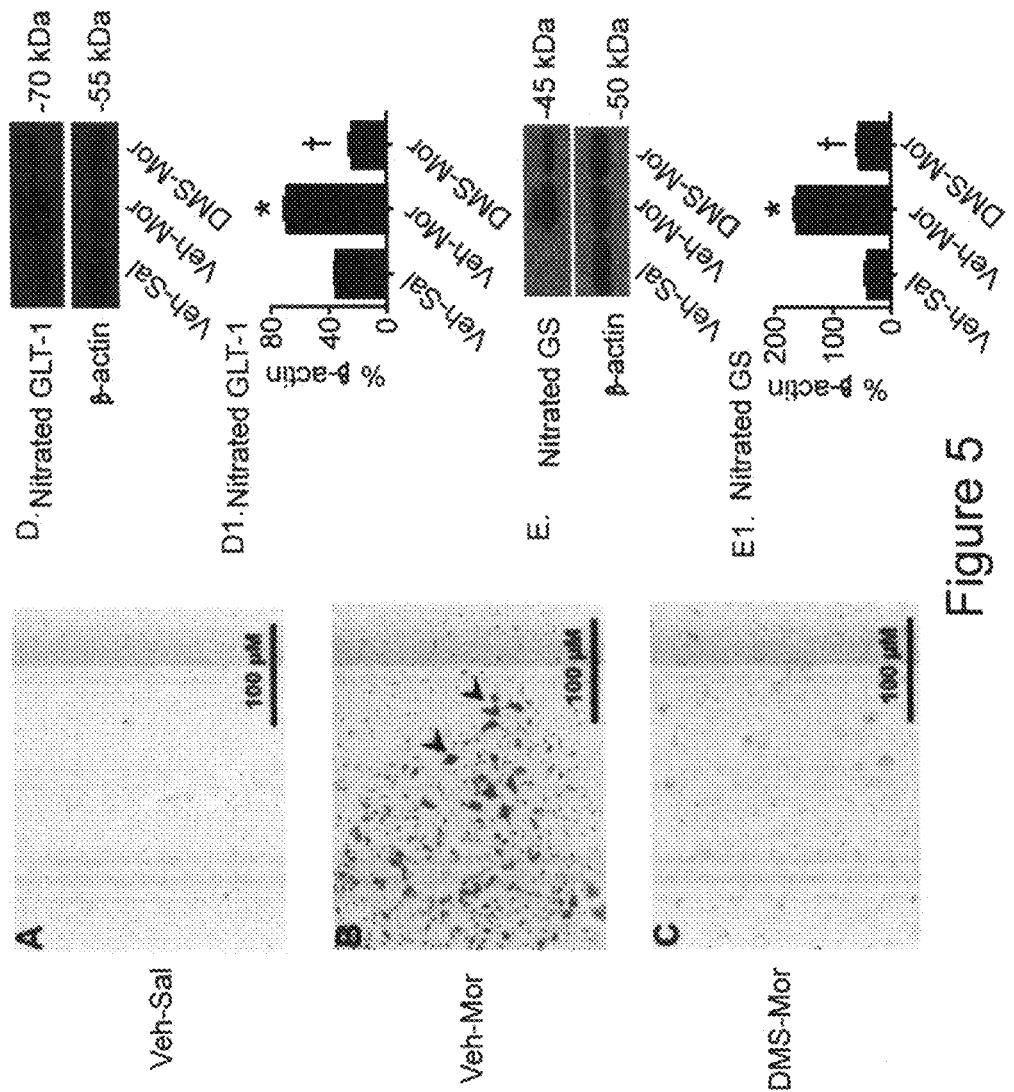

These findings provide a mechanistic link between chronic administration of morphine and increased formation of spinal PN. Two important glial cell proteins known to play essential roles in glutamate handling, and thus glutamatergic neurotransmission, namely the glutamate transporter (GLT-1) and glutamate synthetase (GS), have been found to be nitrated by PN in the spinal cord during the development of morphine-induced hyperalgesia and antinociceptive tolerance (Muscoli et al., 2007). Nitration of these proteins is intimately linked to inactivation of their biological function (Trotti et al., 1996; Minana et al., 1997; Trotti et al., 1999; Gorg et al., 2005) and their inactivation has important ramifications manifested by enhancing glutamatergic neurotransmission, which is key to central sensitization (Salvemini and Neumann, 2010). As can be seen in FIG. 5, when compared to non-tolerant animals, the development of antinociceptive tolerance and hyperalgesia was associated with nitration of GLT-1 (FIGS. 5D, D1) and GS (FIGS. 5E, E1) and this was significantly ($P<0.001$) attenuated by i.th delivery of DMS thus establishing the link between chronic morphine administration to S1P formation and PN-mediated nitration of GLT-1 and GS (FIG. 5). Total GLT-1 and GS protein levels did not change amongst the various groups (n=5, not shown).

Additional Experiments

Aspects of the present teachings may be further understood in light of the following examples, which should not be construed as limiting the scope of the present teachings in any way.

Assessment of S1P Activity and Neuropathic Pain

Material and Methods

Experimental animals. Male Sprague Dawley rats (200-250 g) were purchased from Harlan (USA and Europe) and housed 3-4 per cage and maintained in controlled environment (12 h light/dark cycle) with food and water available ad libitum. All experiments were performed in accordance with the International Association for the Study of Pain and the National Institutes of Health guidelines on laboratory animals welfare and the recommendations by Saint Louis University Institutional Animal Care and Use Committee. Animal use at the University of Magna Graecia, Catanzaro, Italy, likewise complied with Italian regulations for the protection of animals used for experimental and other scientific purpose (D.M. 116192), and with European Union regulations. All experiments were conducted with the experimenters blinded to treatment conditions.

Osmotic pump implantation. Rats, under light isoflurane anesthesia, were subcutaneously implanted (in the interscapular region) with osmotic pumps (Alzet 2001; Alza, Mountain View Calif.), to deliver saline at 1 µl/h or morphine at 75 µg µl$^{-1}$ h$^{-1}$ over 7 days as described (Vera-Portocarrero et al., 2006). Minipumps were filled according to manufacturer's specifications. The use of the osmotic pump ensures a continuous delivery of morphine avoiding intermittent periods of withdrawal. The integrity of the pump delivery system was reexamined at the end of each experiment when the spinal cords were harvested.

Drug administration. The test substances fumonisin B1 (FB 1, Sigma-Aldrich, St. Louis, Mo.), myriocin (Myr Sigma-Aldrich, St. Louis, Mo.), D609 (Tricyclodecan-9-ylxanthogenate, K; Calbiochem, San Diego, Calif.), DMS (N,N-Dimethylsphingosine, Caymen Chemical, Ann Arbor, Mich.), SK-I 2-(p-hydroxyanilino)-4-(p-chlorophenyl) thiazole, Calbiochem, San Diego, Calif.) or their vehicle (0.5% in DMSO) were delivered by intrathecal (i.th) injection in rats chronically implanted with i.th cannulas as described previously (Storkson et al., 1996). Test substances were injected i.th once a day for 6 days in a total volume of 10 µl followed by a 10 µA flush with sterile physiological saline.

Behavioral tests. Thermal hyperalgesia. The method of Hargreaves and colleagues was used to assess changes in baseline nociceptive responses to a thermal nociceptive stimulus (Hargreaves et al., 1988). Animals were allowed to acclimate within a Plexiglas enclosure on a clear glass plate in a quiet testing room. A radiant heat source is focused onto the plantar aspect of the hindpaw with baseline latencies of 18-20 sec and a maximal cutoff time of 20 sec to prevent tissue damage. The paw-withdrawal latency is determined by a motion detector activated by the paw withdrawal, stopping a timer. Foot withdrawal latencies were taken on the day before implantation of the minipumps (baseline) and subsequently on days 1, 3 and 6 of the experimental period to determine whether morphine-tolerant animals develop increased sensitivity to thermal stimulation. A significant ($P<0.05$) reduction in paw-withdrawal latency over time and before implantation of the osmotic minipump is characterized as thermal hyperalgesia.

After the Hargreave's test, the development of antinociceptive tolerance was determined in all animals as follows. Acute nociception. The tail flick test, which measures withdrawal latencies of the tail from a noxious radiant heat source was used to measure thermal nociceptive sensitivity with baseline latencies of 4-5 sec and a cut-off time of 10 sec to prevent tissue injury (D'Amour, 1941). Tolerance to the antinociceptive effect of morphine was indicated by a significant ($P<0.05$) reduction in tail flick latency after challenge with an acute dose of morphine (6 mg/kg, given i.p) at 30 min post injection time point, a time previously demonstrated to produce maximal antinociception at this dose. Data obtained were converted to percentage maximal possible antinociceptive effect (% MPE) as follows: (response latency-baseline latency)/(cut off latency-baseline latency)×100. Test substances or vehicle were given on day 0-6 after completion of the behavioral tests. At the required time points after the behavioral tests, spinal cord tissues from the lumbar enlargement segment of the spinal cord (L4-L6) and dorsal horn tissues were removed and tissues processed for immunohistochemical, Western blot and biochemical analysis. All experiments were conducted with the experimenters blinded to treatment conditions.

Immunohistochemical and Immunofluorescent detection. For nitrated proteins in the spinal cord, the lumbar sections (L4-L6) were fixed and processed for immunohistochemical staining as described (Wang et al., 2004; Ndengele et al., 2008) using a well characterized monoclonal anti-nitrotyrosine antibody (1: 100 in 10% normal horse serum, Calbiochem, La Jolla Calif.). The processed samples were visualized for immunolabeling with secondary antibody, NB complex, and diaminobenzidine accordingly to the manufacturer's instructions (Vector ABC Elite Kit, Vector Laboratories, Burlingame Calif.).

For ceramide expression in spinal cord, formalin-fixed and OCT-embedded (Sakura Finetek USA, Torrance Calif.) lumbar portions of the spinal cord (L4-L6) were sectioned at 10!-lm and stored at −20° C. until use. The sections were rinsed in PBS, immersed in 40 ml of DIVA de-cloaker (Bio-Care Medical, Concord Calif.), and subjected to antigen retrieval in a pressure cooker at 100° C. for 5 minutes. The slides were cooled to room temperature (RT), rinsed in PBS, and incubated in blocking buffer (PBS, 5% normal goat serum, 1% bovine serum albumin (BSA), and 0.25% Triton X-100) for 2 h, humidified at RT. The blocked sections were rinsed in PBS and dual-labeled for 16 h, humidified at 4° C.

with a well characterized rabbit polyclonal anti-ceramide antibody (Krishnamurthy et al., 2007) (1:50 or 1:100) and with murine monoclonal anti-NeuN (1:200) (Chemicon, Billerica Mass.) for neurons, murine monoclonal anti-GFAP (1:100) (Abcam, Cambridge Mass.) for astrocytes, or murine monoclonal anti-Iba1 (1:100) (Abcam, Billerica Mass.) for microglia in diluted blocking buffer (1:10). The sections were rinsed in PBS; and the proteins were detected with goat anti-rabbit rhodamine and goat anti-mouse Alexafluor 488 (1:300, Invitrogen, Carlsbad Calif.) in diluted blocking buffer (1:10) for 2 h, humidified at RT. Following a PBS rinse, the sections were mounted in VectaShield with DAPI (Vector Laboratories, Burlingame Calif.), coverslipped, and photographed with an Olympus FV 1000 MPE confocal microscope. Sections treated with normal rabbit IgG or normal mouse IgG (Sigma, St. Louis Mo.) at equivalent concentrations to primary antibodies were used as controls yielding only non-specific background fluorescence.

Immunoprecipitation and Immunoblotting. Cytosolic fractions and P2 membranes were obtained as previously described (Takagi et al., 2000; Wang et al., 2004; Muscoli et al., 2007) and stored immediately at −80° C. Immunoprecipitation and Western blot analyses were performed as described (Takagi et al., 2000; Wang et al., 2004; Muscoli et al., 2007). Proteins were resolved with 7.5% (GLT-1), 10% (glutamine synthetase and GFAP), or 420% (Iba1) SDS-PAGE prior to electrophoretic transfer. Membranes were blocked for 1 h at RT in 1% BSA in TBS-T (50 mM Tris HCl, (pH 7.4), 150 mM NaCl, 0.01% Tween-20) and 0.1% thimerosal; then probed with mouse monoclonal anti-glutamine synthetase (1:2000, BD, San Jose Calif.), polyclonal rabbit anti-GLT-1 (1:1000, Alpha Diagnostic, San Antonio Tex.), monoclonal mouse anti-GFAP (1:1000, Dako, Carpinteria Calif.), or polyclonal goat anti-Iba1 1:1000, Waco, Richmond Va.) antibodies. Membranes were washed with TBS/T and visualized with horseradish peroxidase-conjugated secondary antibodies (Thermo Fisher Scientific, Rockford Ill.) for] hat RT and enhanced chemiluminescence (ECL, GEHealthcare, Piscataway N.J. or Femto kit, Thermo Fisher Scientific, Rockford Ill.). Rat brain lysate (Upstate, Billerica Mass.) containing most of the proteins expressed by nervous tissue was used as positive control. The blots were stripped and probed with a murine monoclonal anti-~-actin antibody (1:2000, Sigma, St. Louis Mo.). The relative density of the protein bands of interest were determined from film using ImageQuant 5.2 software (Molecular Dynamics, CA) and normalized to β-actin bands.

Statistical Analysis of the Data. Data were analyzed by analysis of variance (ANOVA) followed by Dunnett's post hoc test was employed with statistical significant differences defined at a P-value<0.05. All statistical analysis was performed using GraphPad Prism (Release 5.03, GraphPad Software, Inc, La Jolla, Calif.).

Chemotherapy-Induced Neuropathic Pain

Experimental animals. Male Sprague Dawley rats (200-220 g starting weight) or mice (25-30 g weight at the time of surgery) from Harlan (Indianapolis, Ind.) were housed 3-4 per cage in a controlled environment (12 h light/dark cycle) with food and water available ad libitum. All experiments were performed in accordance with the International Association for the Study of Pain and the National Institutes of Health guidelines on laboratory animal welfare and the recommendations by Saint Louis University Institutional Animal Care and Use Committee. All experiments were conducted with the experimenters blinded to treatment conditions.

Paclitaxel-Induced: Paclitaxel-induced pain was studied by means of the well-characterized rat model developed by Bennett in which repeated intraperitoneal (i.p) injections of low doses of paclitaxel are administered to induce neuropathic pain (mechano-allodynia and mechano-hyperalgesia) with little systemic toxicity or motor impairment (Polomano et al., Pain 94, 293-304 (2001)). The behavioral responses last for several weeks to months, thus modeling painful neuropathies in patients. Paclitaxel (Parentapharm. Yardley, Pa.) or its vehicle (Cremophor EL and 95% dehydrated ethanol in 1:1 ratio) was injected i.p in rats on four alternate days (day 0, 2, 4 and 6 with a final cumulative dose of 4 mg/kg). MnTE-2-PyP$^{5+}$, W146 (source), W140 (source) or their vehicle were delivered by intrathecal (i.th) injection (total volume of 10 μl followed by a 10 μl flush with sterile physiological saline) in rats chronically implanted with i.th cannulas using the L5/L6 lumbar approach, as described previously and commonly used for drug delivery (Ramos et al. Neuroscience 169, 1888-1900 (2010); Schoeniger-Skinner, Brain Behav Immun 21, 660-667 (2007); Doyle, et al. Neurosci Lett (2010)). Drugs were injected 30 min before paclitaxel or its vehicle from day (D) 0 and then daily up to D15. In another set of experiments, Fingolimod (Fingolimod, Cayman Chemicals, Ann Arbor, Mich.) or its vehicle (1.2% ethanol in saline) were given by intraperitoneal injection (i.p, 0.2 ml) from D0 to D15; behavioral testing was carried out on D0 and at baseline and subsequently on D12, D16 and D22.

Oxaliplatin and Bortezomib Induced: Oxaliplatin (Oncology Supply. Dothan, Ala.) or its vehicle (5% dextrose) was injected i.p. in rats on five consecutive days (DO to 4) for a final cumulative dose of 10 mg/kg. Bortezomib (Selleck Chemicals. Houston, Tex.) or its vehicle (5% Tween80, 5% EtOH) was injected i.p. in rats on five consecutive days (DO to 4) for a final cumulative dose of 1 mg/kg. Fingolimod (Fingolimod, Cayman) or its vehicle (1.2% ethanol in saline) were given by intraperitoneal injection (i.p, 0.2 ml) from D0 to D15; behavioral testing was carried out on D0 and at baseline and subsequently on D12, D16, and D22.

Behavioral testing: Baseline values were taken from all rats on day 0 Baseline. Drugs or vehicles under investigation were then given, followed 30 min later by a chemotherapeutic or vehicle. Behavioral testing was subsequently carried out on D12, D16 and D22.

Mechano-Allodynia and mechano-hyperalgesia: Mechanical withdrawal thresholds were assessed with an automated electronic version of the von Frey test (dynamic plantar aesthesiometer, model 37450; Ugo Basile, Milan, Italy). Each rat was placed in a Plexiglas chamber (28×40× 35-cm, wire mesh floor) and allowed to acclimate for fifteen minutes. After acclimation, a servo-controlled mechanical stimulus (a pointed metallic filament) was applied to the plantar surface, which exerts a progressively increasing punctate pressure that reaches up to 50 g within 10 seconds. The pressure evoking a clear voluntary hind-paw withdrawal response (normally 40-45 g) was recorded automatically and taken as the mechanical threshold index. Mechanical threshold was assessed three times at each time point to yield a mean value, which is reported as mean absolute threshold (grams, g). The development of mechano-allodynia is evidenced by a significant (P<0.05) reduction in mechanical mean absolute paw-withdrawal thresholds (grams, g) at forces that failed to elicit withdrawal responses before paclitaxel treatment (baseline). Mechanical-hyperalgesia was assessed by the Randall and Sellitto paw pressure test 6 using an Ugo-Basile analgesiometer, which applies a linearly increasing mechanical force to the dorsum of the rat's hind paw. The nociceptive threshold was defined as the force (g) at which the rat withdrew its paw (cut off set at 250 g).

Paclitaxel treatments results in bilateral allodynia and hyperalgesia. Because thresholds did not differ between left and right hind paws at any time point in any group, values from both paws were averaged for further analysis and data presentation. Animals receiving paclitaxel or paclitaxel in the presence of the experimental test substance tested did not display sign of toxicities; they exhibited normal posture, grooming, locomotor behavior, hair coat was normal, no signs of piloerection or porphyrin, and gained body weight normally and comparably to vehicle treated rats.

Determination of sphingomyelinase activity. The sphingomyelinase activity was measured utilizing Amplex® Red Sphingomyelinase Assay Kit (Molecular Probes, Eugene, Oreg.) following the manufacturer's instructions. First, rat spinal cord or peripheral nerve tissue were homogenized in specific buffers, as previously described. For acid sphingomyelinase activity detection, sodium acetate (100 mM, pH 5.0) was used in the lysis buffer. In addition, for the detection of lysosomal acid sphingomyelinase activity EDTA (2 mM) was added to the lysis buffer. For neutral sphingomyelinase activity assay, the tissues were homogenized in a lysis buffer containing Hepes (20 mM, pH 7.4). Following homogenization, samples were pre-incubated with sphingomyelin for 0.5 h at 37° C., and then the sphingomyelinase activity was measured in a fluorescence microplate reader for 1.5 h. The sphingomyelinase activity was expressed as mU/s, normalized by protein concentration (μg/mL). Hydrogen peroxide and purified sphingomyelinase were used as positive controls.

Determination of serine palmitoyl transferase (SPT) activity: SPT activity was determined by measuring the incorporation of [3H] serine into 3-ketosphinganine following a previously described method (Williams et al., Arch Biochem Biophys 228, 282-291 (1984). SPT activity was measured by number of counts/min, normalized by protein concentration (ug/mL).

Immunofluorescence detection. For ceramide expression in spinal cord, formalin-fixed and OCT-embedded (Sakura Finetek USA, Torrance, Calif.) lumbar portions of the spinal cord (L4-L6) were sectioned at 10 μm and stored at −20° C. until use. The sections were rinsed in PBS, immersed in 40 ml of DIVA de-cloaker (BioCare Medical, Concord, Calif.), and subjected to antigen retrieval in a pressure cooker at 100° C. for 5 minutes. The slides were cooled to room temperature (RT), rinsed in PBS, and incubated in blocking buffer (PBS, 5% normal goat serum, 1% bovine serum albumin (BSA), and 0.25% Triton X-100) for 2 h, humidified at RT. The blocked sections were rinsed in PBS and dual-labeled for 16 h, humidified at 4° C. with a well characterized rabbit polyclonal anti-ceramide antibody 9 (1:50 or 1:100) and with murine monoclonal anti-GFAP (1:100) (Abcam, Cambridge, Mass.) for astrocytes diluted blocking buffer (1:10). The sections were rinsed in PBS; and the proteins were detected with goat anti-rabbit rhodamine and goat anti-mouse Alexafluor 488 (1:300, Invitrogen, Carlsbad Calif.) in diluted blocking buffer (1:10) for 2 h, humidified at RT. Following a PBS rinse, the sections were mounted in VectaShield with DAPI (Vector Laboratories, Burlingame Calif.), cover-slipped, and photographed with an Olympus FV1000MPE confocal microscope. Sections treated with normal rabbit IgG or normal mouse IgG (Sigma, St. Louis Mo.) at equivalent concentrations to primary antibodies were used as controls yielding only non-specific background fluorescence.

Morphine-Induced Hyperalgesia and Antinociceptive Tolerance

Experimental animals. Male Sprague Dawley rats (200-230 g) were purchased from Harlan (USA and Europe) and housed 3-4 per cage and maintained in controlled environment (12 h light/dark cycle) with food and water available ad libitum. All experiments were performed in accordance with the International Association for the Study of Pain and the National Institutes of Health guidelines on laboratory animal welfare and the recommendations by Saint Louis University Institutional Animal Care and Use Committee. All experiments were conducted with the experimenters blinded to treatment conditions.

Osmotic pump implantation. Male Sprague Dawley rats were lightly anesthetized with isoflurane and were subcutaneously implanted (in the interscapular region) with primed osmotic minipumps (Alzet 2001; Alza, Mountain View, Calif.), to deliver saline at 1 μl/h or morphine at 75 μg μl$^{-1}$ h$^{-1}$ over 7 days as described by King et al. (Pain 132, 154-168 (2007)) and Vera-Portocarrero et al. (Pain 129, 35-45 (2007)). The concentrations of morphine sulfate resulted in a daily dose of approximately 8-9 mg/kg (depending on the weight of the rat). Minipumps were filled according to manufacturer's specifications. The use of the osmotic pump ensures a continuous subcutaneously delivery of morphine avoiding intermittent periods of withdrawal. Rats were tested for analgesia at 2 h following minipump implant to verify that they were analgesic, and approximately 100% analgesia was achieved. This helped verify that the pumps are working well, which is typically not a problem. The integrity of the pump delivery system was reexamined at the end of each experiment when the spinal cords were harvested.

Drug administration: The test substances W146 or W140 or their vehicle (0.001% ethanol in saline) were delivered by intrathecal (i.th) injection in rats chronically implanted with i.th cannulas using the L5/L6 lumbar approach, as described previously and commonly used for drug delivery (Ramos et al., Neuroscience 169, 1888-1900 (2010); Schoeniger-Skinner et al., Brain Behav Immun 21, 660-667 (2007); Doyle et al., Neurosci Lett (2010)). Test substances were injected i.th once a day for 6 days in a total volume of 10 μl followed by a 10 μl flush with sterile physiological saline.

Behavioral Tests

Thermal hyperalgesia. Hyperalgesic responses to heat were determined by the Hargreaves' Method using a Basile Plantar Test (Ugo Basile; Comeria, Italy) 12 with a cut-off latency of 20 s employed to prevent tissue damage. Animals were allowed to acclimate within a Plexiglas enclosure on a clear glass plate in a quiet testing room. A mobile infrared generator was positioned to deliver a thermal stimulus directly to an individual hindpaw from beneath the chamber. The withdrawal latency period of injected paws was determined with an electronic clock circuit and thermocouple. Foot withdrawal latencies were taken on day 0 before implantation of the minipumps (baseline) and subsequently on day 1, 3 and 6 of the experimental period to determine whether morphine-tolerant animals develop increased sensitivity to thermal stimulation. A significant ($P<0.05$) reduction in paw-withdrawal latency over time and before implantation of the osmotic minipump is characterized as thermal hyperalgesia. After the Hargreave's test, the development of antinociceptive tolerance was determined in all animals as follows.

Acute nociception. The tail flick test, which measures withdrawal latencies of the tail from a noxious radiant heat source, was used to measure thermal nociceptive sensitivity with baseline latencies of 2-3 sec and a cut-off time of 10 sec to prevent tissue injury (D'Amour, J Pharmacol Exp Ther 72, 74-79 (1941)). Tolerance to the antinociceptive effect of morphine was indicated by a significant ($P<0.05$) reduction in tail flick latency after challenge with an acute dose of morphine sulfate (6 mg/kg, given i.p) at 30 min post injection time point, a time previously demonstrated to produce maximal antinociception at this dose. Data obtained were converted to percentage maximal possible antinociceptive effect (% MPE) as follows: (response latency−baseline latency)/(cut off latency−baseline latency)×100. Test substances or vehicle were given on day 0 through 6 after completion of the behavioral tests.

Carrageenan-Induced Thermal Hyperalgesia

Lightly anesthetized rats [$CO_2$ (80%)/$O_2$ (20%)] received a subplantar injection of carrageenan (50 μl of a 1% solution in saline) or its vehicle (50 μl saline) into the right hindpaw. Fingolimod or their vehicle was given by gavage (0.2 ml) 90 min before carrageenan or its vehicle. Hyperalgesic responses to heat were determined by the Hargreaves' Method using a Basile Plantar Test (Ugo Basile; Comeria, Italy) (Hargreaves et al., Pain 32, 77-88 (1988)) with a cut-off latency of 20 s employed to prevent tissue damage. Rats were individually confined to Plexiglas chambers. A mobile infrared generator was positioned to deliver a thermal stimulus directly to an individual hindpaw from beneath the chamber. The withdrawal latency period of injected paws was determined with an electronic clock circuit and thermocouple. Results are expressed as Paw-Withdrawal Latency (s).

Statistical Analysis. All data are expressed as a mean±SEM. Behavioral and S1P formation data were assessed by two-tailed two-way analysis of variance (ANOVA) with Bonferroni post hoc comparisons to paclitaxel- or morphine treated animals. The activities of ceramide-generating enzymes were analyzed by unpaired Student's t-test. Significance was defined at $P<0.05$.

Results

The development of paclitaxel-induced neuropathic pain is associated with increased spinal levels of ceramide and S1P The well-characterized rat model developed by Bennett's group in which repeated intraperitoneal (i.p) injections of low doses of paclitaxel induce neuropathic pain (mechano-allodynia and mechano-hyperalgesia) with little systemic toxicity or motor impairment (Polomano et al., Pain 94, 293-304 (2001)) was used. Pilot experiments revealed that neuropathic pain was significant by day 12 (D12) and peaked by D16. It was therefore decided to run time course studies from D0 to D16 with all biochemical evaluations performed at time of peak hyperalgesia, D16. All drugs or their vehicle were given intrathecally (i.th) from D0 to D15. When compared to the vehicle group, administration of paclitaxel led to the development of mechano-allodynia (FIG. 20A) and mechano-hyperalgesia (FIG. 20B) and this was associated with increased enzymatic activity of serine palmytoyl transferase (SPT, FIG. 21A) and sphingomyelinases (SMase, FIG. 21B) and increased formation of ceramide, a precursor in the biosynthesis of S1P, as detected by immunofluorescence, including in superficial layers of the spinal cord from the lumbar enlargement (L5-L6) (FIG. 21D). Furthermore, as can be seen in FIG. 21E, the time-dependent development of neuropathic pain was associated with a corresponding and time-dependent formation of S1P in dorsal horn tissues as measured by ELISA (Echelon Biosciences, Salt Lake City, Utah) following extraction of the sphingolipids.

Figure 9:
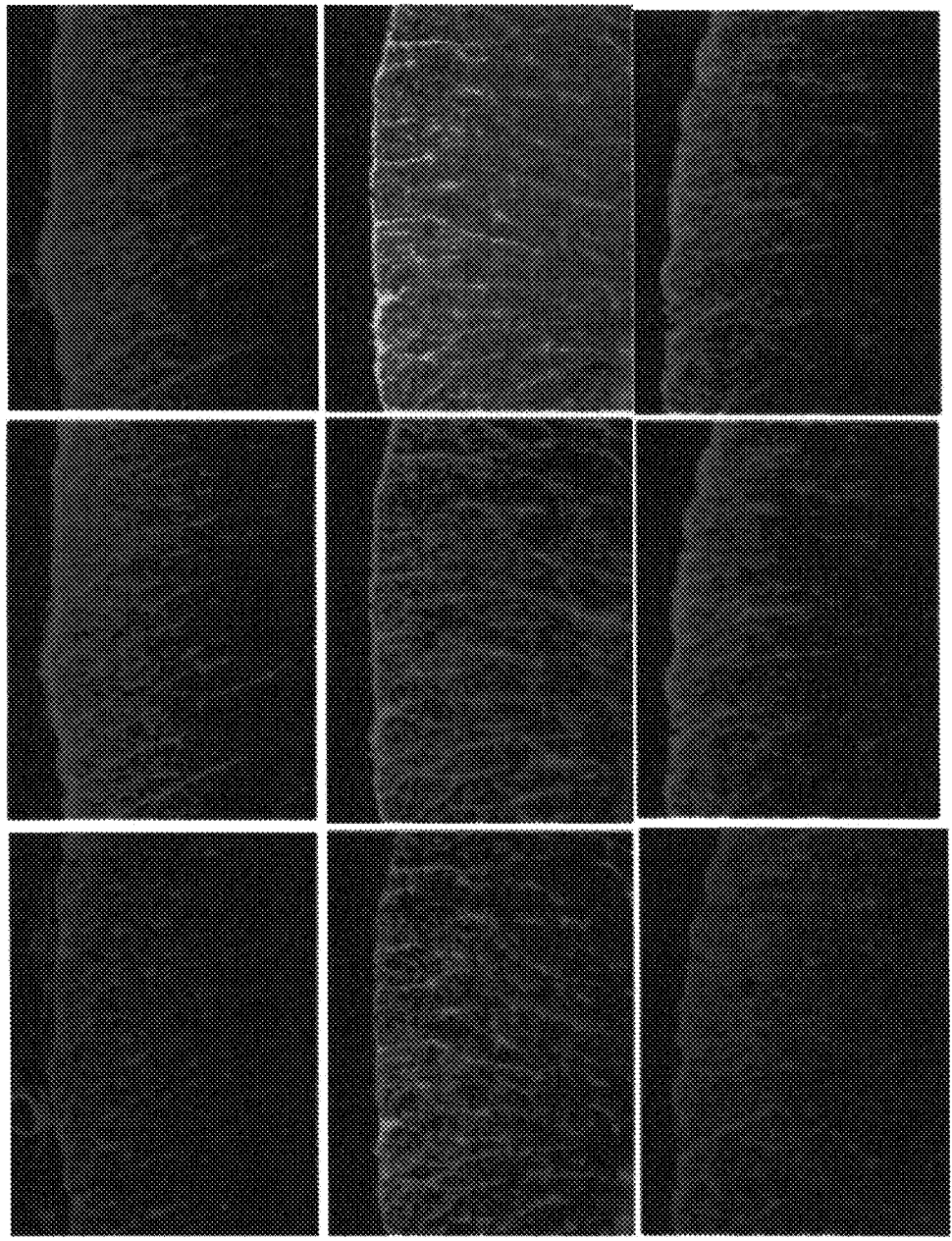

In addition, fixed frozen spinal cord sections from vehicle (Veh; A, C, E) and paclitaxel-treated animals (P; B, D, F) were stained for ceramide (NT; red; A, B) and GFAP (green; C, D) for astrocytes. When compared to the ceramide immunofluorescence in spinal cords from vehicle treated animals (FIG. 22A), paclitaxel substantially increased ceramide expression (FIG. 22B). In merged images (FIGS. 22E, F), paclitaxel-induced ceramide co-localized (yellow) with GFAP[+] astrocytes (FIG. 22F). Negative controls using normal rabbit serum for NT or normal mouse IgG for GFAP exhibited only low levels of background fluorescence. Micrographs are representative of at least 3 images of the superficial layers of dorsal horn (L4-L6) from 3 different animals performed on different days. See also FIG. 9.

S1P Acting Via the S1P1 Receptor Contributes to the Development of Paclitaxel-Induced Neuropathic Pain.

When compared to the vehicle group, administration of paclitaxel led to the development of mechano-allodynia and mechano-hyperalgesia that was attenuated in a dose-dependent manner by daily intrathecal delivery of the S1P1 antagonist, W146 (0.3-3 μM/day, n=5; FIGS. 20A and B) but not by W140 (3 μM/day, n=5; FIGS. 20A and B), its inactive S-enantiomer with doses chosen from previous studies (Rosen et al., Immunol Rev 223, 221-235 (2008); Sanna et al., Nat Chem Biol 2, 434-441 (2006)). When given alone, and at the highest dose tested (3 μM/day, n=5), W146 did not affect baseline withdrawal thresholds (FIGS. 20A and B).

Further investigations were conducted to ascertain whether Fingolimod could prevent the development of chemo-induced peripheral neuropathy ("CIPN"). Fingolimod is a novel S1P1 modulator recently approved by the FDA for the treatment of multiple sclerosis (Brinkmann et al., Nat Rev Drug Discov 9, 883-897 (2010)) and has shown beneficial effects in several preclinical models (e.g. cerebral ischemia, cancer, organ transplantation (Hla et al., Neurology 76, S3-8 (2011); Strader et al., J Nat Prod 74, 900-907 (2011)). Fingolimod becomes active in vivo following phosphorylation by sphingosine kinase 2 to form Fingolimod-P phosphate (Fingolimod-P) (Brinkmann et al., Nat Rev Drug Discov 9, 883-897 (2010)), which resembles the ligand S1P and competes with it to bind to four of the five S1P receptors. Fingolimod-P has the highest binding affinity for S1P1, binding to S1P3 and S1P5 with slightly lower affinity, and has no reported affinity for S1P2 (Brinkmann et al., Nat Rev Drug Discov 9, 883-897 (2010)).

Binding of either S1P or Fingolimod-P to S1P1, 3 or 5 receptors causes internalization of the receptor but whereas binding by S1P results in the receptor being recycled to the cell surface within approximately 2 h, binding by Fingolimod-P is believed to block the receptor recycling pathway and thus leads to receptor degradation. Several studies estimated that it takes 2 to 8 days after exposure to Fingolimod-P for cells to recover normal expression of S1P1, 3, 5 receptors. The immunosuppressive effects of Fingolimod rely on down-regulation of the S1P1 (Brinkmann et al., Nat Rev Drug Discov 9, 883-897 (2010)) studies supported by the observations in a knock-in mouse (S1p1rS5A/S5A) in which the carboxy-terminal serine-rich S1P1 motif, which is important for S1P1 receptor internalization but dispensable for S1P1 receptor signaling, is mutated. This mutation attenuated the beneficial effects of the drug (Thangada, S., et al. Cell-surface residence of sphingosine 1-phosphate receptor 1 on lymphocytes determines lymphocyte egress kinetics. J Exp Med 207, 1475-1483 (2010)). Without being bound to any particular theory, it is becoming clear that Fingolimod has beneficial effects in a variety of preclinical studies that are independent of its immune cell trafficking (Hla et al., Neurology 76, S3-8 (2011); Strader et al., J Nat Prod 74, 900-907 (2011); Thangada et al., J Exp Med 207, 1475-1483 (2010); Choi et al., Proc Natl Acad Sci USA 108, 751-756 (2011)); the relative receptors involved will probably depend upon individual circumstance.

Paclitaxel-Induced Neuropathic Pain is Blocked by Fingolimod

When compared to the vehicle-treated group, administration of paclitaxel led to the development of mechano-allodynia (FIG. 23A) and mechano-hyperalgesia (FIG. 23B) that peaked by D16 and plateaued by D22. The development of mechano-allodynia and mechano-hyperalgesia was attenuated by daily (D0-D15) administration of Fingolimod (0.01 mg/kg/d, i.p, n=6; FIGS. 23A, B). Importantly, and as can be seen, the development of mechano-allodynia and mechano-hyperalgesia as tested on D22 was not re-instated upon drug termination on D15. When given alone, Fingolimod did not affect baseline withdrawal thresholds (FIGS. 23A, B).

Oxaliplatin-Induced Neuropathic Pain is Blocked by Fingolimod

When compared to the vehicle-treated group, administration of oxaliplatin led to the development of mechano-allodynia (FIG. 24A) and mechano-hyperalgesia (FIG. 24B) that peaked by D16 and plateaued by D22. The development of mechano-allodynia and mechano-hyperalgesia was attenuated by daily (D0-D15) administration of Fingolimod (0.01 mg/kg/d, i.p, n=6; FIGS. 24A, B). Doses of Fingolimod were identified from previous studies and chosen because they were shown not to possess immunosuppressive effects. Importantly, and as can be seen, the development of mechano-allodynia and mechano-hyperalgesia as tested on D22 was not re-instated upon drug termination on D15. When given alone, Fingolimod did not affect baseline withdrawal thresholds (FIGS. 24A, B).

The results of this study show that Fingolimod blocked the development of neuropathic pain. The effects were long-lasting; of particular importance were the findings that once treatment with Fingolimod was terminated on day 15 it was found that CIPN did not re-establish up to the remainder of the observation period D22. These findings are very exciting since they suggest that, once prevented from occurring, pain does not re-occur.

Chemotherapeutic strategies to treat various cancers are short-circuited by the numerous side-effects observed. Pain greatly reduces the success of such strategies by limiting doses and imparting psychological distress. New methodologies preventing chemotherapy-induced chronic neuropathic pain based upon the attenuation of S1P formation or inhibition of its action (anti-S1P antibodies, or selective receptor agonists/antagonists) would be transformative. The findings reported herein provide critical information necessary for confirming S1P as a new therapeutic target for improving the clinical efficacy of chemotherapeutic agents. Blocking CIPN would ensure that patients, who currently would not be candidates for treatment (or continued treatment) with drugs like paclitaxel due to impending neuropathy, would instead benefit from full power antitumor dosages. These findings support the contention that targeting the S1P pathway is a novel strategy for preventing the development of pain of chemotherapy-induced pain.

Role of the S1P1 Subtype in Morphine-Induced Hyperalgesia and Antinociceptive Tolerance The potential involvement of the S1P1 subtype was tested using W146, a potent, competitive, selective and well characterized S1P1 subtype antagonist (Rosen et al., Immunol Rev 223, 221-235 (2008); Sanna et al., Nat Chem Biol 2, 434-441 (2006); Im, Acta Pharmacol Sin 31, 1213-1222 (2010); Taha et al., Biochim Biophys Acta 1682, 48-55 (2004); Takabe et al. (2008)). W146 exhibits a Ki value of about 80 nM for the human receptor (GTP-γS binding assay) with equipotency at the murine S1P1 subtype. No antagonistic (or agonistic) activity has been observed against the other known S1P receptor subtypes at doses as high as 10-20 μM (Rosen et al., Immunol Rev 223, 221-235 (2008)). Most studies in the literature have used W146 in the 0.1-10 μM range (Rosen et al., Immunol Rev 223, 221-235 (2008); Sanna et al., Nat Chem Biol 2, 434-441 (2006); Im, Acta Pharmacol Sin 31, 1213-1222 (2010); Taha et al., Biochim Biophys Acta 1682, 48-55 (2004); Takabe et al. (2008)).

Figure 25:
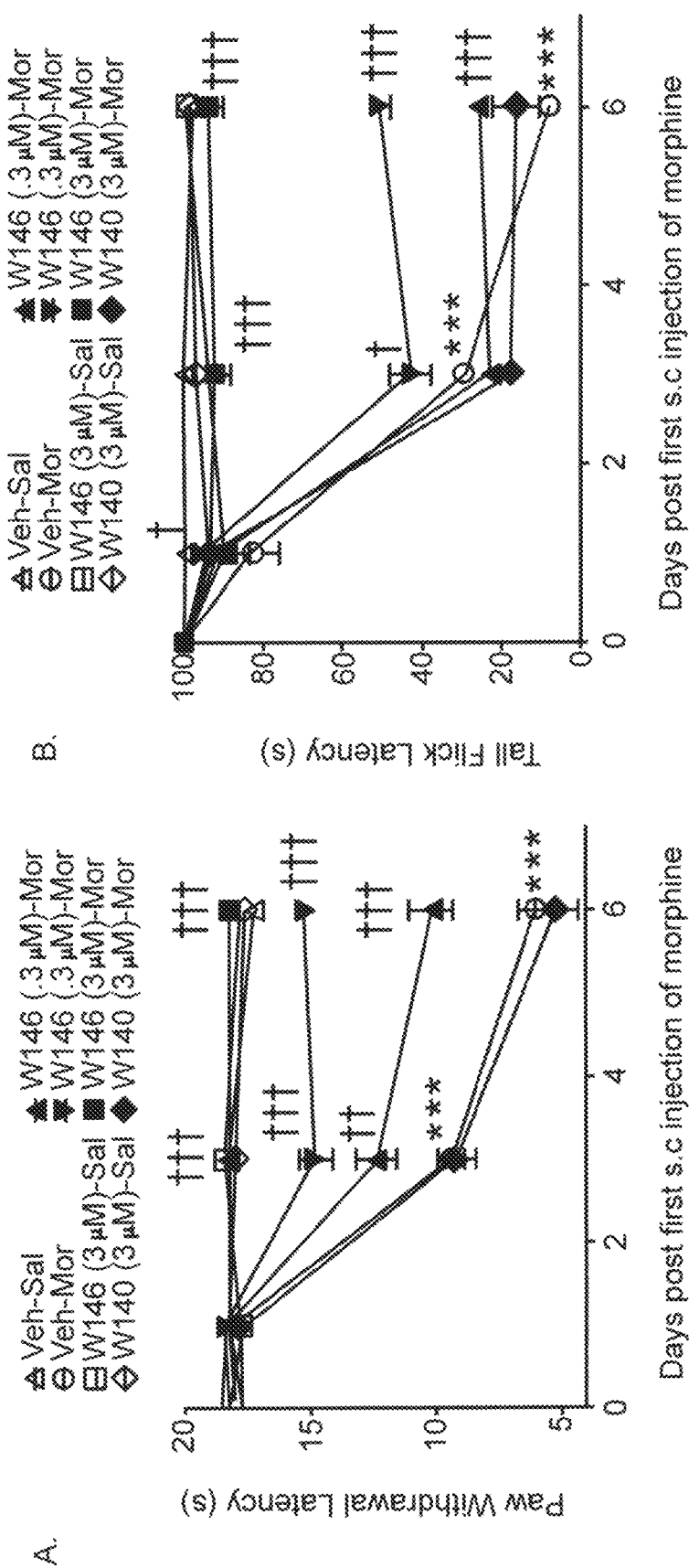

W146 was tested at 0.3, 1, and 3 μM. W146 or its vehicle (0.001% ethanol in saline) was injected i.th once a day for 5 days (starting at day D0) in a total volume of 10 μl followed by a 10 μl flush with sterile physiological saline in rats receiving s.c infusion of saline or morphine over 7 days. Injections were made after completion of the behavioral test (time interval between drug administrations, ~24 h). As can be seen in FIG. 25, when compared to rats that received a chronic s.c infusion of saline (Veh-Sal, n=5) over 7 days, infusion of morphine (Veh-Mor, n=5) over the same time frame led to (1) the development of thermal hyperalgesia (Hargreaves et al., Pain 32, 77-88 (1988), as evidenced by a significant dose-dependent reduction in hindpaw-withdrawal latency (s) on day (D) 3 and 6 but not D1, when compared to paw-withdrawal latency from before implantation of the osmotic minipump (D0) (FIG. 25A) and (2) the dose-dependent development of antinociceptive tolerance over the same time frame (FIG. 25B). The latter was indicated by a significant reduction in tail-flick latency (D'Amour, J Pharmacol xp Ther 72, 74-79 (1941)) 30 min after challenge with an acute dose of morphine (6 mg/kg, i.p) as evidenced on D3 and D6 but not D1 in rats that received morphine infusion over 7 days when compared to rats that received an infusion of saline over the same time frame (FIG. 6B).

Figure 26:
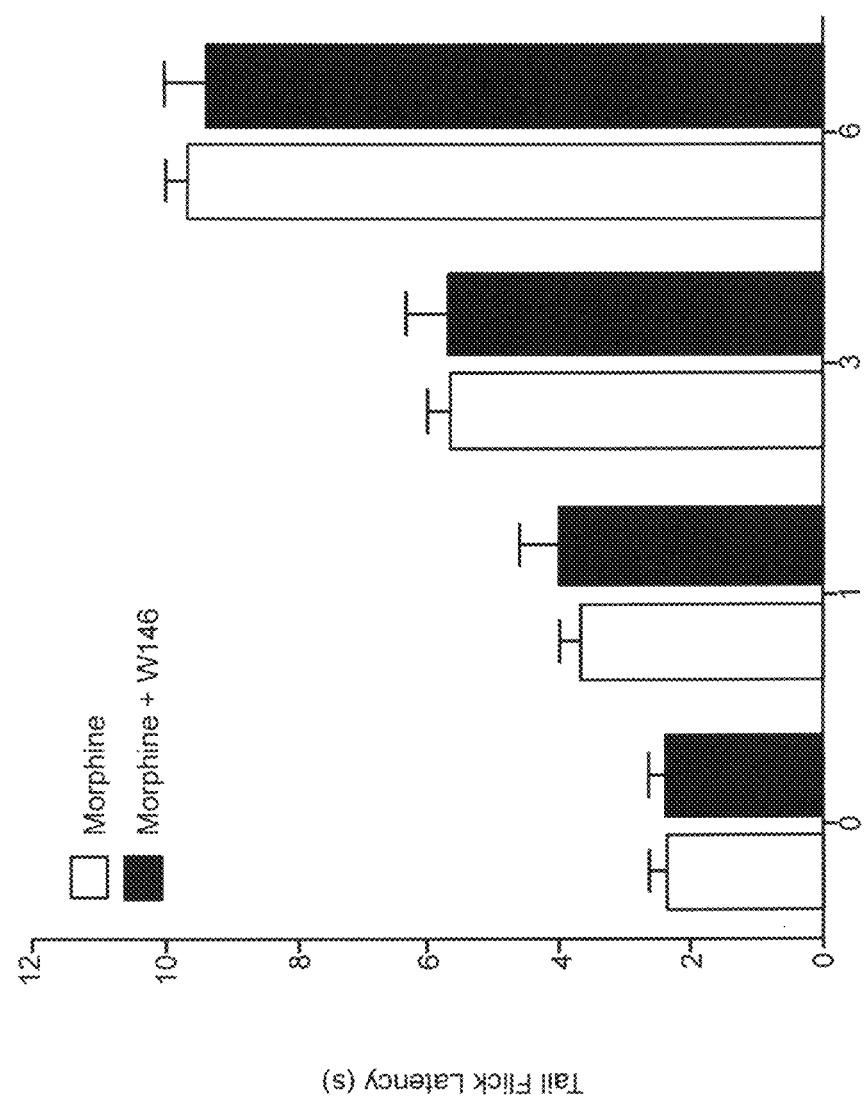

Co-administration of morphine with the S1P1 receptor antagonist W146 (n=5; 3 μM/day), but not with its inactive enantiomer, W140 (n=5; 3 μM/day), blocked the development of thermal hyperalgesia (Hargreaves et al. Pain 32, 77-88 (1988)) and antinociceptive tolerance (D'Amour, J Pharmacol xp Ther 72, 74-79 (1941)) by >90% and in a dose-dependent manner (FIGS. 25A,B). No observable side effects were seen (i.e. rat weights remained stable or increased, the rats were alert and active, no sign of motor function impairment was observed, exhibited normal grooming behavior and posture, hair coat was normal, no signs of piloerection or porphyrin, food and water intake remained within normal ranges). When compared to the vehicle group, daily i.th injections of W146 (n=5; 3 μM/day) or it inactive enantiomer, W140 (n=5; 3 μM/day), had no effect on hindpaw paw withdrawal or tail flick latencies (FIGS. 25A, B). Tail flick baseline latencies measured on D1, 3 and 6 before acute injection of morphine where similar to those obtained on D0 before minipump implantation and did not vary among the experimental groups over the time course study (ranged between 2-3 sec; not shown). The inhibitory effects of W146 were not attributable to acute antinociceptive interactions between W146 and acute morphine. Indeed, results shown in FIG. 26, clearly demonstrate that W146 (1 μM n=3) when given i.th 15 min before acute morphine at 1, 3 or 6 mg/kg (i.p, n=3) did not modify the dose-response to morphine. Tail flick latency (s) was tested before and 30 min after morphine (FIG. 26).

These findings indicate that targeting the S1P pathway is an effective way to prevent the development of morphine-induced hyperalgesia and antinociceptive tolerance in the management of severe pain.

Carrageenan Induced Thermal Hyperalgesia is Blocked by Fingolimod

Figure 27:
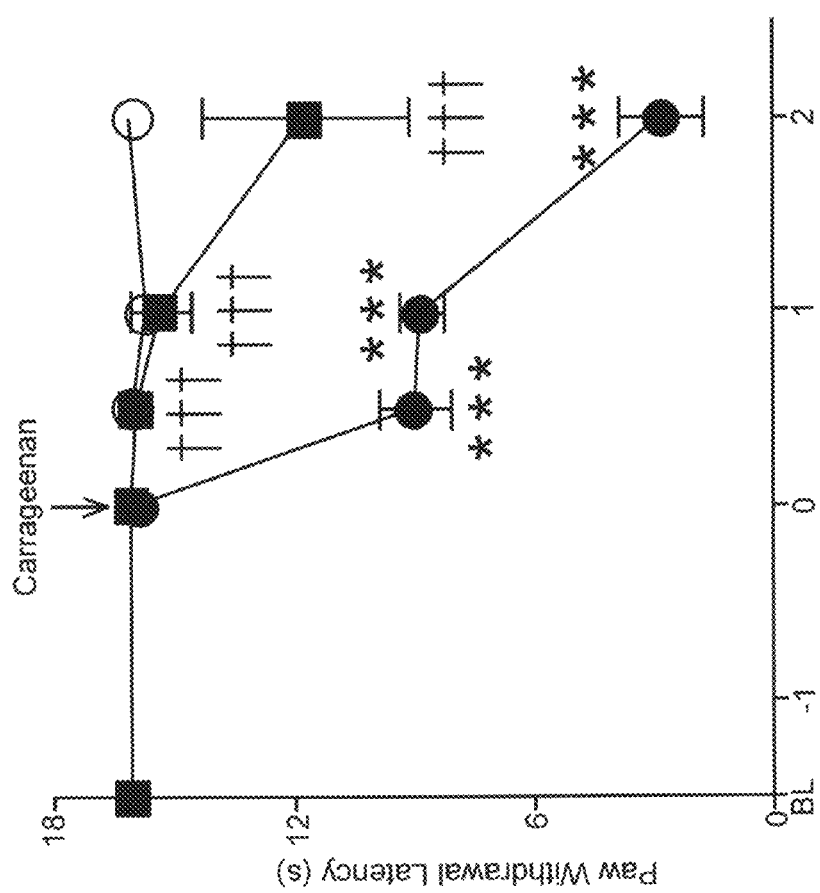
Figure 28:
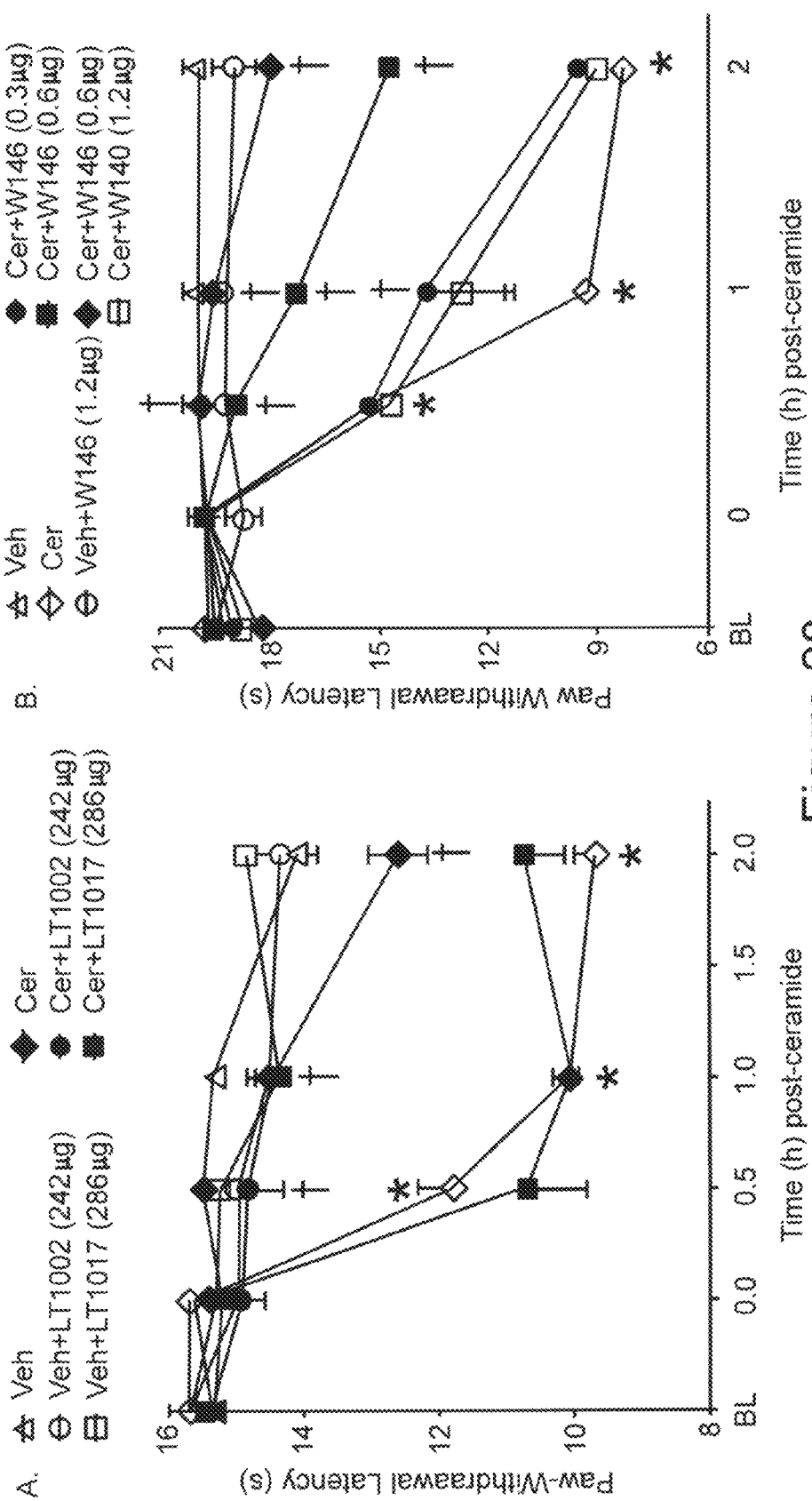

Intraplantar injection of carrageenan in rats led to the development of thermal hyperalgesia evidenced by decrease in paw withdrawal latencies using the Hargreaves test. Oral administration of Fingolimod (0.3 or 1 mg/kg) but not its vehicle (50% DMSO in distilled water) 90 min before carrageenan blocked hyperalgesia in a time-dependent fashion (FIG. 27).

Other Aspects

The detailed description set-forth above is provided to aid those skilled in the art in practicing the present invention. However, the invention described and claimed herein is not to be limited in scope by the specific aspects herein disclosed because these aspects are intended as illustration of several aspects of the invention. Any equivalent aspects are intended to be within the scope of this invention. Indeed, various modifications of the invention in addition to those shown and described herein will become apparent to those skilled in the art from the foregoing description which do not depart from the spirit or scope of the present inventive discovery. Such modifications are also intended to fall within the scope of the appended claims.

References Cited

All publications, patents, published patent applications and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

Publications incorporated herein by reference in their entirety include:

Arner S, Rawal N, Gustafsson LL (1988) Clinical experience of long-term treatment with epidural and intrathecal opioids—a nationwide survey. Acta Anaesthesiol Scand 32:253-259.

Beckman JS, Beckman TW, Chen J, Marshall PA, Freeman BA (1990) Apparent hydroxyl radical production by peroxynitrite: implications for endothelial injury from nitric oxide and superoxide. Proc Nat! Acad Sci USA 87:1620-1624.

Bryant L, Doyle T, Chen Z, Cuzzocrea S, Masini E, Vinci MC, Esposito E, Mazzon E, Petrusca DN, Petrache I, Salvemini D (2009) Spinal ceramide and neuronal apoptosis in morphine antinociceptive tolerance. Neurosci Lett 463:49-53.

Chiang CY, Wang J, Xie YF, Zhang S, Hu JW, Dostrovsky JO, Sessle BJ (2007) Astroglial glutamate-glutamine shuttle is involved in central sensitization of nociceptive neurons in rat medullary dorsal horn. J Neurosci 27:9068-9076.

Claus RA, Bunck AC, Bockmeyer CL, Brunkhorst FM, Losche W, Kinscherf R, Deigner H P (2005) Role of increased sphingomyelinase activity in apoptosis and organ failure of patients with severe sepsis. Faseb J 19:1719-1721.

Cui Y, Chen Y, Zhi JL, Guo RX, Feng J Q, Chen PX (2006) Activation of p38 mitogen-activated protein kinase in spinal microglia mediates morphine antinociceptive tolerance. Brain Res 1069:235-243.

Cuzzocrea S, Genovese T, Mazzon E, Esposito E, Crisafulli C, Di Paola R, Bramanti P, Salvemini D (2009) Fumonisin bl reduces the development of multiple organ failure induced by zymosan in mice. Shock 31: 170-177.

D'Amour F (1941) A method for determining loss of pain sensation. J Pharmacol xp Ther 72:74-79.

Danbolt N C (2001) Glutamate uptake. Prog NeuroBiol 65:1-105.

Delgado A, Casas J, Llebaria A, Abad JL, Fabrias G (2006) Inhibitors of sphingolipid metabolism enzymes. Biochim Biophys Acta 1758:1957-1977.

Delogu G, Famularo G, Amati F, Signore L, Antonucci A, Trinchieri V, Di Marzio L, Cifone MG (1999) Ceramide concentrations in septic patients: a possible marker of multiple organ dysfunction syndrome. Crit. Care Med 27:2413-2417.

Doyle T, Chena Z, Obeid L M, Salvemini D (2011) Sphingosine-1-phosphate acting via the S1P1 receptor is a downstream signaling pathway in ceramide-induced hyperalgesia. Neuroscience Letters 499: 4-8.

Doyle T, Chen Z, Muscoli C, Obeid LM, and Salvemini D (2011) Intraplantar-injected ceramide in rats induces hyperalgesia through an NF-B- and p38 kinasedependent cyclooxygenase 2/prostaglandin E2 pathway. The FASEB Journal article fj. 10-178095.

Foley KM (1995) Misconceptions and controversies regarding the use of opioids in cancer pain. Anticancer Drugs 6 Suppl 3:4-13.

French KJ, Schrecengost RS, Lee BD, Zhuang Y, Smith SN, Eberly JL, Yun JK, Smith CD (2003) Discovery and evaluation of inhibitors of human sphingosine kinase. Cancer Res 63:5962-5969.

Gorg B, Wettstein M, Metzger S, Schliess F, Haussinger D (2005) Lipopolysaccharide-induced tyrosine nitration and inactivation of hepatic glutamine synthetase in the rat. Hepatology 41: 1065-1073.

Hannun YA, Obeid LM (2008) Principles of bioactive lipid signalling: lessons from sphingolipids. Nat Rev Mol Cell Biol 9: 139-150.

Hargreaves K, Dubner R, Brown F, Flores C, Joris J (1988) A new and sensitive method for measuring thermal nociception in cutaneous hyperalgesia. Pain 32:77-88.

Jolly PS, Rosenfeldt HM, Milstien S, Spiegel S (2002) The roles of sphingosinel-phosphate in asthma. Mol Immunol 38:1239-1245.

Keller M, Lidington D, Vogel L, Peter BF, Sohn H Y, Pagano P J, Pitson S, Spiegel S, Pohl U, Bolz SS (2006) Sphingosine kinase functionally links elevated transmural pressure and increased reactive oxygen species formation in resistance arteries. FASEB J 20:702-704.

Kitano M, Hla T, Sekiguchi M, Kawahito Y, Yoshimura R, Miyazawa K, Iwasaki T, Sano H, Saba JD, Tam YY (2006) Sphingosine I-phosphate/sphingosine I-phosphate receptor 1 signaling in rheumatoid synovium: regulation of synovial proliferation and inflammatory gene expression. Arthritis Rheum 54:742-753.

Krishnamurthy K, Dasgupta S, Bieberich E (2007) Development and characterization of a novel anti-ceramide antibody. J Lipid Res 48:968-975.

Lai WQ, Irwan AW, Goh HH, Howe HS, Yu DT, Valle-Onate R, McInnes IB, Melendez A J, Leung BP (2008) Anti-inflammatory effects of sphingosine kinase modulation in inflammatory arthritis. J Immunol 181: 8010-8017.

Latremoliere A, Woolf CJ (2009) Central sensitization: a generator of pain hypersensitivity by central neural plasticity. J Pain 10:895-926.

Lee C, Xu DZ, Feketeova E, Kannan KB, Yun JK, Deitch EA, Fekete Z, Livingston DH, Hauser CJ (2004) Attenuation of shock-induced acute lung injury by sphingosine kinase inhibition. J Trauma 57:955-960.

Maines LW, Fitzpatrick LR, French KJ, Zhuang Y, Xia Z, Keller SN, Upson JJ, Smith CD (2008) Suppression of ulcerative colitis in mice by orally available inhibitors of sphingosine kinase. Dig Dis Sci 53:997-1012.

Mao J, Price DD, Mayer DJ (1995) Mechanisms of hyperalgesia and morphine tolerance: a current view of their possible interactions. Pain 62:259-274.

Melendez AJ (2008) Sphingosine kinase signalling in immune cells: potential as novel therapeutic targets. Biochim Biophys Acta 1784:66-75.

Milligan ED, Watkins LR (2009) Pathological and protective roles of glia in chronic pain. Nat Rev Neurosci 10:23-36.

Minana MD, Kosenko E, Marcaida G, Hermenegildo C, Montoliu C, Grisolia S,

Felipo V (1997) Modulation of glutamine synthesis in cultured astrocytes by nitric oxide. Cell Mol Neurobiol 17:433-445.

Muscoli C, Visalli V, Colica C, Nistico R, Palma E, Costa N, Rotiroti D, Nistico O, Mollace V (2005) The effect of inflammatory stimuli on NMDA-related activation of glutamine synthase in human cultured astroglial cells. Neurosci Lett 373:184-188.

Muscoli C, Cuzzocrea S, Ndengele MM, Mollace V, Porreca F, Fabrizi F, Esposito E, Masini E, Matuschak OM, Salvemini D (2007) Therapeutic manipulation of peroxynitrite attenuates the development of opiate-induced antinociceptive tolerance in mice. J Clin Invest 117:3530-3539.

Nakagawa T, Ozawa T, Shige K, Yamamoto R, Minami M, Satoh M (2001)

Inhibition of morphine tolerance and dependence by MS-153. a glutamate transporter activator. Eur J Pharmacol 419:39-45.

Narita M, Yoshida T, Nakajima M, Narita M, Miyatake M, Takagi T, Yajima Y, Suzuki T (2006) Direct evidence for spinal cord microglia in the development of a neuropathic pain-like state in mice. J Neurochem 97:1337-1348.

Nayak D, Huo Y, Kwang WX, Pushparaj PN, Kumar SD, Ling EA, Dheen ST (2010) Sphingosine kinase 1 regulates the expression of proinflammatory cytokines and nitric oxide in activated microglia. Neuroscience 166: 132-144.

Ndengele MM, Cuzzocrea S, Esposito E, Mazzon E, Di Paola R, Matuschak O M, Salvemini D (2008) Cyclooxygenases 1 and 2 contribute to peroxynitrite-mediated inflammatory pain hypersensitivity. Faseb J 22:3154-3164.

Ndengele MM, Cuzzocrea S, Masini E, Vinci MC, Esposito E, Muscoli C, Petrusca DN, Mollace Y, Mazzon E, Li D, Petrache I, Matuschak O M, Salvemini D (2009) Spinal ceramide modulates the development of morphine antinociceptive tolerance via peroxynitrite-mediated nitroxidative stress and neuroimmune activation. J Pharmacol Exp Ther 329:64-75.

Nishiuma T, Nishimura Y, Okada T, Kuramoto E, Kotani Y, Jahangeer S, Nakamura S (2008) Inhalation of sphingosine kinase inhibitor attenuates airway inflammation in asthmatic mouse model. Am J Physiol Lung Cell Mol Physiol 294:L1085-1093.

OsS1Pov MH, Lai J, Vanderah TW, Porreca F (2003) Induction of pain facilitation by sustained opioid exposure: relationship to opioid antinociceptive tolerance. Sci 73:783-800.

Pushparaj PN, H'Ng SC, Melendez AJ (2008) Refining siRNA in vivo transfection: silencing SPHK1 reveals its key role in C5a-induced inflammation in vivo. 1m J Biochem Cell Biol 40:1817-1825.

Renfrey S, Downton C, Featherstone J (2003) The painful reality. Nat Rev Drug Discov 2:175-176.

Romero-Sandoval A, Chai N, Nutile-McMenemy N, Deleo J A (2008a) A comparison of spinal Tha1 and GFAP expression in rodent models of acute and chronic pain. Brain Res 1219:116-126.

Romero-Sandoval E A, Horvath R J, DeLeo J A (2008b) Neuroimmune interactions and pain: focus on glial-modulating targets. Curr Opin Investig Drugs 9:726-734.

Salvemini D, Neumann WL (2009) Peroxynitrite: a strategic linchpin of opioid analgesic tolerance. Trends Pharmacol Sci 30: 194-202.

Salvemini D, Neumann W (2010) Targeting peroxynitrite driven nitroxidative stress with synzymes: A novel therapeutic approach in chronic pain management. Life Sci 86:604-614.

Salvemini D, Jensen MP, Riley DP, Misko TP (1998) Therapeutic manipulations of peroxynitrite. Drug News Perspect 11:204-214.

Simonnet G, Rivat C (2003) Opioid-induced hyperalgesia: abnormal or normal pain? Neuroreport 14: 1-7.

Snider AJ, Kawamori T, Bradshaw SG, Orr KA, Gilkeson GS, Hannun YA, Obeid LM (2009) A role for sphingosine kinase 1 in dextran sulfate sodium-induced colitis. Faseb J 23:143-152.

Storkson R V, Kjorsvik A, Tjolsen A, Hole K (1996) Lumbar catheterization of the spinal subarachnoid space in the rat. J Neurosci Methods 65: 167-172.

Suarez I, Bodega G, Fernandez B (2002) Glutamine synthetase in brain: effect of ammonia. Neurochem Int 41: 123-142.

Taha TA, Argraves KM, Obeid LM (2004) Sphingosine-1-phosphate receptors: receptor specificity versus functional redundancy. Biochim Biophys Acta 1682:48-55.

Takabe K, Paugh S W, Milstien S, Spiegel S (2008) "Inside-out" signaling of sphingosine-I-phosphate: therapeutic targets. Pharmacol Rev 60:181-195.

Takagi N, Logan R, Teves L, Wallace MC, Gurd JW (2000) Altered interaction between PSD-95 and the NMDA receptor following transient global ischemia. J Neurochem 74: 169-178.

Tanga FY, Nutile-McMenemy N, DeLeo JA (2005) The CNS role of Toll-like receptor 4 in innate neuroimmunity and painful neuropathy. Proc Natl Acad Sci USA 102:58565861.

Tanga FY, Raghavendra V, Nutile-McMenemy N, Marks A, Deleo JA (2006)

Role of astrocytic S100beta in behavioral hypersensitivity in rodent models of neuropathic pain. Neuroscience 140: 1003-1010.

Taylor DA, Fleming WW (200 I) Unifying perspectives of the mechanisms underlying the development of tolerance and physical dependence to opioids. J Pharmacol Exp Ther 297: 11-18.

Trotti D, Rolfs A, Danbolt NC, Brown RH, Jr., Hediger MA (1999) SOD1 mutants linked to amyotrophic lateral sclerosis selectively inactivate a glial glutamate transporter. Nat Neurosci 2:848.

Trotti D, Rossi D, Gjesdal O, Levy LM, Racagni G, Danbolt NC, Volterra A (1996) Peroxynitrite inhibits glutamate transpoller subtypes. J Biol Chem 271:5976-5979.

Trujillo KA, Akil H (1991) Inhibition of morphine tolerance and dependence by the NMDA receptor antagonist MK-801. Science 251:85-87.

Vera-Portocarrero L P, Zhang E T, King T, OsS1Pov M H, Vanderah T W, Lai J, Porreca F (2006) Spinal NK-1 receptor expressing neurons mediate opioid-induced hyperalgesia and antinociceptive tolerance via activation of descending pathways. Pain.

Wang Z, Ma W, Chabot JG, Quirion R (2009) Cell-type specific activation of p38 and ERK mediates calcitonin gene-related peptide involvement in tolerance to morphine-induced analgesia. Faseb J 23:2576-2586.

Wang ZQ, Porreca F, Cuzzocrea S, Galen K, Lightfoot R, Masini E, Muscoli C, Mollace V, Ndengele M, Ischiropoulos H, Salvemini D (2004) A newly identified role for superoxide in inflammatory pain. J Pharmacol Exp Ther 309:869-878.

Waniewski RA, Martin DL (1986) Exogenous glutamate is metabolized to glutamine and exported by rat primary astrocyte cultures. J Neurochem 47:304-313.

Watkins LR, Milligan ED, Maier SF (2001) Glial activation: a driving force for pathological pain. Trends Neurosci 24:450-455.

Watkins LR, Hutchinson MR, Johnston IN, Maier SF (2005) Glia: novel counter-regulators of opioid analgesia. Trends Neurosci 28:661-669.

Watkins LR, Hutchinson MR, Rice KC, Maier SF (2009) The "toll" of opioid-induced glial activation: improving the clinical efficacy of opioids by targeting glia. Trends Pharmacol Sci 30:581-591.

Zhang YH, Vasko MR, Nicol GD (2002) Ceramide, a putative second messenger for nerve growth factor, modulates the TTX-resistant Na(+) current and delayed rectifier K(+) current in rat sensory neurons. J Physiol 544:385-402.

Zhang YH, Fehrenbacher JC, Vasko MR, Nicol GD (2006) Sphingosine-1-phosphate via activation of a G-protein-coupled receptor(s) enhances the excitability of rat sensory neurons. J Neurophysiol 96: 1042-1052.

Hla T. et al. (2011) Sphingosine 1-phosphate (S1P): Physiology and the effects of S1P receptor modulation. Neurology 2011; 76; 53.

Brinkmann et al. (2010) Fingolimod (FTY720): discovery and development of an oral drug to treat multiple sclerosis. Nature Reviews, Drug Discovery 9: November 2010: 883-897.

Cusack et al. (2010) S1P, receptor agonists: Assessment of selectivity and current clinical activity. Current Opinion in Drug Discovery and Development 13 (4): 481-488.

Strader et al. (2011) Fingolimod (FTY720): A Recently Approved Multiple Sclerosis Drug Based on a Fungal Secondary Metabolite. J. Nat. Prod. 2011, 74, 900-907.

Polomano, R. C., Mannes, A. J., Clark, U. S. & Bennett, G. J. A painful peripheral neuropathy in the rat produced by the chemotherapeutic drug, paclitaxel. Pain 94, 293-304 (2001).

Storkson, R. V., Kjorsvik, A., Tjolsen, A. & Hole, K. Lumbar catheterization of the spinal subarachnoid space in the rat. J Neurosci Methods 65, 167-172 (1996).

Ramos, K. M., et al. Spinal upregulation of glutamate transporter GLT-1 by ceftriaxone: therapeutic efficacy in a range of experimental nervous system disorders. Neuroscience 169, 1888-1900 (2010).

Schoeniger-Skinner, D. K., et al. Interleukin-6 mediates low-threshold mechanical allodynia induced by intrathecal HIV-1 envelope glycoprotein gp120. Brain Behav Immun 21, 660-667 (2007).

Doyle, T., et al. Spinal NADPH oxidase is a source of superoxide in the development of morphine-induced hyperalgesia and antinociceptive tolerance. Neurosci Lett (2010).

Randall, L. O. & Selitto, J. J. A method for measurement of analgesic activity on inflamed tissue. Arch Int Pharmacodyn Ther 111, 409-419 (1957).

Dobrowsky, R. T. & Kolesnick, R. N. Analysis of sphingomyelin and ceramide levels and the enzymes regulating their metabolism in response to cell stress. Methods Cell Biol 66, 135-165 (2001).

Williams, R. D., Wang, E. & Merrill, A. H., Jr. Enzymology of long-chain base synthesis by liver: characterization of serine palmitoyltransferase in rat liver microsomes. Arch Biochem Biophys 228, 282-291 (1984).

Krishnamurthy, K., Dasgupta, S. & Bieberich, E. Development and characterization of a novel anti-ceramide antibody. J Lipid Res 48, 968-975 (2007).

King, T., et al. Morphine treatment accelerates sarcoma-induced bone pain, bone loss, and spontaneous fracture in a murine model of bone cancer. Pain 132, 154-168 (2007).

Vera-Portocarrero, L. P., et al. Spinal NK-1 receptor expressing neurons mediate opioid-induced hyperalgesia and antinociceptive tolerance via activation of descending pathways. Pain 129, 35-45 (2007).

Hargreaves, K., Dubner, R., Brown, F., Flores, C. & Joris, J. A new and sensitive method for measuring thermal nociception in cutaneous hyperalgesia. Pain 32, 77-88 (1988).

D'Amour, F. A method for determining loss of pain sensation. J Pharmacol xp Ther 72, 74-79 (1941).

Rosen, H., et al. Modulating tone: the overture of S1P receptor immunotherapeutics. Immunol Rev 223, 221-235 (2008).

Sanna, M. G., et al. Enhancement of capillary leakage and restoration of lymphocyte egress by a chiral S1P1 antagonist in vivo. Nat Chem Biol 2, 434-441 (2006).

Brinkmann, V., et al. Fingolimod (FTY720): discovery and development of an oral drug to treat multiple sclerosis. Nat Rev Drug Discov 9, 883-897 (2010).

Hla, T. & Brinkmann, V. Sphingosine 1-phosphate (S1P): Physiology and the effects of S1P receptor modulation. Neurology 76, S3-8 (2011).

Strader, C. R., Pearce, C. J. & Oberlies, N. H. Fingolimod (FTY720): A Recently Approved Multiple Sclerosis Drug Based on a Fungal Secondary Metabolite. J Nat Prod 74, 900-907 (2011).

Thangada, S., et al. Cell-surface residence of sphingosine 1-phosphate receptor 1 on lymphocytes determines lymphocyte egress kinetics. J Exp Med 207, 1475-1483 (2010).

Choi, J. W., et al. Fingolimod (FTY720) efficacy in an animal model of multiple sclerosis requires astrocyte sphingosine 1-phosphate receptor 1 (S1P1) modulation. Proc Natl Acad Sci USA 108, 751-756 (2011).

Im, D. S. Pharmacological tools for lysophospholipid GPCRs: development of agonists and antagonists for LPA and S1P receptors. Acta Pharmacol Sin 31, 1213-1222 (2010).

Taha, T. A., Argraves, K. M. & Obeid, L. M. Sphingosine-1-phosphate receptors: receptor specificity versus functional redundancy. Biochim Biophys Acta 1682, 48-55 (2004).

Takabe, K., Paugh, S. W., Milstien, S. & Spiegel, S. "Inside-out" signaling of sphingosine-1-phosphate: therapeutic targets. Pharmacol Rev 60, 181-195 (2008).

What is claimed is:

1. A method of treating chemotherapy induced neuropathic pain in an individual, the method comprising administering to the individual an effective amount of a drug selected from S1P receptor agonists and S1P receptor antagonists.

2. The method of claim 1, wherein the chemotherapy comprises the administration of a drug selected from the group consisting of taxanes, platinum compounds, vinca alkaloids, proteasome inhibitors, and combinations thereof.

3. The method of claim 2, wherein the chemotherapy is selected from the group consisting of paclitaxel, oxaliplatin, bortezomib, vincristine, and combinations thereof.

4. The method of claim 1, wherein the S1P receptor agonist is selected from the group consisting of Fingolimod, BAF312, Ponesimod, ONO-4641, CS-0777, KRP-203, PF-991, W146, and combinations thereof.

5. A method of treating opiate-induced pain-hypersensitivity in an individual, the method comprising administering to the individual an effective amount of a drug selected from S1P receptor agonists and S1P receptor antagonists.

6. The method of claim 5, wherein the opiate-induced pain-hypersensitivity is induced by morphine.

7. The method of claim 5, wherein the S1P receptor agonist is selected from the group consisting of Fingolimod, BAF312, Ponesimod, ONO-4641, CS-0777, KRP-203, PF-991, and W146.

* * * * *

UNITED STATES PATENT AND TRADEMARK OFFICE
CERTIFICATE OF CORRECTION

PATENT NO. : 8,747,844 B2
APPLICATION NO. : 13/189954
DATED : June 10, 2014
INVENTOR(S) : Daniela Salvemini It is certified that error appears in the above-identified patent and that said Letters Patent is hereby corrected as shown below:

On the title page, item (56) References Cited - Other Publications, delete the 3rd reference on page 1 "Doyle, Tim et al: "Sphingosine-1-phosphate acting via the S1P1 receptor is a downstream signaling pathway in ceraminde-induced hyperalgesia", Neuroscience Letters, vol. 499, No. 1, Jul. 1, 2011, pp. 4-8, XP55016229, ISSN: 0304-3940, DOI: 10.1016/j.neulet.2011.05.018 abstract; figure 3." and replace with --Doyle, Tim et al: "Sphingosine-1-phosphate acting via the S1P1 receptor is a downstream signaling pathway in ceramide-induced hyperalgesia", Neuroscience Letters, vol. 499, No. 1, Jul. 1, 2011, pp. 4-8, XP55016229, ISSN: 0304-3940, DOI: 10.1016/j.neulet.2011.05.018 abstract; figure 3.-- therefor.

On the title page, item (56) References Cited - Other Publications, delete the 9th reference on page 1 "Lai Wen-Qi et al: "Anti-Inflammatory effects of sphingosine kinase modulation in inflammatory arthritis.", Journal of Immunology (Baltimore, MD. :1950) Dec. 1, 2008 LNKD-PUBMD: 19017993, vol. 181, No. 11, Dec. 1, 2008, pp. 8010-8017, XP002662967, ISSN: 1550-6606 The whole document." and replace with --Lai Wen-Qi et al: "Anti-inflammatory effects of sphingosine kinase modulation in inflammatory arthritis.", Journal of Immunology (Baltimore, MD. :1950) Dec. 1, 2008 LNKD-PUBMED: 19017993, vol. 181, No. 11, Dec. 1, 2008, pp. 8010-8017, XP002662967, ISSN: 1550-6606 The whole document.-- therefor.

In the Specification

In column 1, lines 14-17, delete "This invention was made with Government support under National Institutes of Health Grants R01 DA024074 and R21 DA023056. The Federal Government has certain rights in the invention." and insert --This invention was made with Government support under grant numbers R01 DA024074 and R21 DA023056 awarded by the National Institutes of Health. The Government has certain rights in the invention.-- therefor.

Signed and Sealed this
Twenty-third Day of September, 2014

Michelle K. Lee
*Deputy Director of the United States Patent and Trademark Office*